(12) United States Patent
Baty et al.

(10) Patent No.: US 9,260,754 B2
(45) Date of Patent: Feb. 16, 2016

(54) CONNEXIN MUTATION DETECTION FOR LYMPHATIC VARIATION AND DISEASE

(75) Inventors: Catherine Baty, Pittsburgh, PA (US); Robert Ferrell, Pittsburgh, PA (US); David Finegold, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 79 days.

(21) Appl. No.: 13/106,424

(22) Filed: May 12, 2011

(65) Prior Publication Data
US 2012/0015356 A1  Jan. 19, 2012

Related U.S. Application Data

(60) Provisional application No. 61/333,794, filed on May 12, 2010.

(51) Int. Cl.
| | |
|---|---|
| *C12Q 1/68* | (2006.01) |
| *C07H 21/02* | (2006.01) |
| *C07H 21/04* | (2006.01) |

(52) U.S. Cl.
CPC ........ *C12Q 1/6883* (2013.01); *C12Q 2600/112* (2013.01); *C12Q 2600/156* (2013.01)

(58) Field of Classification Search
CPC ........... C12Q 1/6883; C12Q 2600/112; C12Q 2600/156; C12Q 1/6869; C12Q 2537/165; C12Q 2545/113; C12Q 1/6886; C12Q 2600/178; C12Q 2600/136; C12Q 2600/158; C12Q 1/26; C12Q 1/44; C12Q 1/68; C12Q 1/6806
See application file for complete search history.

(56) References Cited

PUBLICATIONS

Lucentini, Jack. Gene Association Studies Typically Wrong. 2004. The Scientist vol. 18, pp. 1-3.*
Hegele. Arterioscler Thromb Vasc Biol. 2002; 22:1058-1061.*
Mummidi et al Evolution of human and non human primate CC chemokine receptor 5 gene and mRNA. Journal of Biological Chemistry 2000 vol. 275, No. 25, pp. 18946-18961.*
Uhlenberg et al,. Am J Hum Genet 2004 vol. 75 pp. 251-260.*
Orthmann-Murphy (Brain: A Journal of Neurology 2009 pp. 426-438, vol. 132 pre published online Dec. 4, 2008).*
Ruf, N. et al., Analysis of Human Alternative First Exons and Copy Number Variation of the GJA12 Gene in Patients With Pelizaeus-Merzbacher-Like Disease, American Journal of Medical Genetics: Neuropsychiatric Genetics, 2009, pp. 226-232, vol. 150B.
Salviati, L. et al., A novel deletion in the GJA12 gene causes Pelizaeus-Merzbacher-like disease, Neurogenetics, 2007, pp. 57-60, vol. 8.
Schmitz, K.H. et al., Weight Lifting in Women with Breast-Cancer-Related Lymphedema, The New England Journal of Medicine, 2009, pp. 664-673, vol. 361.
Severs, N.J. et al., Immunocytochemical Analysis of Connexin Expression in the Healthy and Diseased Cardiovascular System, Microscopy Research and Technique, 2001, pp. 301-322, vol. 52.
Shibayama, J. et al., Functional Characterization of Connexin43 Mutations Found in Patients With Oculodentodigital Dysplasia, Circulation Research, 2005, pp. e83-e91, vol. 96.

Soran, A. et al., Breast Cancer-Related Lymphedema—What Are the Significant Predictors and How They Affect the Severity of Lymphedema?, The Breast Journal, 2006, pp. 536-543, vol. 12, No. 6.
Sosinsky, G.E. et al., Structural organization of gap junction channels, Biochimica et Biophysica Acta, 2005, pp. 99-125, vol. 1711.
Srinivas, M. et al., Functional Properties of Channels Formed by the Neuronal Gap Junction Protein Connexin36, The Journal of Neuroscience, 1999, pp. 9848-9855, vol. 19, No. 22.
Srinivas, M. et al., Voltage dependence of macroscopic and unitary currents of gap junction channels formed by mouse connexin50 expressed in rat neuroblastoma cells, Journal of Physiology, 1999, pp. 673-689, vol. 517, No. 3.
Stanton, A.W.B. et al., Lymphatic drainage in the muscle and subcutis of the arm after breast cancer treatment, Breast Cancer Res Treat, 2009, pp. 549-557, vol. 117.
Stanton, A.W.B. et al., Recent Advances in Breast Cancer-Related Lymphedema of the Arm: Lymphatic Pump Failure and Predisposing Factors, Lymphatic Research and Biology, 2009, pp. 29-45, vol. 7, No. 1.
Stout Gergich, N.L. et al., Preoperative Assessment Enables the Early Diagnosis and Successful Treatment of Lymphedema, Cancer, 2008, pp. 2809-2819, vol. 112.
Teubner, B. et al., Functional Expression of the New Gap Junction Gene Connexin47 Transcribed in Mouse Brain and Spinal Cord Neurons, The Journal of Neuroscience, 2001, pp. 1117-1126, vol. 21, No. 4.
Uhlenberg, B. et al., Mutations in the Gene Encoding Gap Junction Protein α12 (Connexin 46.6) Cause Pelizaeus-Merzbacher-Like Disease, Am. J. Hum. Genet., 2004, pp. 251-260, vol. 75.
Verma, V. et al., Novel Pharmacophores of Connexin43 Based on the "RXP" Series of Cx43-Binding Peptides, Circ Res, 2009, pp. 176-184, vol. 105.
Von Der Weid, P-Y. et al., Functional electrical properties of the endothelium in lymphatic vessels of the guinea-pig mesentery, Journal of Physiology, 1997, pp. 439-451, vol. 504, No. 2.
Warner, A. et al., Specific motifs in the external loops of connexin proteins can determine gap junction formation between chick heart myocytes, Journal of Physiology, 1995, pp. 721-728, vol. 488, No. 3.
Wei, C-J. et al., Connexins and Cell Signaling in Development and Disease, Annu. Rev. Cell Dev. Biol., 2004, pp. 811-838, vol. 20.
Wick, N. et al., Transcriptomal comparison of human dermal lymphatic endothelial cells ex vivo and in vitro, Physiol Genomics, 2007, pp. 179-192, vol. 28.
Wolf, N.I. et al., Frameshift mutation in GJA12 leading to nystagmus, spastic ataxia and CNS dys-/demyelination, Neurogenetics, 2007, pp. 39-44, vol. 8.
Xu, X. et al, Connexin 43-mediated modulation of polarized cell movement and the directional migration of cardiac neural crest cells, Development, 2006, pp. 3629-3639, vol. 133.
Zawieja, D.C. et al., Distribution, propogation, and coordination of contractile activity in lymphatics, Am. J. Physiol., 1993, pp. H1283-H1291, vol. 264.
Abbaci, M. et al., Advantages and limitations of commonly used methods to assay the molecular permeability of gap junctional intercellular communication, BioTechniques, 2008, pp. 33-62, vol. 45.
Alders, M. et al., Mutations in CCBE1 cause generalized lymph vessel dysplasia in humans, Nature Genetics, 2009, pp. 1272-1274, vol. 41, No. 12.
Berthoud et al., Peptide inhibitors of intercellular communication, Am J Physiol Lung Cell Mol Physiol, 2000, pp. L619-L622, vol. 279.
Bugiani, M. et al., GJA12 mutations in children with recessive hypomyelinating leukoencephalopathy, Neurology, 2006, pp. 273-279, vol. 67.

(Continued)

*Primary Examiner* — Amanda Haney
(74) *Attorney, Agent, or Firm* — The Webb Law Firm

(57) ABSTRACT

Methods are provided for identifying risk of developing lymphedema, including primary and secondary edema. The methods comprise identifying the presence in a biological sample of a polymorphism in one or more of GJA4, GJA5 and GJC2, resulting in a functional mutation of one or more of connixin 37 (Cx37), Cx40 or Cx47.

3 Claims, 22 Drawing Sheets

(56) References Cited

PUBLICATIONS

Clarke, T.C. et al., The antiarrhythmic peptide rotigaptide (ZP123) increases gap junction intercellular communication in cardiac myocytes and HeLa cells expressing connexin 43, British Journal of Pharmacology, 2006, pp. 486-495, vol. 147.

Connell, F. et al., Lymphoedema Consortium, Linkage and sequence analysis indicate that CCBE1 is mutated in recessively inherited generalised lymphatic dysplasia, Human Genetics, 2010, pp. 231-241, vol. 127.

Cruciani, V. et al., The Detection of Hamster Connexins: A Comparison of Expression Profiles with Wild-Type Mouse and the Cancer-Prone Min Mouse, Cell Communication and Adhesion, 2004, pp. 155-171, vol. 11.

Cruciani, V. et al., The connexin gene family in mammals, Biol. Chem., 2005, pp. 325-332, vol. 386.

Del Corsso, C. et al., Transfection of mammalian cells with connexins and measurement of voltage sensitivity of their gap junctions, Nature Protocols, 2006, pp. 1799-1809, vol. 1, No. 4.

Diekmann, S. et al., Pelizaeus-Merzbacher-like disease is caused not only by a loss of connexin47 function but also by a hemichannel dysfunction, European Journal of Human Genetics, 2010, pp. 985-992, vol. 18.

Dobrowolski, R. et al., Connexin-Caused Genetic Diseases and Corresponding Mouse Models, Antioxidants and Redox Signaling, 2009, pp. 283-295, vol. 11, No. 2.

Ek-Vitorin, J.F. et al., Quantification of gap junction selectivity, Am J Physiol Cell Physiol, 2005, pp. C1535-C1546, vol. 289.

Elfgang, C. et al., Specific Permeability and Selective Formation of Gap Junction Channels in Connexin-transfected HeLa Cells, The Journal of Cell Biology, 1995, pp. 805-817, vol. 129, No. 3.

El-Fouly, M.H. et al., Scrape-Loading and Dye Transfer: A Rapid and Simple Technique to Study Gap Junctional Intercellular Communication, Experimental Cell Research, 1987, pp. 422-430, vol. 168.

Elias, L.A.B. et al., Gap junction adhesion is necessary for radial migration in the neocortex, Nature, 2007, pp. 901-908, vol. 448.

Fang, J. et al., Mutations in FOXC2 (MFH-1), a Forkhead Family Transcription Factor, Are Responsible for the Hereditary Lymphedema-Distichiasis Syndrome, Am. J. Hum. Genet., 2000, pp. 1382-1388, vol. 67.

Ferrell, R.E. et al., Hereditary lymphedema: evidence for linkage and genetic heterogeneity, Human Molecular Genetics, 1998, pp. 2073-2078, vol. 7, No. 13.

Ferrell, R.E. et al., Candidate Gene Analysis in Primary Lymphedema, Lymphatic Research and Biology, 2008, pp. 69-77, vol. 6, No. 2.

Ferrell, R.E. et al., GJC2 Missense Mutations Cause Human Lymphedema, The American Journal of Human Genetics, 2010, pp. 943-948, vol. 86, No. 6.

Finegold, D.N. et al., Truncating mutations in FOXC2 cause multiple lymphedema syndromes, Human Molecular Genetics, 2001, pp. 1185-1189, vol. 10, No. 11.

Finegold, D.N. et al., HGF and MET Mutations in Primary and Secondary Lymphedema, Lymphatic Research and Biology, 2008, pp. 65-68, vol. 6, No. 2.

Geback, T. et al., TScratch: a novel and simple software tool for automated analysis of monolayer wound healing assays, BioTechniques, 2009, pp. 265-274, vol. 46.

Goodenough, D.A. et al., Gap Junctions, Cold Spring Harbor Perspectives in Biology, 2009, 19 pages, 1:a002576.

Hayes, S.C. et al., Lymphedema After Breast Cancer: Incidence, Risk Factors, and Effect on Upper Body Function, Journal of Clinical Oncology, 2008, pp. 3536-3542, vol. 26, No. 21.

Henneke, M. et al., GJA12 mutations are a rare cause of Pelizaeus-Merzbacher-like disease, Neurology, 2008, pp. 748-754, vol. 70.

Irrthum, A. et al., Mutations in the Transcription Factor Gene SOX18 Underlie Recessive and Dominant Forms of Hypotrichosis-Lymphedema-Telangiectasia, Am. J. Hum. Genet., 2003, pp. 1470-1478, vol. 72.

Karkkainen, M.J. et al., Missense mutations interfere with VEGFR-3 signalling in primary lymphoedema, Nature Genetics, 2000, pp. 153-159, vol. 25.

Karpanen, T. et al., Molecular Biology and Pathology of Lymphangiogenesis, Annu. Rev. Pathol. Mech. Dis., 2008, pp. 367-397, vol. 3.

Kjolbye, A.L. et al., Maintenance of intercellular coupling by the antiarrhythmic peptide rotigaptide suppresses arrhythmogenic discordant alternans, Am. J. Physiol. Heart Circ. Physiol., 2008, pp. H41-H49, vol. 294.

Kobayashi, M.R. et al., Lymphedema, Clinics in Plastic Surgery, 1987, pp. 303-313, vol. 14, No. 2.

Laird, D.W., Closing the Gap on Autosomal Dominant Connexin-26 and Connexin-43 Mutants Linked to Human Disease, The Journal of Biological Chemistry, 2008, pp. 2997-3001, vol. 283, No. 6.

Laird, D.W., The gap junction proteome and its relationship to disease, Trends in Cell Biology, 2010, pp. 92-101, vol. 30, No. 10.

Leak, L.V., The structure of lymphatic capillaries in lymph formation, Federation Proc., 1976, pp. 1863-1871, vol. 35, No. 8.

Liersch, R. et al., Lymphangiogenesis in development and disease, Thromb Haemost, 2007, pp. 304-310, vol. 98, No. 2.

Maeda, S. et al., Structure of the gap junction channel and its implications for its biological functions, Cell. Mol. Life Sci., 2011, pp. 1115-1129, vol. 68.

McHale, N.G. et al., Co-ordination of pumping in isolated bovine lymphatic vessels, Journal of Physiology, 1992, pp. 503-512, vol. 450.

McLachlan, E. et al., Functional Characterization of Oculodentodigital Dysplasia-Associated Cx43 Mutants, Cell Communication and Adhesion, 2005, pp. 279-292, vol. 12.

Menichella, D.M. et al., Connexins are Critical for Normal Myelination in the CNS, The Journal of Neuroscience, 2003, pp. 5963-5973, vol. 23, No. 13.

Nagy, J.I. et al., Coupling of Astrocyte Connexins Cx26, Cx30, Cx43 to Oligodendrocyte Cx29, Cx32, Cx47: Implications From Normal and Connexin32 Knockout Mice, Glia, 2003, pp. 205-218, vol. 44, No. 3.

Nisato, R.E. et al., Generation and Characterization of Telomerase-Transfected Human Lymphatic Endothelial Cells with an Extended Life Span, American Journal of Pathology, 2004, pp. 11-24, vol. 165, No. 1.

Odermatt, B. et al., Connexin 47 (Cx47)-Deficient Mice with Enhanced Green Flourescent Protein Reporter Gene Reveal Predominant Oligodendrocytic Expresion of Cx47 and Display Vacuolized Myelin in the CNS, The Journal of Neuroscience, 2003, pp. 4549-4559, vol. 23, No. 11.

Orthmann-Murphy, J.L. et al., Loss-of-function Connexin47 mutations cause Pelizaeus-Merzbacher-like disease, Mol. Cell Neurosci., 2007, pp. 629-641, vol. 34, No. 4.

Orthmann-Murphy, J.L. et al., Hereditary spastic paraplegia is a novel phenotype for GJA12/GJC2 mutations, Brain: A Journal of Neurology, 2009, pp. 426-438, vol. 132.

Ostergaard, P. et al., Rapid identification of mutations in GJC2 in primary lymphoedema using whole exome sequencing combined with linkage analysis with delineation of the phenotype, J Med Genet, 2011, pp. 251-255, vol. 48.

Poage, E. et al., Demystifying Lymphedema: Development of the Lymphedema Putting Evidence Into Practice Card, Clinical Journal of Oncology Nursing, 2008, pp. 951-964, vol. 12, No. 6.

Podgrabinska, S. et al., Molecular characterization of lymphatic endothelial cells, Proceedings of the National Academy of Sciences of the United States of America, 2002, pp. 16069-16074, vol. 99, No. 25.

Rhee, D.Y. et al., Connexin 43 regulates epicardial cell polarity and migration in coronary vascular development, Development, 2009, pp. 3185-3193, vol. 136.

Rhodin, J.A.G., Microscopic Anatomy of the Pulmonary Vascular Bed in the Cat Lung, Microvascular Research, 1978, pp. 169-193, vol. 15.

Rockson, S.G. et al., Estimating the Population Burden of Lymphedema, Annals of the New York Academy of Sciences, 2008, pp. 147-154, vol. 1131.

* cited by examiner

Protein (SEQ ID NO: 1, residues 4-439)

```
MSWSFLTRLL EEIHNHSTFV GKVWLTVLVV FRIVLTAVGG EAIYSDEQAK FTCNTRQPGC DNVCYDAFAP
LSHVRFWVFQ IVVISTPSVM YLGYAVHRLA RASEQERRRA LRRRPGPRRA PRAHLPPPHA GWPEPADLGE
EEPMLGLGEE EEEEETGAAE GAGEEAEEAG AEEACTKAVG ADGKAAGTPG PTGQHDGRRR IQREGLMRVY
VAQLVARAAF EVAFLVGQYL LYGFEVRPFF PCSRQPCPHV VDCFVSRPTE KTVFLLVMYV VSCLCLLLNL
CEMAHLGLGS AQDAVRGRRG PPASAPAPAP RPPPCAFPAA AAGLACPPDY SLVVRAAERA RAHDQNLANL
ALQALRDGAA AGDRDRDSSP CVGLPAASRG PPRAGAPASR TGSATSAGTV GEQGRPGTHE RPGAKPRAGS
EKGSASSRDG KTTVWI
```

*Fig. 1A* mRNA (SEQ ID NO: 2)

```
   1 ggggaacaat ggggcccttg agggcccctc ctccagcccc cattgtgctt ggtggtgaga
  61 ggtggccctg gctcggccac acaccctcgg ggaggaccag catccaagca ggtggaaggg
 121 ctctgaggga gactggaatt ttctggcctg gagaaggacc cgcccgcccg ccctatgac
 181 caacatgagc tggagcttcc tgacgcggct gctggaggag atccacaacC ACtccacctt
 241 cgtgggcaag gtgtggctca cggtgctggt ggtcttccgc atcgtgctga cggctgtggg
 301 cggcgaggcc atctacTCGg acgagcaggc caagttcact tgcaacacgc ggcagccagg
 361 ctgcgacaac gtctgctatg acgccttcgc gccctgtcg cacgtgcgct tctgggtctt
 421 ccagattgtg gtcatctcca cgccctcggt catgtacctg gctacgccg tgaccgcct
 481 ggcccgtgcg tctgagcagg agcggcgccg cgccctccgc cgccgccgg ggccacgccg
 541 cgcgcccCGA gcgcacctgc cgccccgca cgccggctgg cctgagcccg ccgacctggg
 601 cgaggaggag cccatgctgG GCctgggcga ggaggaggag gaggaggaga cggggcagc
 661 cgagggcgcc ggcgaggaag cggaggaggc aggcgcggag gaggcgtgca ctaaggcggt
 721 cggcgctgac GGCaaggcgg cagggacccc gggcccgacc gggcaacacg atgggcggag
 781 gcgcatccag cgggagggcc tgatgcgcgt gtacgtggcc cagctggtgg ccagggcagc
 841 tttcgaggtg gccttcctgg tgggccagta cctgctgtac ggcttcgagg tgcgaccgtt
 901 cttttccctgc agccgccagc cctgccgca cgtggtggac tgcttcgtgt cgCGCcctac
 961 tgaaaagacg gtcttcctgc tggttatgta cgtggtcagc tgcctgtgcc tgctgctcaa
1021 cctctgtgag atggcccacc tgggcttggg cagcgcgcag gacgcggtgc gcggccgccg
1081 cggccccccg gcctccgccc ccgcccccgc gccgcggccc CCGccctgcg ccttccctgc
1141 ggcggccgct ggcttggcct gcccgcccga ctacagcctg gtggtgcggg cggccgagcg
1201 cgctcgggcg catgaccaga acctggcaaa cctggccctg caggcgctgc gcgacggggc
1261 agcggctggg gaccgcgacc gggacagttc gccgtgcgtc ggcctccctg cggcctcccg
1321 ggggCCCccc agagcaggcg ccccccgcgtc ccggacgggc agtgctacct ctgcgggcac
1381 tgtcggggag cagggccggc ccggcaccCA Cgagcggcca ggagccaagc ccagggctgg
1441 ctccgagaag ggcagtgcca gcagcaggga cgggaagacc accgtgtgga tctgagggcg
1501 ctggcttgcg agctgggcca gggaggagga gggttggggg gctccggtgg aaacctgcga
1561 ccccttctcc tcagccttct ccttagccgg tggcctcagg cagactctgc ccagaggggc
1621 agccaggctg ctcagggaag gggctgaaag cggcagagga gtgccctggc ttggtcacca
1681 ctggggccaa ggtggggtgg agagaggcct aggagccaga aagggccctc tgctgtggtc
1741 tgaaccccag ggggagtggg gcattgactc caccctgtc ctgagctgga ataggtcctc
1801 tggatgcca gctctcccct ttgtgcttcc ctgcagcaac ccatggaggg cccagggtgc
1861 ctggtatggg catcagttgg tgggggtgcg ggggtgcgtg tccccattcc ctgcaacagc
1921 aaatgggct ccttcttcag ccctcccctt cccagcccca aactgagaca gactgggagc
```

*Fig. 1B-1*

```
1981 tgggagcctg gggtggacag gaccataccc tctttgagct tctgcgatgc cggccttccg
2041 ttcctctggg aggcttgaag ttctgcaaag atgttgatat gccttgcagc ttggacccaa
2101 tgggtggtgg tcagggcctg ggggcttggc catgctgggg gaatggggct ctgggttcct
2161 gcctgtggcc tgtctgtcct cctccctaat tcagacccag cctcaagagg aaagggagta
2221 aaataaaact aacttgttta taaaaaaaa aaaaaaaa
```

*Fig. 1B-2*

Protein (SEQ ID NO: 3)

MGDWGFLEKL LDQVQEHSTV VGKIWLTVLF IFRILILGLA GESVWGDEQS DFECNTAQPG CINVCYDQAF
PISHIRYWVL QFLFVSTPTL VYLGHVIYLS RREERLRQKE GELRALPAKD PQVERALAAV ERQMAKISVA
EDGRLRIRGA LMGTYVASVL CKSVLEAGFL YGQWRLYGWT MEPVFVCQRA PCPYLVDCFV SRPTEKTIFI
IFMLVVGLIS LVLNLLELVH LLCRCLSRGM RARQGQDAPP TQGTSSDPYT DQVFFYLPVG QGPSSPPCPT
YNGLSSSEQN WANLTTEERL ASSRPPLFLD PPPQNGQKPP SRPSSSASKK QYV

*Fig. 2A* mRNA (SEQ ID NO: 4)

```
   1 cagcagggct ccgcgggcg tcactccggc catcgtcccc acctccacct gggccgcccg
  61 gcaggcaggc gacggaggcc cggagccat gggtgactgg ggcttcctgg agaagttgct
 121 ggaccaggtc caggagcact cgaccgtggt gggtaagatc tggctgacgg tgctcttcat
 181 cttccgcatc ctcatcctgg gcctggccgg cgagtcagtg tggggtgacg agcaatcaga
 241 tttcgagtgt aacacggccc agccaggctg caccaacgtc tgctatgacc aggccttccc
 301 catctcccac atccgctact gggtgctgca gttcctcttc gtcagcacac ccaccctggt
 361 ctacctgggc catgtcattt acctgtctcg gcgagaagag cggctgcggc agaaggaggg
 421 ggagctgcgg gcactgccgg ccaaggaccc acaggtggag cgggcgctgg cggccgtaga
 481 gcgtcagatg gccaagatct cggtggcaga gatggtcgc ctgcgcatcc gcggagcact
 541 gatgggcacc tatgtcgcca gtgtgctctg caagagtgtg ctagaggcag gcttcctcta
 601 tggccagtgg cgcctgtacg gctggaccat ggagcccgtg tttgtgtgcc agcgagcacc
 661 ctgcccctac ctcgtggact gctttgtctc tcgccccacg gagaagacca tcttcatcat
 721 cttcatgttg gtggttggac tcatctccct ggtgcttaac ctgctggagt tggtgcacct
 781 gctgtgtcgc tgcctcagcc gggggatgag ggcacggcaa ggccaagacg caccccgac
 841 ccagggcacc tcctcagacc cttacacgga ccaggtcttc ttctacctcc ccgtgggcca
 901 ggggccctca tccccaccat gccccaccta caatgggctc tcatccagtg agcagaactg
 961 ggccaacctg accacagagg agaggctggc gtcttccagg cccctctct cctggaccc
1021 accccctcag aatggccaaa acccccaag tcgtcccagc agctctgctt ctaagaagca
1081 gtatgtatag aggcctgtgg cttatgtcac ccaacagagg ggtcctgaga agtctggctg
1141 cctgggatgc cccctgcccc ctcctggaag gctctgcaga gatgactggg ctggggaagc
1201 aggtgcttgc tggccatgga gcctcattgc aagttgttct tgaacacctg aggccttcct
1261 ggtgcccacc aggcactacg gcttcctctc cagaatgtgg ctttgcctga gcacagacag
1321 agtcagcatg gaatgctctt ggccaagggt actgggggcc ctctggcctt ttgcagctga
1381 tccagaggaa cccagagcca acttacccca acctcaccct atggaacagt cacctgtgcg
1441 caggttgtcc tcaaaccctc tcctcacagg aaaaggcgga ttgaggctgc tgggtcagcc
```

*Fig. 2B-2*

```
1501 ttgatcgcac agacagagct tgtgccggat ttggccctgt caagggact ggtgccttgt
1561 tttcatcact ccttcctagt tctactgttc aagcttctga aataaacagg acttgatcac
1621 aaaaaaaaaa aaaaaaaaaa aaaaaaaaaa aaaaaaaaaa aaaaaaaaaa aaaaaaaaaa
1681 aaaaaaaaaa aaaaaaaaaa aaaaaaaaa
```

*Fig. 2B-1*

Protein (SEQ ID NO: 5)

```
MGDWSALGKL LDKVQAYSTA GGKVWLSVLF IFRILLLGTA VESAWGDEQS AFRCNTQQPG CENVCYDKSF
PISHVRFWVL QIIFVSVPTL LYLAHVFYVM RKEEKLNKKE EELKVAQTDG VNVDMHLKQI EIKKFKYGIE
EHGKVKMRGG LLRTYIISIL FKSIFEVAFL LIQWYIYGFS LSAVYTCKRD PCPHQVDCFL SRPTEKTIFI
IFMLVVSLVS LALNIIELFY VFFKGVKDRV KGKSDPYHAT SGALSPAKDC GSQKYAYFNG CSSPTAPLSP
MSPPGYKLVT GDRNNSSCRN YNKQASEQNW ANYSAEQNRM GQAGSTISNS HAQPFDFPDD NQNSKKLAAG
HELQPLAIVD QRPSSRASSR ASSRPRPDDL EI
```

*Fig. 3A* mRNA (SEQ ID NO: 6)

```
   1 gagtcagtgg cttgaaactt taaaagctc tgtgctccaa gttacaaaaa agcttttacg
  61 aggtatcagc acttttcttt cattagggggg aaggcgtgag gaaagtacca aacagcagcg
 121 gagttttaaa ctttaaatag acaggtctga gtgcctgaac ttgccttttc attttacttc
 181 atcctccaag gagttcaatc acttggcgtg acttcactac ttttaagcaa aagagtggtg
 241 cccaggcaac atgggtgact ggagcgcctt aggcaaactc cttgacaagg ttcaagccta
 301 ctcaactgct ggagggaagg tgtggctgtc agtacttttc attttccgaa tcctgctgct
 361 ggggacagcg gttgagtcag cctggggaga tgagcagtct gcctttcgtt gtaacactca
 421 gcaacctggt tgtgaaaatg tctgctatga caagtctttc ccaatctctc atgtgcgctt
 481 ctgggtcctg cagatcatat ttgtgtctgt acccacactc ttgtacctgg ctcatgtgtt
 541 ctatgtgatg cgaaaggaag agaaactgaa caagaaagag gaagaactca aggttgccca
 601 aactgatggt gtcaatgtgg acatgcactt gaagcagatt gagataaaga gttcaagta
 661 cggtattgaa gagcatggta aggtgaaaat gcgaggggggg ttgctgcgaa cctacatcat
 721 cagtatcctc ttcaagtcta tctttgaggt ggccttcttg ctgatccagt ggtacatcta
 781 tggattcagc ttgagtgctg tttacacttg caaaagagat ccctgcccac atcaggtgga
 841 ctgtttcctc tctcgcccca cggagaaaac catcttcatc atcttcatgc tggtggtgtc
 901 cttggtgtcc ctggccttga atatcattga actcttctat gttttcttca agggcgttaa
 961 ggatcgggtt aagggaaaga gcgacccttta ccatgcgacc agtggtgcgc tgagccctgc
1021 caaagactgt gggtctcaaa aatatgctta tttcaatggc tgctcctcac caaccgctcc
1081 cctctcgcct atgtctcctc ctgggtacaa gctggttact ggcgacagaa acaattcttc
1141 ttgccgcaat acaacaagc aagcaagtga gcaaaactgg ctaattaca gtgcagaaca
1201 aaatcgaatg gggcaggcgg gaagcaccat ctctaactcc catgcacagc cttttgattt
1261 ccccgatgat aaccagaatt ctaaaaaact agctgctgga catgaattac agccactagc
```

*Fig. 3B-1*

```
1321 cattgtggac cagcgacctt caagcagagc cagcagtcgt gccagcagca gacctcggcc
1381 tgatgacctg gagatctaga tacaggcttg aaagcatcaa gattccactc aattgtggag
1441 aagaaaaaag gtgctgtaga aagtgcacca ggtgttaatt ttgatccggt ggaggtggta
1501 ctcaacagcc ttattcatga ggcttagaaa acacaaagac attagaatac ctaggttcac
1561 tggggtgta tgggtagat gggtggagag ggagggata agagaggtgc atgttggtat
1621 ttaaagtagt ggattcaaag aacttagatt ataaataaga gttccattag gtgatacata
1681 gataagggct ttttctcccc gcaaacaccc ctaagaatgg ttctgtgtat gtgaatgagc
1741 gggtggtaat tgtggctaaa tattttttgtt ttaccaagaa actgaaataa ttctggccag
1801 gaataaatac ttcctgaaca tcttaggtct tttcaacaag aaaagacag aggattgtcc
1861 ttaagtccct gctaaaacat tccattgtta aaatttgcac tttgaaggta agctttctag
1921 gcctgacct ccaggtgtca atggacttgt gctactatat ttttttattc ttggtatcag
1981 tttaaaattc agacaaggcc cacagaataa gatttcctt gcatttgcaa atacgtatat
2041 tcttttttcca tccacttgca caatatcatt accatcactt tttcatcatt cctcagctac
2101 tactcacatt catttaatgg tttctgtaaa cattttaag acagttggga tgtcacttaa
2161 cattttttt ttgagctaaa gtcagggaat caagccatgc ttaatattta acaatcactt
2221 atatgtgtgt cgaagagttt gtttttgtttg tcatgtattg gtacaagcag atacagtata
2281 aactcacaaa cacagatttg aaaataatgc acatatggtg ttcaaatttg aacctttctc
2341 atggattttt gtggtgtggg ccaatatggt gtttacatta tataattcct gctgtggcaa
2401 gtaaagcaca ctttttttt ctcctaaaat gtttttccct gtgtatccta ttatggatac
2461 tggttttgtt aattatgatt ctttatttttc tctccttttt ttaggatata gcagtaatgc
2521 tattactgaa atgaatttcc ttttctgaa atgtaatcat tgatgcttga atgatagaat
2581 tttagtactg taaacaggct ttagtcatta atgtgagaga cttagaaaaa atgcttagag
2641 tggactatta aatgtgccta atgaatttt gcagtaactg gtattcttgg gttttcctac
2701 ttaatacaca gtaattcaga acttgtattc tattatgagt ttagcagtct tttggagtga
2761 ccagcaactt tgatgtttgc actaagattt tatttggaat gcaagagagg ttgaaagagg
2821 attcagtagt acacatacaa ctaatttatt tgaactatat gttgaagaca tctaccagtt
2881 tctccaaatg cctttttaa aactcatcac agaagattgg tgaaaatgct gagtatgaca
2941 cttttcttct gcatgcatg tcagctacat aaacagtttt gtacaatgaa aattactaat
3001 ttgtttgaca ttccatgtta aactacggtc atgttcagct tcattgcatg taatgtagac
3061 ctagtccatc agatcatgtg ttctggagag tgttctttat tcaataaagt tttaatttag
3121 tataaacata
```

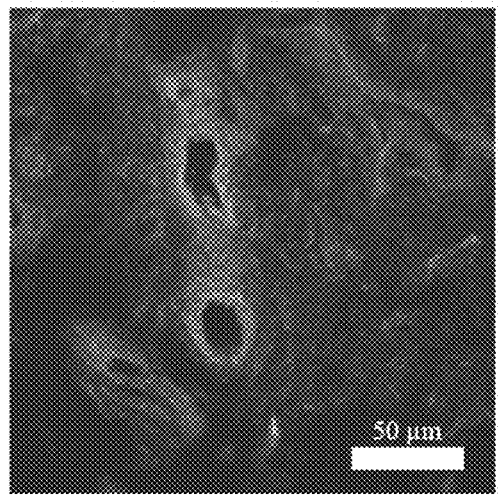
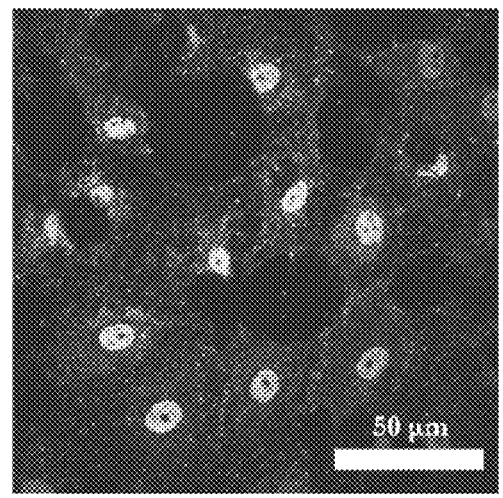
*Fig. 6A*  *Fig. 6B*
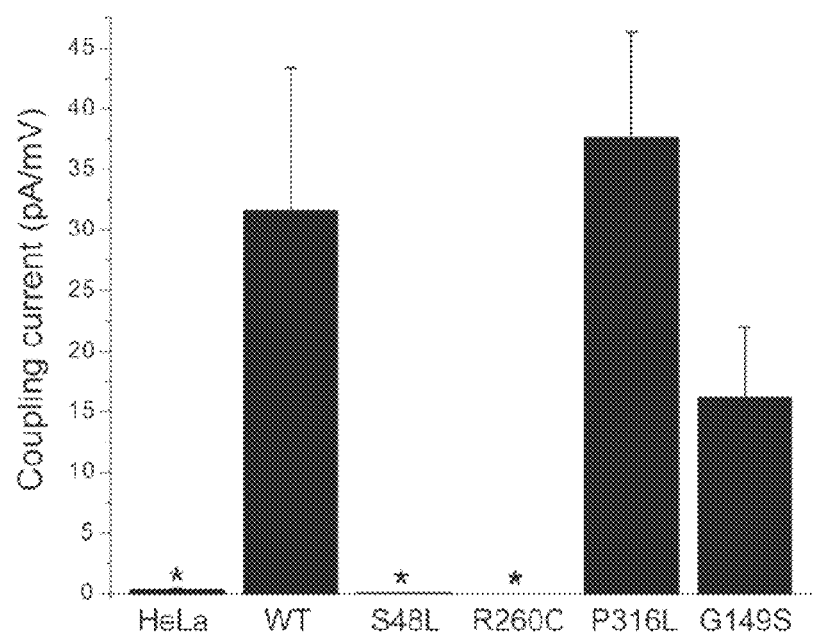
*Fig. 6C*

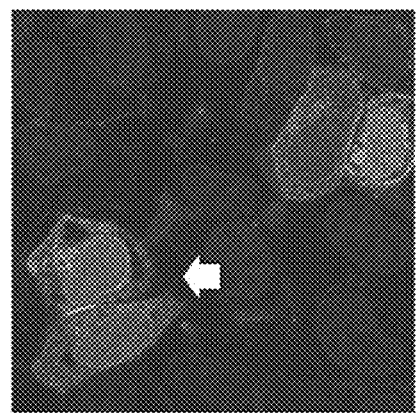 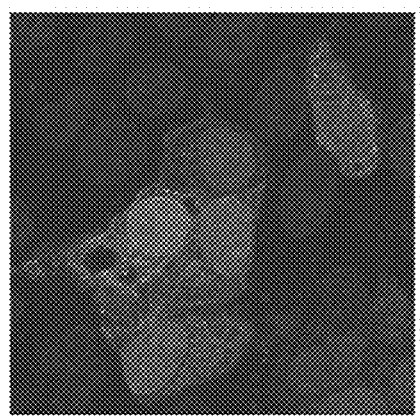
Fig. 7A    Fig. 7B
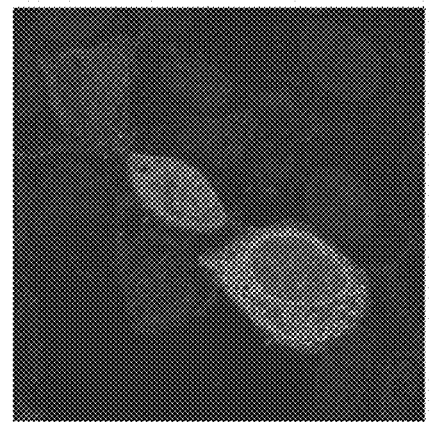
Fig. 7C

Protein (SEQ ID NO: 7)

```
MGDWSFLGNF LEEVHKHSTV VGKVWLTVLF IFRMLVLGTA AESSWGDEQA DFRCDTIQPG CQNVCYDQAF
PISHIRYWVL QIIFVSTPSL VYMGHAMHTV RMQEKRKLRE AERAKEVRGS GSYEYPVAEK AELSCWEEGN
GRIALQGTLL NTYVCSILIR TTMEVGFIVG QYFIYGIFLT TLHVCRRSPC PHPVNCYVSR PTEKNVFIVF
MLAVAALSLL LSLAELYHLG WKKIRQRFVK PRQHMAKCQL SGPSVGIVQS CTPPPDFNQC LENGPGGKFF
NPFSNNMASQ QNTDNLVTEQ VRGQEQTPGE GFIQVRYGQK PEVPNGVSPG HRLPHGYHSD KRRLSKASSK
ARSDDLSV
```

*Fig. 13A* mRNA (SEQ ID NO: 8)

```
   1 attaaaaaga cggtggaaga ggaacaactg acaggctcaa gagcaaaaag cgtgggcagt
  61 tggagaagaa gcagccagag tgtgaagaag cccacggaag gaaagtccag ggaggaggaa
 121 aagaagcaga agtttggca tctgttccct ggctgtgcca agatgggcga ttggagcttc
 181 ctgggaaatt tcctggagga agtacacaag cactcgaccg tggtaggcaa ggtctggctc
 241 actgtcctct tcatattccg tatgctcgtg ctgggcacag ctgctgagtc ttcctggggg
 301 gatgagcagg ctgatttccg gtgtgatacg attcagcctg gctgccagaa tgtctgctac
 361 gaccaggctt tccccatctc ccacattcgc tactgggtgc tgcagatcat cttcgtctcc
 421 acgccctctc tggtgtacat gggccacgcc atgcacactg tgcgcatgca ggagaagcgc
 481 aagctacggg aggccgagag ggccaaagag gtccggggct ctggctctta cgagtacccg
 541 gtggcagaga aggcagaact gtcctgctgg gaggaaggga atggaaggat tgccctccag
 601 ggcactctgc tcaacaccta tgtgtgcagc atcctgatcc gcaccaccat ggaggtgggc
 661 ttcattgtgg gccagtactt catctacgga atcttcctga ccaccctgca tgtctgccgc
 721 aggagtccct gtccccaccc ggtcaactgt tacgtatccc ggcccacaga aaagaatgtc
 781 ttcattgtct ttatgctggc tgtggctgca ctgtccctcc tcttagcct ggctgaactc
 841 taccacctgg gctggaagaa gatcagacag cgatttgtca accgcggca gcacatggct
 901 aagtgccagc tttctggccc ctctgtgggc atagtccaga gctgcacacc acccccgac
 961 tttaatcagt gcctggagaa tggccctggg ggaaaattct caatcccctt cagcaataat
1021 atggcctccc aacaaaacac agacaacctg gtcaccgagc aagtacgagg tcaggagcag
1081 actcctgggg aaggtttcat ccaggttcgt tatggccaga agcctgaggt gcccaatgga
1141 gtctcaccag gtcaccgcct tccccatggc tatcatagtg acaagcgacg tcttagtaag
1201 gccagcagca aggcaaggtc agatgaccta tcagtgtgac cctcctttat gggaggatca
1261 ggaccaggtg ggaacaaagg aggctcagag aagaagacg tgtcccttct gaactgatgc
```

*Fig. 13B-1*

```
1321  tttctcactg tcatcactgc ttggctcctt tgagccccgg gtctcaatga cgttgctcat
1381  taattctaga aactataacc agggctctgg gatagtaaga gaggtgacaa cccacccaga
1441  ctgcagttcc ctccccaccc tctacccagt atacgaagcc tttcagatta ctcatgaaac
1501  agggtagagg gaaagaaggg aagcatggca aaagctggcc tggaagggat agccagaggg
1561  atagaatgac tctctctcta cataccagca gcataccaaa tgcgttctct aagttcctac
1621  ctccttgacc tgatcaccct ccctcctcca aggaagagct caaagttccc agccaataga
1681  cagcatgaat caaggaactt gcattatatg tgctcttgaa tctgttgtct ccatggacca
1741  ttcctcggag tagtggtgag atggccttgg gttgcccttg gcttctcctc cctctactca
1801  gccttaaaaa gggcttcttg gaactttacc agcagcctca gctttacaaa tgccttggta
1861  tgtacctctg gcaaatgccc caccttggtg atgttgcaac ctttccttct gctagggtgt
1921  acacctagcc tgtgcaggtg tcagccctgc tagggagtca ctgtacacac aaactctact
1981  ggaattcctg ccaacatctg tcaccctgca gctcctttac agttcaatcc aatgatagaa
2041  accatccctt ccctttctcc cttggctgtt cacccagcca ttccctgaag gccttaccaa
2101  caggaatatc caagaagctg ttgtcccctc tcgaaccctg accagatcat cagccactga
2161  ggccagtgga atttccccag gccttgttaa acaaagaaa gcattgtacc tctcagattc
2221  cccttgtgga aaaaaaatt ctgctgtgaa gatgaaaata aaaatggaga gaaacactg
2281  gaaactatt ttcccctcct atttacttcc tttgctgact gccaacttag tgccaagagg
2341  aggtgtgatg acagctatgg aggccccag atctctctct cctggaggct ttagcagggg
2401  caaggaaata gtagggaat ctccagctct cttggcaggg cctttatta aagagcgcag
2461  agattcctat gtctccctag tgccctaat gagactgcca gtgggggct gtagaaaagc
2521  cttgccttcc ccaggattg gcctggtctc tgtattcact ggatccataa tgggttgctg
2581  ttgttttgga tgaaggtaaa cgatgcttgg aattggaaac tgagacttat agagggatta
2641  ttacattatt aaaatgcacg tgtgtgtgtg tgtgggtgct gatgggatgg gtaaaggctt
2701  ggggagtcct gaaataagga aaggaaacca cagagaaact tgtgtcttcc tgctctcctc
2761  tccggctgcc tggcagttat taacctaaac agatagccac aagaggttgg gacagaggag
2821  ggtaaaggct cagaaggagg ttcaacctct gactcacctg cccatctctg ggccctctgc
2881  tgacacttgg atgctattgt tgggtggaaa gataaatgag agtggagagg tggaggaaag
2941  tgactaggat gccatttagg aaggaatgtc tgatcatccc gggtccctgg aggggacacc
3001  ttttaatcta ttgcctagca ttaatatttt ctctccttct atctctgaaa tgttttatga
3061  aatgagtgtt cttgaattag aaattctgtg ggatcaatct ttgatggtga gggttttaga
3121  aggaaaaat atagtaaaat gtgtaatttg tcttaataaa atctatctct acatcta
```

*Fig. 13B-2*

CONNEXIN MUTATION DETECTION FOR LYMPHATIC VARIATION AND DISEASE

CROSS REFERENCE TO RELATED APPLICATIONS

This application claims the benefit under 35 U.S.C. §119 (e) to U.S. Provisional Patent Application No. 61/333,794, filed on May 12, 2010, which is incorporated herein by reference in its entirety.

STATEMENT REGARDING FEDERAL FUNDING

This invention was made with government support under Grant No. HD037243, awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is ConnexinSEQID_ST25.txt. The size of the text file is 49,330 bytes, and the text file was created on Sep. 28, 2011.

Lymphedema is the abnormal accumulation of lymphatic fluid in interstitial space. Patients with lymphedema suffer from recurrent local infections, physical impairment, and cosmetic and psychosocial stigmatization and may be at increased risk for developing lymphangiosarcoma. The population prevalence of lymphedema is estimated in the range of 1.3-1.4 per 1000. Primary (inherited) lymphedema is less common than secondary lymphedema, which is associated with conditions such as filariasis, trauma, and cancer therapy. Recent studies in families with inherited forms of lymphedema have identified six genes, FLT43, (encoding VEGFR3; Karkkainen, M. J., et al. (2000). Missense mutations interfere with VEGFR-3 signalling in primary lymphoedema. Nat. Genet. 25, 153-159) (MIM 153100), FOXC25, (MIM 153400 and Finegold, D. N., et al. (2001). Truncating mutations in FOXC2 cause multiple lymphedema syndromes. Hum. Mol. Genet. 10, 1185-1189), SOX18 (MIM 607823 and Irrthum, A., et al. (2003). Mutations in the transcription factor gene SOX18 underlie recessive and dominant forms of hypotrichosis-lymphedema-telangiectasia. Am. J. Hum. Genet. 72, 1470-1478), HGF (MIM 142409 and Finegold, D. N., et al. (2008). HGF and MET mutations in primary and secondary lymphedema. Lymphat. Res. Biol. 6, 65-68), MET (MIM 164860 and Finegold, D. N., et al. (2008). Lymphat. Res. Biol. 6, 65-68), and CCBE1 (MIM 235510; Alders, M., et al. (2009). Mutations in CCBE1 cause generalized lymph vessel dysplasia in humans. Nat. Genet. 41, 1272-1274 and Connell, F., et al. Lymphoedema Consortium. (2010). Linkage and sequence analysis indicate that CCBE1 is mutated in recessively inherited generalized lymphatic dysplasia. Hum. Genet. 127, 231-241), causing lymphedema.

Gap junctions were identified in the 1960s, but it was not until almost 20 years later that Connexins were identified as the major protein constituent of these complexes. There are at least 21 different human Cx proteins; all form hexameric pores through the plasma membrane and typically align with a corresponding connexon (i.e., hemichannel) on an adjacent cell membrane. Cx nomenclature is varied: proteins are named based on their molecular weight in kD or based on the genes uniquely expressing Cxs. There is increasing documentation of functional hemichannels, heterogeneity of Cx proteins within and between connexons, and heterocellular coupling, demonstrating the complexity and variability of the organization of a gap junction complex.

While gap junctions are present in most mammalian cells, and are well studied in certain cell types, especially cardiac myocytes, vascular smooth muscle cells, and cells in the CNS, understanding of the function and regulation of these structures is still expanding.

Gap junction intercellular communication allows for the transport of small metabolites, $Ca^{2+}$, ATP, etc., with an estimated size limitation of 1000 daltons. Regulation of channels' open probability and selective permeability may be Cx specific but may also be mediated by factors such as pH, phosphorylation of Cx residues, ischemia, voltage and intracellular $Ca^{2+}$ levels.

SUMMARY

Described herein are methods of identifying (determining, etc.) relative risk of development of lymphedema in a human. Patients having functional mutations in connexins 37, 40, and 47, encoded by GJA4, GJA5 and GJC2, respectively, have an increased risk of development of lymphedema as compared to patients with wild-type alleles. Functional mutations of Cx47 include the mis sense mutations identified as: S45L (wild-type Serine amino acid residue at position 45 of SEQ ID NO: 1 is replaced by a Leucine residue), H16P, R122Q, G146S, G183C, R257c, P313L, P381S and H409Y of SEQ ID NO: 1. In the Examples below, these result from single nucleotide polymorphisms that alter the wild-type codon, including, in reference to the sequence presented as SEQ ID NO: 2: 436G>A (wild-type guanine at +436 in relation to the first base of the start codon (+1) and which also can be alternately recited as position 620 of SEQ ID NO: 2, is replaced with an adenine, resulting in a change of the codon for Glycine (GGC) to a codon for Serine (AGC)), resulting in the G146S substitution; a 547G>T, resulting in the G183C substitution; 1141C>T, resulting in the P381S substitution; or 1225C>T, resulting in the H409Y substitution.

This is an extremely novel finding as virtually nothing is known about cell-cell interaction with regard to the lymphatic endothelial cell, and the Connexin 47 mutations previously found in patients have been associated with a neurological phenotype, Pelizaeus-Merzbacher Disease. Connexins appear to be a major reservoir of mutations in individuals with primary lymphedema as well as individual suffering from secondary lymphedema. Comprehensive genetic sequencing of the Connexin genes including the 5' upstream regions and the 3' downstream regions will offer a specific mutational diagnosis to many individual suffering from primary and secondary lymphedema.

Provided therefore is a method of identifying risk of developing lymphedema, in a human patient. The method comprises identifying in a sample obtained from the patient the presence of or absence of a polymorphism in one or both alleles of one of GJA4, GJA5, and GJC2, where the presence of a wild-type allele is indicative of a lower relative risk of lymphedema and the presence of the mutant allele is indicative of a higher relative risk of lymphedema as compared to the presence of the wild-type allele. The mutant allele typically encodes a functional mutation of Cx37, Cx40 or Cx47. In one embodiment, the mutant allele (e.g., the functional mutation) is dominant. In one embodiment, the method comprises identifying the presence of or absence of a polymorphism in one or both alleles of GJC2 in the patient that is associated with increased or decreased risk of lymphedema in a patient. According to certain embodiments, the mutant allele encodes one or more of H16P, S45L, R122Q, G146S, G183C, R257c, P313L, P381S and H409Y substitutions in Cx47 (SEQ ID NO: 1). Examples of polymorphisms that result in these mutant alleles include: a C to T transversion at nucleotide 953 of SEQ ID NO: 2, resulting in the R257c substitution; a C to T transversion at nucleotide 318 of SEQ ID NO: 2, resulting in the S45L substitution and a polymorphism selected from the group consisting of 620G>A, 731G>T, 1325C>T, 1409C>T, 318C>T, 953C>T, 549G>A, 231A>C and 1122C>T of SEQ ID NO: 2. The lymphedema can be primary or secondary lymphedema. In one non-limiting example, the lymphedema is secondary lymphedema following breast cancer treatment. Non-limiting examples of polymorphisms identified in connection with secondary lymphedema following breast cancer treatment include polymorphisms resulting in G146S, G183C, P381S and H409Y substitutions in Cx47 (SEQ ID NO: 1). According to one non-limiting embodiment, the non-functional mutation of Cx47 associated with secondary lymphedema does not result in a difference between the mutant Cx47 and wild type Cx47 in a plaque assay. Functional mutations in connexins, including in Cx47/GJC2 include mutations that result in differences between the mutant Cx47 and wild type Cx47 in one or more functional assay including a plaque assay, an electric coupling assay, a wound assay and a dye spread assay.

Also provided is a method of identifying a polymorphism that is associated with risk of development of lymphedema in a patient. The method comprises: determining the presence of a polymorphism in one or more of GJA4, GJA5 and GJC2 in a lymphedema patient, and determining if the mutant allele of the GJA4, GJA5 and GJC2 gene is a functional mutation of one or more of Cx37, Cx40 and Cx47 as compared to a wild type allele using one or more of a plaque assay, an electric coupling assay, a wound assay and a dye spread assay.

BRIEF DESCRIPTION OF THE DRAWINGS

FIGS. 1A and 1B, respectively, are exemplary amino acid (SEQ ID NO: 1, residues 4-439) and cDNA (SEQ ID NO: 2) sequences for Cx47 (GenBank Accession No. NM_020435). Codons corresponding to polymorphisms H16P, S45L, R122Q, G146S, G183C, R257C, P313L, P381S and H409Y are emphasized.

FIGS. 2A and 2B, respectively, are exemplary amino acid (SEQ ID NO: 3) and cDNA (SEQ ID NO: 4) sequences for Cx37 (GenBank Accession No. NM_002060).

FIGS. 3A and 3B, respectively, are exemplary amino acid (SEQ ID NO: 5) and cDNA (SEQ ID NO: 6) sequences for Cx43 (GenBank Accession No. NM_000165).

FIG. 5. Amino Acid Alignment of Cx47 from Different Species (human, SEQ ID NO: 1; chimpanzee, SEQ ID NO: 21; cow, SEQ ID NO: 22; mouse, SEQ ID NO: 23; and rat, SEQ ID NO: 24). Light gray indicates intracellular domains; dark gray indicates transmembrane domains; white indicates extracellular domains. Dots represent the positions of amino acids altered in lymphedema families in this example.

FIG. 12C Immunofluorescent confocal microscopy reveals Cx47 intercellular plaques in near confluent HeLa cells transfected with WT-hCx47-EGFP (A), and mutants: G146S(C), G183C (D), P381S (E), and H409Y (F). No plaques are seen in untransfected HeLa cells (B). White arrow head indicates sample plaques in WT-hCx47-EGFP expressing cells (A). Green indicative of EGFP and transfection, red Cx47, and blue nuclei. Scale bar, 10 μm.

FIGS. 13A and 13B, respectively, are exemplary amino acid (SEQ ID NO: 7) and cDNA (SEQ ID NO: 8) sequences for Cx40 (GenBank Accession No. NM_002060, MIM *121013).

DETAILED DESCRIPTION

Figures 1, 4:
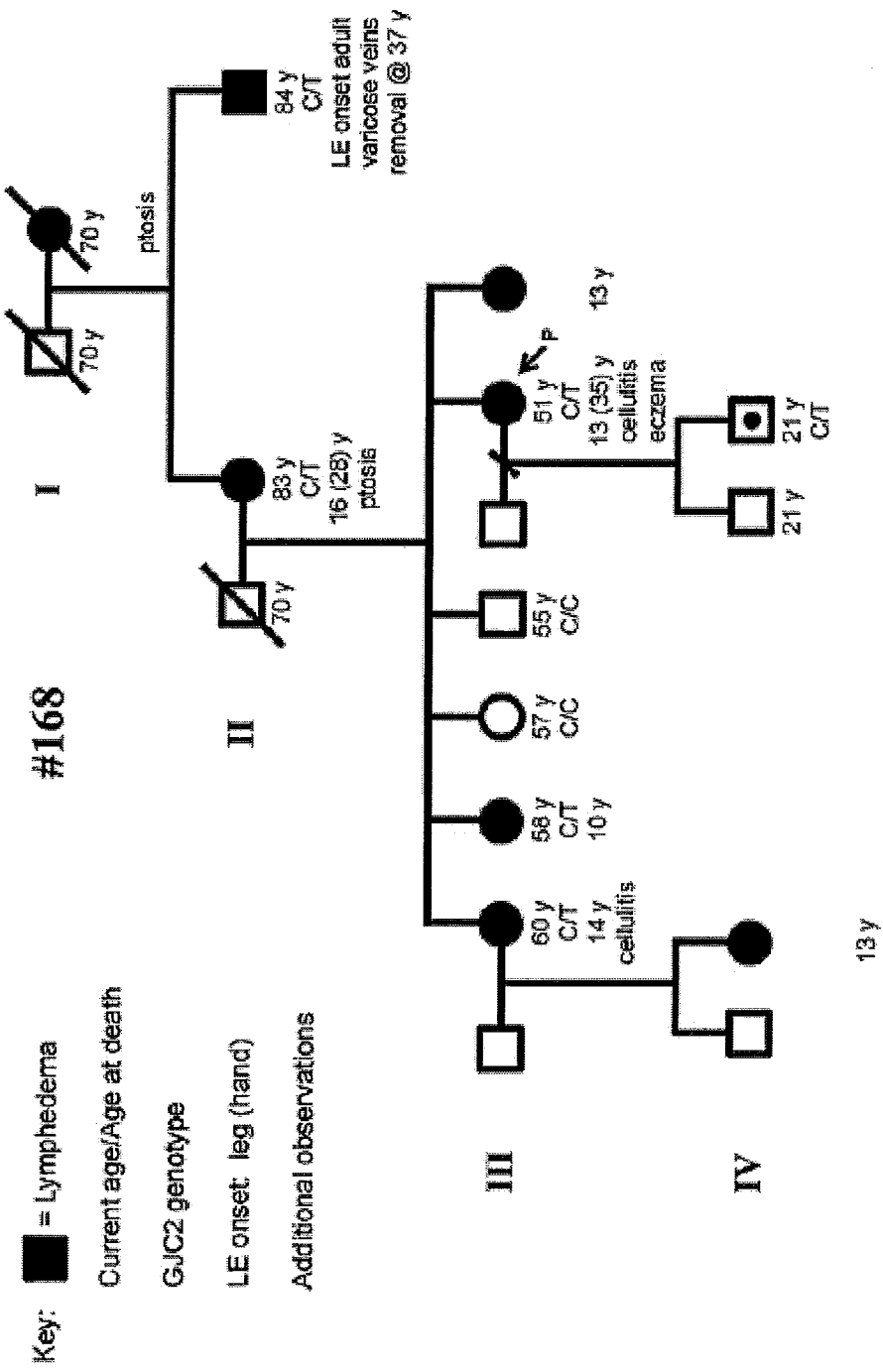
FIG. 4. Pedigrees of the Two Linked Families Pedigrees of the two linked families showing current age or age at death, cosegregation of GJC2 missense mutation with lymphedema, age at onset of lymphedema of the leg and/or hand, and other phenotypic features. Family 168, R257c (identified as R260c), and family 135, S45L, are shown. Filled shapes indicate affected individuals with lymphedema. LOD=6.5. Arrows indicates the probands.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

For convenience, all polymorphisms described in the claims are in reference to published sequences that are publically available from GenBank. For instance, for GJC2/Cx47, reference is made to GenBank Accession No. NM_020435, presented herein as SEQ ID NO: 1 (protein) and SEQ ID NO: 2 (mRNA)). The nucleotide and protein sequences provided herein are exemplary and are used to represent and identify nucleotide and protein sequences, as well as to describe polymorphisms, as they exist in the human population. The sequences are presented herein are not intended to be limiting.

A patient is a mammal, including humans, and does not imply any doctor-patient relationship or any other relationship.

An allele is one of two or more forms of a gene. The sequence differences in genes between two alleles are polymorphisms, which can be single-nucleotide (SNP) or can involve multiple bases. Wild-type is the most prevalent allele in a population (e.g., of humans) and is considered "normal." A mutation is a change in a genetic code (nucleotide sequence or genomic sequence) that differs from wild-type. Mutations include somatic and germ-line mutations. Mutations include insertions, deletions and substitutions of one or more nucleotide in a nucleotide sequence, and can result in alteration of a protein sequence, depending on the nature of the mutation. A mutation may be silent, meaning that it has no discernable physiological effect. A mutation also can be functional, meaning it has some physiological effect; either a loss or gain of a particular function. Mutations include: missense, frameshift, nonsense (stop, truncation), deletion, insertions, inversions, etc. An allele (version of a gene, for example w.t. or mutated) can be recessive or dominant. In the case of a dominant mutation (e.g., a dominant autosomal mutation, as described below), only one allele is needed to exhibit the physiological effects of the mutation. In the case of connexins and their role in lymphedema, the mutant alleles appear to be autosomal dominant, but in some instances, may act as a recessive.

A functional mutation is a mutation that results in loss or gain of function of a protein when compared to wild-type. With respect to connexins, a mutation is deemed to be functional by an increase or decrease in any function attributable to the connexin, and preferably related to the function of the connexin in lymphatic tissue. For example, as indicated below, four assays are described for determining connexin function, including a plaque assay, an electric coupling assay, a wound assay and a dye spread assay, examples of which are described in the examples below. Presence of altered functionality of the connexin when a mutation is present is indicative of its suitability as a marker for determining risk of development of lymphedema. It should be noted that cloning of connexin, such as Cx47 mutations, such as in testing point mutations, is routine (as demonstrated herein), and determining alteration of functionality using the described assays is well within the skill of one of ordinary skill in the art and is not considered to be undue experimentation.

Small insertions and deletions and more typically missense mutations are good candidates as dominant mutant alleles. A number of single nucleotide missense polymorphisms have been documented in connection with connexins 37, 40 and 47. Missense mutations of evolutionary-conserved amino acids are suitable candidates, as they are expected to have a function in the protein. For example, in the alignment of FIG. 5, a mis sense mutation of any amino acid residue that is conserved in all species, or if only two amino acids are present in that position across species, would be expected to alter function of Cx47, and be indicative of increased risk of developing lymphedema. Mutations of any of the SRPTEK residues (e.g., amino acids 256-261 of SEQ ID NO: 2), would be expected to alter function of Cx47 or other connexins and be indicative of increased risk of developing lymphedema.

The risk of developing lymphedema in an individual having one particular set of connexin alleles is a relative risk as compared to the risk of developing lymphedema with a different set of alleles. Therefore, increased risk of developing lymphedema is associated with the presence of one (heterozygous) or two (homozygous) alleles of a mutation as compared to risk associated with homozygous wild-type. Decreased risk also is relative and is in the context of comparing homozygous wild-type (wt/wt) to heterozygous (m/wt) or homozygous (m/m) mutants. As indicated herein, the risk of developing lymphedema when a mutant allele is present is statistically significant and is at least 50% greater than in a wt/wt person, but in reality, given the mutations are not present in the controls, the risk is much higher in both heterozygous (m/wt) and homozygous (m/m) individuals.

Methods are provided for determining risk of developing lymphedema in a human patient. The methods comprise identifying in a sample obtained from the patient the presence of or absence of a polymorphism in one or both alleles of one of GJA4, GJA5 and GJC2, where the presence of a wild-type allele is indicative of a lower relative risk of lymphedema and the presence of the mutant allele is indicative of a higher relative risk of lymphedema as compared to the presence of the wild-type allele. The mutation may be homozygous or heterozygous, and within this class are any functional mutation of Cx37 (encoded by GJA4), Cx40 (encoded by GJA5) or Cx47 (encoded by GJC2). Examples of such functional mutations, in the context of Cx47, and with reference to the exemplary sequence provided in FIG. 1A (SEQ ID NO: 1, residues 4-439), include the missense mutations: H19P, S45L, R122Q, G146S, G183C, R257C, P313L, P381S and H409Y of SEQ ID NO: 1. In the Examples below, these all result from single nucleotide polymorphisms that alter the wild-type codon, including, in reference to SEQ ID NO: 2 (cDNA of the mRNA encoding Cx47): 436G>A (wild-type guanine at position 436 in relation to the start codon and base 620 of SEQ ID NO: 2 (FIG. 1B) is replaced with an adenine, resulting in a change of the codon for Glycine (GGC) to a codon for Serine (AGC)) resulting in the G146S substitution; a 547G>T, resulting in the G183C substitution; 1141C>T, resulting in the P381S substitution; or 1225C>T, resulting in the H409Y substitution. As indicated above, the mutations may be homozygous or heterozygous. For example, the sample may have the genotypes (alleles) C/T or T/T at base 1141 of SEQ ID NO: 2 (heterozygous or homozygous for the mutant allele "T" at base 1325 of SEQ ID NO: 2), T/C or T/T at base 1409 of SEQ ID NO: 2, T/G or T/T at base 731 of SEQ ID NO: 2, or A/G or A/A at base 620 of SEQ ID NO: 2 of SEQ ID NO: 2. Of note, due to codon degeneracy, more than one nucleotide changes may result in the same amino acid change. Also, it should be recognized that other amino acids may be substituted and would be expected to yield identical results. For example, while G146S is shown to yield the lymphedema phenotype, G146Xaa where Xaa can be any or all amino acids other than Gly (Xaa is any amino acid), are expected in most instances to disrupt function of the Cx47 protein (are expected to be functional mutations) because the mutated positions (e.g., H16, S45, R122, G146, G183, R257, P313, P381 and H409) are demonstrated to be functionally-sensitive positions in Cx47, indicating that H16Xaa, S45Xaa, R122Xaa, G146Xaa, G183Xaa, R257Xaa, P313Xaa, P381Xaa and H409Xaa missense mutations are expected to be indicative of increased risk of developing lymphedema. That said, single nucleotide polymorphisms (mutations) are more likely than multiple nucleotide polymorphisms within the same codon, so certain substitutions would be more likely to be identified than others.

The identity of a polymorphism that is linked to increased risk of lymphedema may be identified in any useful manner. As indicated herein, it is expected that further studies will identify additional candidate polymorphisms. Sequencing of the genes encoding connexins 37, 40 and 47 (GJA4, GJA5 and GJC2, respectively) in lymphedema patients are expected to identify additional polymorphisms linked to lymphedema risk. Methods of sequencing connexins GJA4, GJA5 and GJC2 are described herein and elsewhere. Known and heretofore unknown polymorphisms, for example polymorphisms identified in dbSNP or other public, broadly-available SNP databases, may be associated with risk of lymphedema by use of well-established population genetics statistical methods. Non-random association of one or more alleles with a connexin allele associated with lymphedema (by linkage or linkage disequilibrium) may be observed such that the identification of the non-connexin allele is sufficiently indicative of the presence of a functional mutation of a connexin.

As indicated elsewhere, the presence of a mutation (polymorphism) may be detected by any suitable assay. The methods described herein are broadly-known and in most cases, commercial kits are available to conduct the assay. In one embodiment, DNA or mRNA (e.g., via cDNA) in a sample from a patient is sequenced (resequenced) and the nucleotide sequence thus obtained is compared against a wild-type sequence (e.g., SEQ ID NOS: 2, 4, 6 and 8), and, if present, non-silent mutations located in the open reading frame (ORF) of the connexin gene, such as those identified herein, indicate an increased risk of development of lymphedema, especially when located in an evolutionarily-conserved amino acid, such as one of the SRPTEK residues (amino acids 256-261 of SEQ ID NO: 1, also present in Cx37 (amino acids 201-206 of SEQ ID NO: 3 (FIG. 2A), e.g., R202) and CxCx40 (amino acids 199-204 of SEQ ID NO: 7 (FIG. 13A), e.g., R200)). It is understood that as more connexin genes are resequenced in lymphedema patients, more polymorphisms associated with lymphedema will be identified. Other methods for identifying polymorphisms include: hybridization methods, such as molecular beacons, SNP microarrays, and dynamic allele-specific hybridization; enzymatic methods, such as restriction fragment length polymorphism (RFLP), PCR methods, primer extension methods (e.g., MassARRAY® iPLEX (Sequenom) and arrayed primer extension methods), oligonucleotide ligase methods, 5' nuclease (Taqman) and Flap endonuclease (Invader) methods; and other methods including single strand conformation polymorphism, temperature gradient gel electrophoresis, denaturing HPLC and high-resolution amplicon melting. Mutations can also be identified on the protein level by any useful method, such as by sequencing, ligand (e.g. antibody) binding methods, or even by testing tissue samples from a patient by nucleic acid hybridization, in situ staining, etc.

Example 1

To identify other causal genes for lymphedema, we reviewed differential gene expression in lymphatic endothelial cells (LECs) versus blood endothelial cells (BECs) and noted that GJA1 (encoding Cx 43) (MIM 121014) is expressed in BECs and LECs whereas GJC2 (encoding Cx47) (MIM608803) is expressed only in LECs (Wick, N., et al. (2007). Transcriptomal comparison of human dermal lymphatic endothelial cells ex vivo and in vitro. Physiol. Genomics 28, 179-192). Gap junctions are intercellular channels formed by hexamers of connexin proteins on adjoining cells that facilitate the electrical and metabolic coupling of cells within a tissue via a variety of mechanisms. Rhodin first suggested a role for gap junctions on lymphatic vessels, but there has been limited characterization of gap junction intercellular communication (GJIC) in lymphatic vessels or LECs (Rhodin, J. A. (1978). Microscopic anatomy of the pulmonary vascular bed in the cat lung. Microvasc. Res. 15, 169-193; Zawieja, D. C., et al. (1993). Distribution, propagation, and coordination of contractile activity in lymphatics. Am. J. Physiol. 264, H1283-H1291; and McHale, N. G., et al. (1992). Co-ordination of pumping in isolated bovine lymphatic vessels. J. Physiol. 450, 503-512).

We investigated the connexins as potential genes for causal lymphedema mutations in the families ascertained through the University of Pittsburgh Lymphedema Family Study (UPLFS). Initially, families were ascertained by a physician's diagnosis of lymphedema in the proband (confirmed by medical records) and a lymphedema occurrence in a first-degree relative. We screened 150 probands from the UPLFS for mutations in GJA1 (chromosome 6q22-q23), GJA4 (chromosome 1p35.1) (MIM 121012), and GJC2 (chromosome 1q41-q42). Sequences were aligned and curated with Sequencher v4.7 (Gene Codes Corp.). Mutations in FLT4, FOXC2, and SOX18, known lymphedema genes, were previously excluded in these probands by bidirectional sequence analysis. The sequences of GJA4 (NM002060), GJA1 (NM000165), and GJC2 (NM020435) were downloaded from Entrez Nucleotide. Unique sequence amplification and sequencing primers were designed to amplify genes in overlapping fragments. These fragments were then sequenced in both directions with ABI BigDye v3.1 chemistry, and the products were resolved on an ABI 3730 DNA sequencer in the Genomics and Proteomics Core Laboratory of the University of Pittsburgh. Six lymphedema families of mixed European ancestry were identified with heterozygous dominant causal GJC2 mutations (see, FIG. 4 and Table 1).

TABLE 1

GJC2 Mutations Observed in Primary Lymphedema Families

| Family | Sequence Substitution | Amino Acid Change | Predicted Domain |
|---|---|---|---|
| 337 | 47A > C | H16P | N-terminal |
| 135 | 134C > T | S45L | Extracellular loop 1 |
| 251 | 365G > A | R122Q | Intracellular loop |
| 104 | 436G > A | G146S | Intracellular loop |
| 168 | 769C > T | R257C | Extracellular loop 2 |
| 151 | 938C > T | P313L | C-terminal |

We identified two GJC2 mutations in families suitable for linkage analysis: one cosegregating lymphedema and a C>T transition at nucleotide +134 (134C>T) leading to an S45L (family 135) substitution in extracellular loop 1 of Cx47, and another cosegregating lymphedema and a C>T transition at nucleotide +769 (769C>T) resulting in an R257c (family 168) substitution in extracellular loop 2. Linkage analysis in these two families yielded a LOD score of 6.5 under a model of disease frequency=0.0001, penetrance=0.9, phenocopy rate=0.0, assuming no recombination. The R257c mutation is located within the conserved SRPTEK motif, important for connexon docking. This motif is a target of peptide mimetic inhibitors of GJIC for Cx43 and Cx32 (Warner, A., et al. (1995). Specific motifs in the external loops of connexin proteins can determine gap junction formation between chick heart myocytes. J. Physiol. 488, 721-728 and Berthoud, et al. (2000). Peptide inhibitors of intercellular communication. Am. J. Physiol. Lung Cell. Mol. Physiol. 279, L619-L622). Four additional unique GJC2 mutations were observed in other, smaller families: H16P in the N-terminal domain, R122Q in the intracellular loop, G146S in the intracellular loop, and P313L in the C-terminal domain were transmitted from an affected parent to an affected child. Samples were not available from other family members, and these cases are consistent with, but not informative for, linkage.

Figure 5:
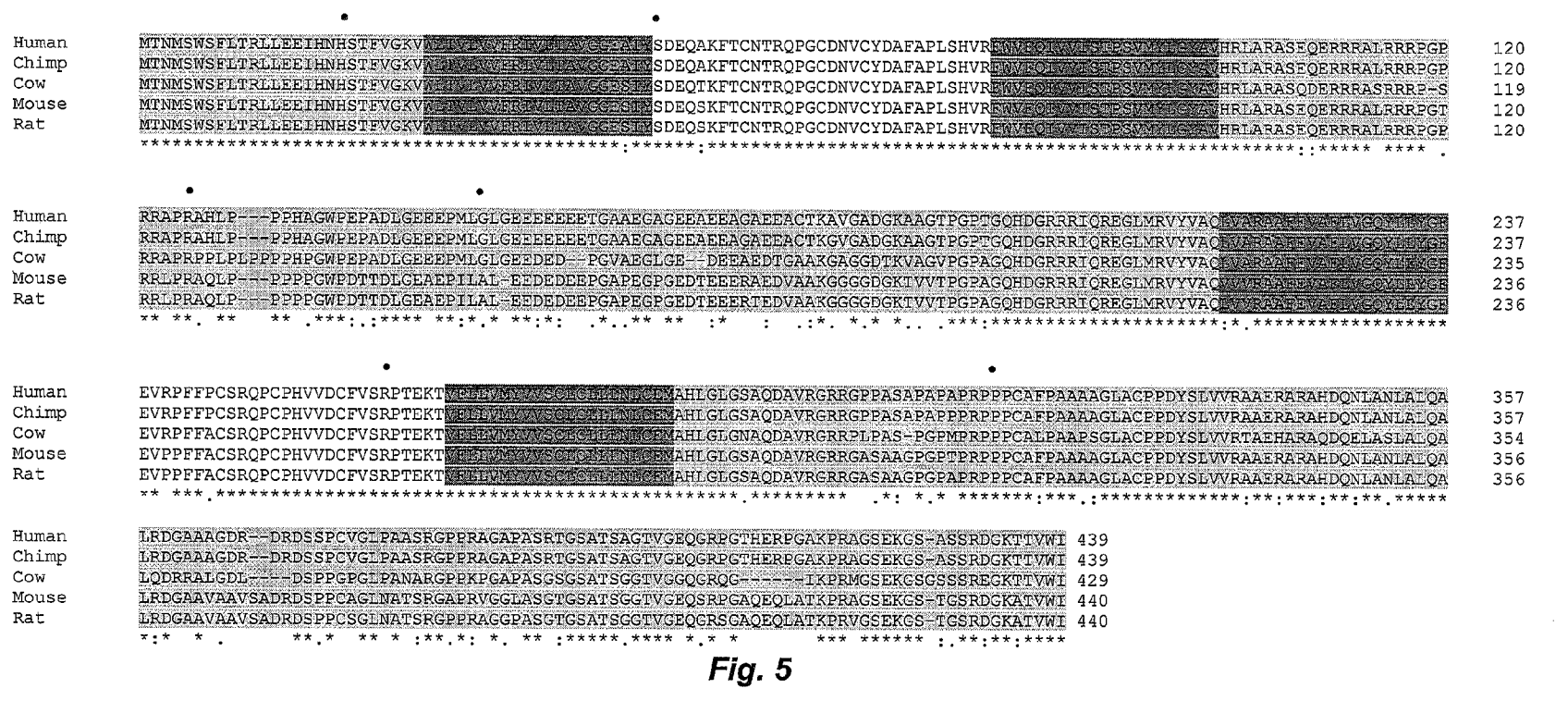

GJC2 mutations occur only in affected or at-risk individuals, cause a change in a conserved amino acid of Cx47, and were not present in 250 sequenced, ethnically matched controls (0 of 500 alleles). These missense mutations affect amino acids highly conserved in mammalian evolution, showing only one variation of glycine to alanine in the case of the G146S mutation (FIG. 5). Non-lymphedema-associated sequence variants were also identified (Table 2).

TABLE 2

Non-lymphedema related sequence changes in Cx47 observed in 150 lymphedema probands. Ref Seq. NM 020345.

| Location[1] | Flanking Sequence | Rs #[2] |
|---|---|---|
| Promoter −771 | ggcatctgctgcctgcc(G/A)gctcgtggctgctgcc (SEQ ID NO: 9) | |
| Promoter −692 | ggctgcatggggcag(C/G)ctgaggctgcaggggt (SEQ ID NO: 10) | 11581169 |
| Promoter −702 | tgcctcttggtgccc(G/A)accctgtgggtctggc (SEQ ID NO: 11) | |
| Promoter −526 | ggaggttctagatctc(G/A)aggtctaaggggttc (SEQ ID NO: 12) | 55662277 |
| Promoter −307 | gcctctggggtggggt(G/A)tagacagatgggtgg (SEQ ID NO: 13) | |
| Promoter −304 | tctggggtggggtgta(G/C)acagatgggtggga (SEQ ID NO: 14) | |
| Promoter −300 | ggtggggtgtagaca(ΔG)atgggtgggagagaa (SEQ ID NO: 15) | |
| Promoter −215 | cagagcccagactgc(C/T)ggaggatacaggcca (SEQ ID NO: 16) | |
| Promoter −181 | cgcctggactgggc(G/A)gctgggcagggagg (SEQ ID NO: 17) | |
| Promoter −145 | gagggcccaggcag(ΔC)ccccggtcgcttgct (SEQ ID NO: 18) | |
| Promoter −92 | ccacacaccctcggg(G/T)aggaccagcatcc (SEQ ID NO: 19) | |
| Intron 1 +58 | caggagacagcctca(C/T)gctgtgcccatggc (SEQ ID NO: 20) | |
| Coding Sequence 585 | 585C > T | 4653910 |
| Coding Sequence 957 | 957G > C | |

[1]Numbered from first ATG, human genome build 18 (http://genome.ucsc.edu)
[2]Reference sequence numbers from dbSNP (www.ncbi.nlm.nih.gov)

Figures 2, 4:
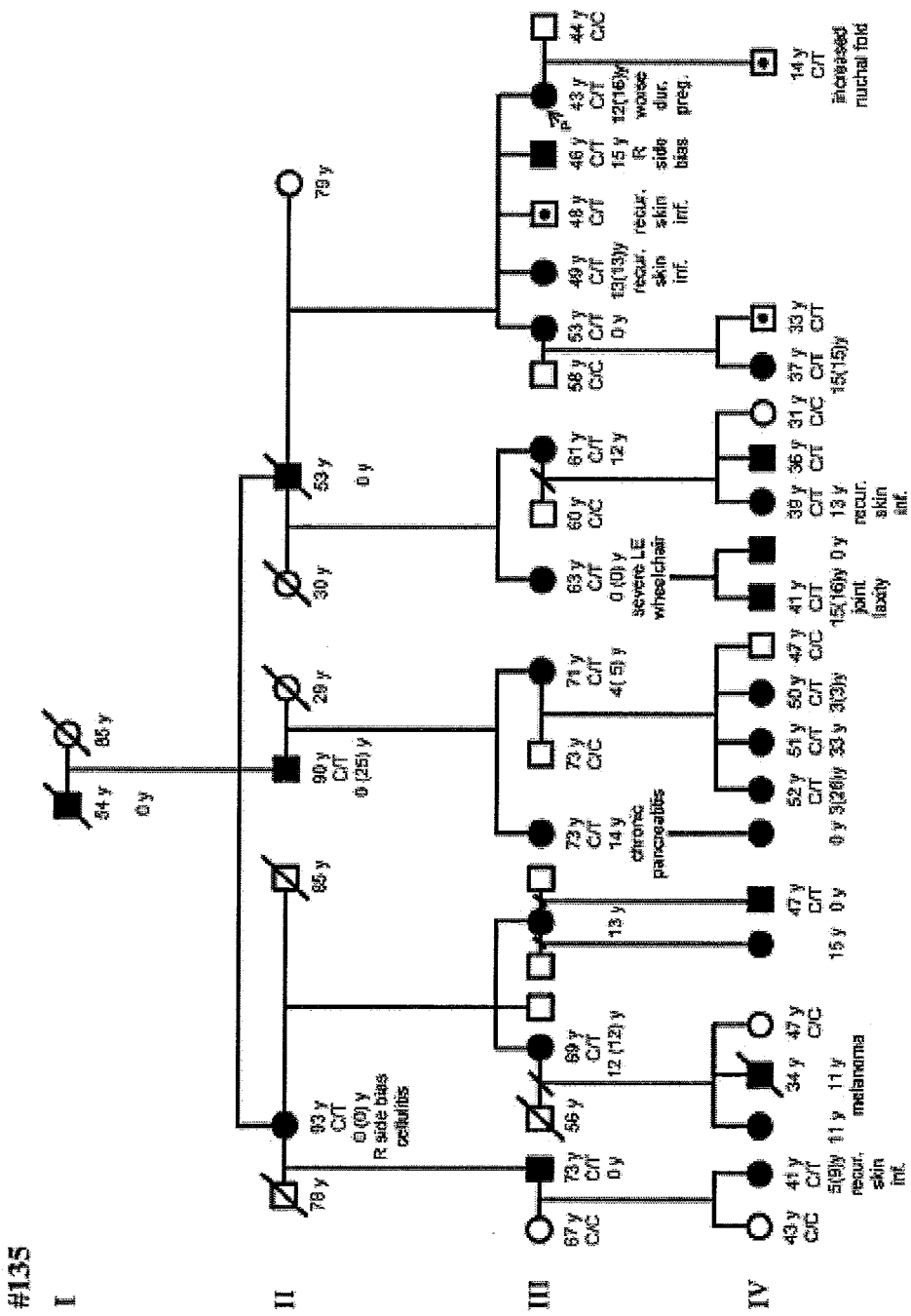

The current age or age at death, genotype with respect to GJC2, age at onset of lymphedema of the leg and/or hand, and other phenotypic features in the families demonstrating linkage are shown in FIG. 4. Uncomplicated lymphedema of the leg or hand was the only constant feature reported in the affected individuals. Individual IV-20, family 135, was reported to have a nuchal fold at birth but was nonpenetrant for lymphedema. Many affected individuals had onset of lymphedema in childhood or adolescence. Individuals IV-4, family 168, and 111-18, IV-19, and IV-20, family 135, were nonpenetrant males, showing reduced penetrance of GJC2 mutations in these families. Generally, males showed a later age at onset than females. Other features reported in some lymphedema pedigrees (ptosis, cellulitis, venous insufficiency, etc.) appeared sporadically in these families. Four individuals in family 135 reported recurrent skin infections. In the four smaller families with mutations, the clinical phenotypes were similar to the families demonstrating linkage, including a later age at onset.

Of note, two additional rare mutations, one leading to a truncated Cx47 protein (E44ter) and a 22 bp deletion leading to a truncation of the GJC2 protein at residue 30, were identified. These changes were not present in 500 control alleles but failed to segregate with disease in pedigrees. These early nonsense changes are predicted to code for a prematurely truncated polypeptide, leading to a null allele. The carriers of these truncation mutations showed no discernable phenotype, consistent with the Cx47-deficient mouse, in which heterozygous or homozygous null animals have no gross phenotype and no Cx47-specific developmental or functional abnormality (Odermatt, B., et al. (2003). Connexin 47 (Cx47)-deficient mice with enhanced green fluorescent protein reporter gene reveal predominant oligodendrocytic expression of Cx47 and display vacuolized myelin in the CNS. J. Neurosci. 23, 4549-4559 and Menichella, D. M., et al. (2003). Connexins are critical for normal myelination in the CNS. J. Neurosci. 23, 5963-5973). We show here that mutations in GJC2 cause primary lymphedema, through linkage in two families and significant genetic evidence from four independent families.

We hypothesize that coordinated gap junction function is needed to optimize the conduction of lymph from the periphery to the thoracic duct and is compromised in individuals with GJC2 missense mutations. In vivo evidence in rat mesenteric lymphatics shows significant impairment of contraction propagation upon treatment with nonspecific gap junction inhibitors (Zawieja, D. C., et al. (1993). Distribution, propagation, and coordination of contractile activity in lymphatics. Am. J. Physiol. 264, H1283-H1291 and McHale, N. G. et al (1992). Co-ordination of pumping in isolated bovine lymphatic vessels. J. Physiol. 450, 503-512). The GJC2 mutations are notable because they support an abnormality in lymphatic function rather than the previously identified mutations in genes causing abnormal lymphatic development. Such functional abnormalities could potentially benefit from the current development of gap-junction-modifying drugs (Verma, V., et al. (2009). Novel pharmacophores of connexin43 based on the "RXP" series of Cx43-binding peptides. Circ. Res. 105, 176-184 and Kjølbye, A. L., et al. (2008). Maintenance of intercellular coupling by the antiarrhythmic peptide rotigaptide suppresses arrhythmogenic discordant alternans. Am. J. Physiol. Heart Circ. Physiol. 294, H41-H49), offering a novel medical treatment for lymphedema. The role of GJC2/Cx47 in lymphatic function is unexpected because it has a demonstrated primary role in the central nervous system (CNS), with expression reportedly limited to oligodendrocytes (Odermatt, B., et al. (2003). J. Neurosci. 23, 4549-4559 and Nagy, J. I., et al. (2003). Coupling of astrocyte connexins Cx26, Cx30, Cx43 to oligodendrocyte Cx29, Cx32, Cx47: Implications from normal and connexin32 knockout mice. Glia 44, 205-218). Homozygous loss-of-function mutations in GJC2 cause Pelizaeus-Merzbacherlike disease (PMLD; MIM 608804), characterized by severe CNS dysmyelination. Neither individuals affected with PMLD nor their obligate heterozygous carriers of GJC2 mutations are reported to have a lymphatic phenotype, although the clinical phenotype of lymphedema is often subtle. Likewise, the clinical information available on our lymphedema patients and families would be insensitive to a mild clinical neurological abnormality. We observed no mutations in the transmembrane domains where many of the PMLD mutations are found (Orthmann-Murphy, J. L., et al. (2007). Loss-of-function GJA12/Connexin47 mutations cause Pelizaeus-Merzbacherlike disease. Mol. Cell. Neurosci. 34, 629-641). The GJC2 lymphedema mutations are distributed throughout the protein, with no geographical clustering.

However, the two mutations located in the extracellular loop domains (i.e., S45L and R257c) are predicted to interfere with connexon (i.e., hemichannel) assembly into functional channels. The linked R257c mutation is located in a conserved SRPTEK motif important for connexon docking; the importance of this motif is further underscored by a homologous autosomal-dominant GJA1 mutation (R202H) identified in families with oculodentodigital dysplasia (MIM 164200), with functional characteristics of poor plaque formation and impaired dye transfer and electrical coupling. Similarly, we expect these two extracellular mutations to result in impaired channel activity and propose that this might result in impaired coordination of pulsatile lymphatic flow (McHale, N. G., et al. (1992). Co-ordination of pumping in isolated bovine lymphatic vessels. J. Physiol. 450, 503-512). The mechanism through which the identified intracellular mutations mediate their effects is not clear, especially in light of the more recent recognition that connexin function is not limited only to their well-recognized channel activity but may involve hemichannel function or changes in cell adhesion or motility (Goodenough, D. A., et al. (2009). Gap junctions. Cold Spring Harb. Perspect. Biol. 1, a002576; Rhee, D. Y., et al. (2009). Connexin 43 regulates epicardial cell polarity and migration in coronary vascular development. Development 136, 3185-3193; Wei, C. J., et al. (2004). Connexins and cell signaling in development and disease. Annu. Rev. Cell Dev. Biol. 20, 811-838 and Elias, L. A., et al. A. R. (2007). Gap junction adhesion is necessary for radial migration in the neocortex. Nature 448, 901-907). Further characterization of the mutations reported here, especially with regard to their predicted dominant-negative effect with wild-type Cx47 or transdominant effect with other endogenous connexins expressed in LECs, will contribute to our understanding of the role of connexins in lymphatic function.

Example 2

After confirming the expression of Cx47 in human lymphatics and LECs, we chose to express the Cx47 mutations in communication deficient HeLa cells (17) to determine functional changes in GJIC. Four of five mis sense mutations were introduced by site directed mutagenesis into a vector containing human wild type Cx47 pIRES2-EGFP (a gift from Dr. S. Scherer), and the fidelity of the wild type and all mutant constructs confirmed by bidirectional sequence analysis. We measure electrophysiologic characteristics of GJIC between HeLa cell pairs transfected with the mutant constructs by dual whole cell patch clamp recording. Pairs of cells are chosen for study only if both express the GFP marker indicative of successful transfection.

Materials and Methods

Site Directed Mutagenesis:

A human WT Cx 47 construct subcloned into the bicistronic pIRES2-EGFP vector (Clontech) was obtained from S. Scherer laboratory (19). Single nucleotide substitutions S45L, G146S, R257c and P313L were introduced into human WT Cx47 using the QuickChange II XL Site-Directed Mutagenesis kit (Stratagene). Plasmids were introduced into One Shot Stb13 E. coli (Invitrogen), vector containing colonies were selected on kanamycin, and expanded by log-phase growth overnight on LB medium and plasmid DNA extracted using the Wizard Plus SV Miniprep DNA purification system (Promega). The fidelity of all clones was confirmed by bi-directional sequence analysis.

Transient and Stable Transfection of HeLa Cells:

HeLa cells used were transiently transfected using Lipofectamine 2000 and Optimem (Invitrogen) and subsequently stably transformed with FACS selection then G418 (1 mg/ml) maintenance as previously described.

Immunofluorescent Confocal Microscopy:

Human neonatal foreskin was collected anonymously as discarded tissue according to an IRB protocol. Samples were collected immediately after harvest in DMEM, then fixed in 2% paraformaldehyde for 2 hrs, then stored in 30% sucrose in 1×PBS overnight for cryosectioning, and sectioned in 6 μm slices at −30° C. Transfected (stable and transient) and untransfected HeLa cells were grown to near confluence in coverslip bottom dishes. All cells were rinsed with PBS and fixed with 2% paraformaldehyde. Subsequently, tissue and HeLa cells were processed similarly: following permeabilization with 0.1% Triton X, cells were blocked with 2% BSA. A human Cx47 antibody (ab) was obtained from the S. Scherer laboratory: polyclonal rabbit against amino acids 344-399 in the cytoplasmic C-terminal tail; we used human CNS tissue and positive oligodendrocyte staining as a positive control and primary antibody delete and rabbit IgG as negative controls (data not shown). Cx47 ab was diluted in 0.5% BSA in a 1:200 ratio, applied to cells and incubated at RT for one hour. Mouse monoclonal Prox1 (Chemicon) was used as a lymphatic marker for the foreskin samples. Cells were incubated with the secondary abs (Donkey Anti-Rabbit Cy5 and Donkey Anti-Mouse Cy3; Invitrogen) for one hour at RT and washed; Draq5 was used as a nuclear marker. HeLa images were acquired with an inverted Olympus Fluoview 1000 Confocal Microscope 100× oil, 1.4 NA objective. Foreskin images were acquired on a Zeiss Meta LSM 510 inverted confocal microscope with 40× oil, 1.3 N.A. objective. LECs (primary human microvascular adult dermal lymphatics; Lonza) were grown in fibronectin coated coverslip bottom MatTeks dishes in EGM™-2 MV—Microvascular Endothelial Cell Medium-2 (Lonza Inc.) to approximately 80% confluence, and prepared similarly but a commercially available (AbCam) Cx47 ab, polyclonal rabbit against amino acids 41-70 in the human sequence was used along with Drag 5 nuclear marker and phalloidin to mark f-actin.

Scrape Loading and Dye Transfer:

A confluent monolayer of HeLa cells (untransfected and stably transfected, as described above) was grown in DMEM with 10% FBS in coverslip bottom plates (MatTek) and placed in a temperature controlled microincubator (Zeiss). A 10×, 0.4 NA objective was used to collect DIC and GFP images every 5 seconds for 10 minutes without changing media. A pipette loaded with 1 μl Calcein AM (Invitrogen), a gap junction permissive dye with molecular weight 662, −4 charge when intracellular and fluorescent, was used to create a scrape across the monolayer. At least 5 replicate dishes were analyzed on the same day, and WT hCx47 expressing HeLas were grown and assayed as a concurrent control; assays were performed on at least 2 different batches of HeLa cells on different days. Quantitation of the rate of spread was calculated using MetaMorph, by obtaining integrated intensity at the 10th time point, within the first minute of imaging, and then at the endpoint at 10 min, and subtracting the initial intensity from that at the endpoint. Results are reported as mean and SEM, and tested for significance ($p<0.05$) using an unpaired Student's t-test.

Dual Whole Cell Patch Clamp Recordings:

Coupling currents were recorded using simultaneous double whole-cell patch clamp recordings from isolated pairs of cells that were in contact with one another (determined visually) as previously described. Briefly, the pipette solution consisted of (mM): 130 CsCl, 10 EGTA, 10 HEPES, 3 Mg-ATP, 2 Na-ATP, 0.5 $CaCl_2$, pH 7.3. The culture was bathed in a solution consisting of (mM): 140 NaCl, 5 HEPES, 5 glucose, 4 KCl, 2 CsCl, 2 $CaCl_2$, 2 pyruvate, 1 $BaCl_2$, pH 7.3. Transfected HeLas undergo electrophysiologic analysis in a blinded manner. Pairs of cells were chosen for study only if both expressed the GFP marker indicative of successful transfections; both stable and transient transfectants were analyzed. Patch pipettes were fabricated from borosilicate glass, and coupling currents were amplified by Axopatch 200A amplifiers, filtered at 1 KHz, and digitized at 5 KHz for subsequent analysis using pClamp software (Axon Instruments/Molecular Devices; Sunnyvale, Calif.). All experiments were carried out at room temperature (22° C.). Coupling current was quantified by measuring the peak current recorded in the pair when the neighboring cell received a 100 mV step membrane potential change (in both positive and negative directions). Step changes in membrane potential were delivered to each cell in the pair in sequence and the average current recorded in the neighboring cell was determined and divided by 100 to generate coupling current expressed in pA/mV. Means±SEM were calculated and statistical significance using a one-way analysis of variance and Tukey's post-hoc test, $p<0.05$.

Figure 6D:
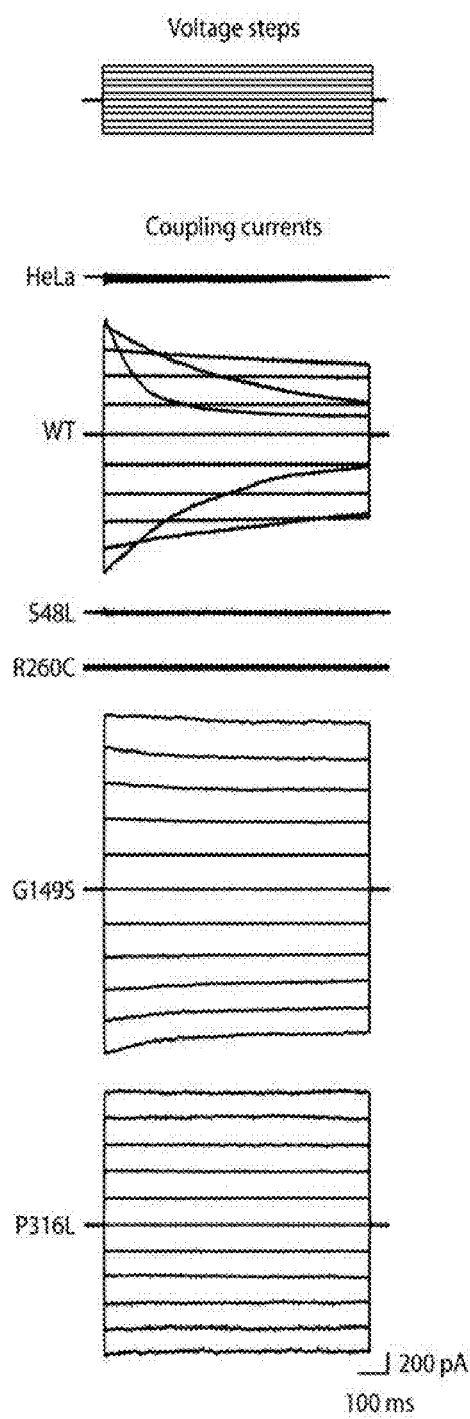
FIG. 6. Cx47 expression by immunofluorescent confocal microscopy and GJIC measured in pairs of HeLa cells using dual whole cell patch clamp recordings. A: Cx47 (red) and lymphatic marker, Prox-1 (green) in superficial dermal lymphatics of neonatal foreskin, 40× oil, 1.3 N.A; scale bar 50 µm. B: Cx47 (red), Prox-1 (green) and phalloidin (blue) in primary human dermal LECs, 63× oil, 1.4 N.A.; scale bar 50 µm. C: Mean coupling current in control HeLa, WT hCx47, and mutant expressing HeLa cell pairs. * indicates statistical significance using a one-way analysis of variance and Tukey's post-hoc test, p<0.05. D: Representative junctional currents in HeLa cell pairs in response to a voltage step protocol showing the absence of coupling in HeLa pairs expressing mutant Cx47 constructs S45L and R257c. In contrast, HeLa pairs expressing WT hCx47 and mutants G146S and P313L are well coupled. Untransfected HeLa cells have very little coupling current. Top panel shows the voltage stepping protocol (−100 to +100 in 20 mV steps).

Coupling current is quantified by measuring the peak current recorded in the pair when the neighboring cell receives a 100 mV step membrane potential change (in both positive and negative directions). Step changes in membrane potential are delivered to each cell in the pair in sequence and the average current recorded in the neighboring cell determined and divided by 100 to generate coupling current expressed in pA/mV (FIG. 6C). Replicate measurements (n=3-6) are made on at least two different days. FIG. 6D shows sample coupling currents. Consistent with previous reports, the junctional currents generated in the WT-hCx47 expressing HeLas show evidence of voltage-dependent gating. In stark contrast, HeLa cell pairs expressing the linked mutants S45L and R257c do not exhibit functional channels. HeLa cell pairs expressing the other missense mutations are well coupled, but do not show voltage sensitivity similar to that seen with the WT-hCx47 expressing cells. The untransfected HeLa cell pairs also show minimal channel function, as predicted.

Figure 7D:
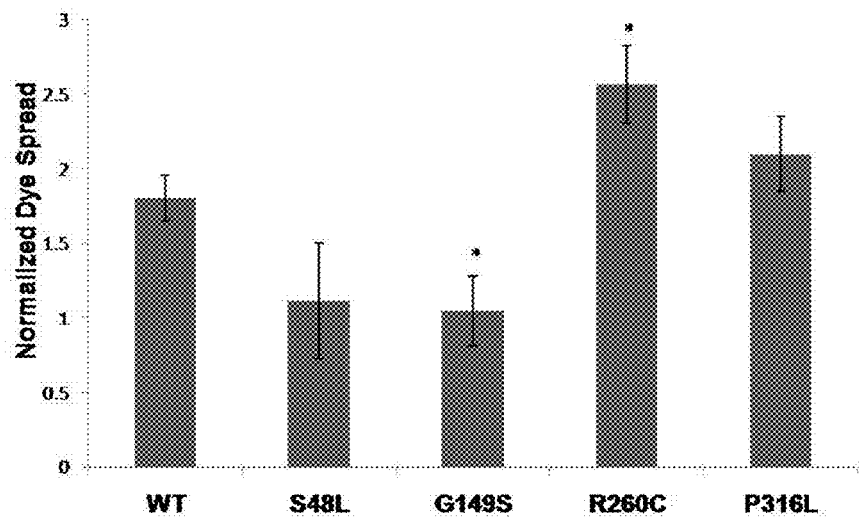
FIG. 7. GJIC function assessed by plaque formation and scrape dye transfer assay. A-C: Presence (A, arrow) or absence (B, C) of plaque formation at cell membrane in nearly confluent transiently transfected HeLa cells. A, WT hCx47, B, R257c and C, S45L. Red is human Cx47, blue is Draq5 nuclear marker, green is EGFP indicative of transfection; 100× oil, 1.4 N.A. D. Gap junction function measured by calcein dye scrape loading in confluent cultures of stably transfected HeLa cells, normalized to untransfected HeLa cells. * indicates statistical significance at p<0.05 in unpaired Student's t-test in comparison to WT transfected cells. E. Samples of calcein dye scrape loading images collected at 1 min and 10 min., 10× images, pseudocolored to reflect intensity, scale bar 100 µm.
Figure 7E:
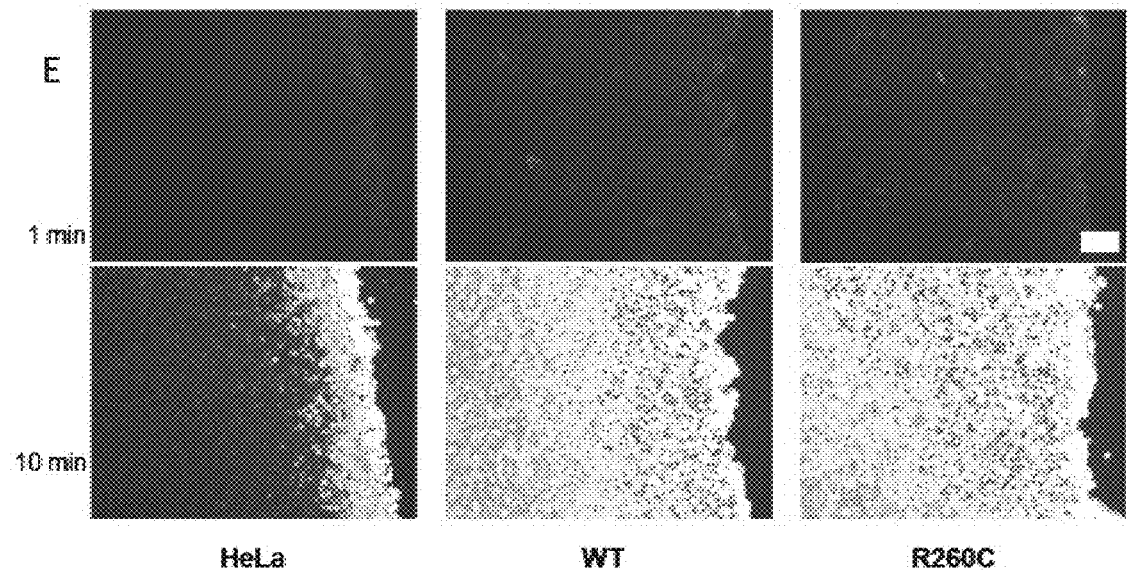

Immunofluorescence microscopy determines the presence or absence of Cx47 gap junction plaques when the constructs are transiently expressed in HeLa cells. Cx plaques reflect a physiologic accumulation of Cx channels in the cell membrane between cells (tens to thousands of channels); thus plaques are indicative of normal trafficking and gap junction formation at the cell membrane. Of the transfected HeLa cells, only those expressing the linked mutants S45L and R257c, fail to demonstrate Cx 47 plaques (FIG. 7A-C; Table 3).

TABLE 3

Summary of Functional Assays in HeLa Cells

| Transfected HeLas | WT-hCx47 | S45L | G146S | R257C | P313L |
|---|---|---|---|---|---|
| domain | | EL1 | IL | EL2 | C-Term |
| plaques | (+) | (−) | (+) | (−) | (+) |
| dye transfer[1, 2] | 1.80 ± 0.15 | 1.11 ± 0.39 | 1.05 ± 0.23* | 2.56 ± 0.26* | 2.10 ± 0.25 |
| elect coupling[3] | 31.6 ± 11.8 | 0.1 ± 0.0* | 16.2 ± 5.8 | 0.0 ± 0.0* | 37.6 ± 8.7 |

[1]Dye transfer expressed as ratio, with rate normalized to that obtained in untransfected HeLa cells.
[2]*indicates significantly different than WT at $p < 0.05$ unpaired Student's t-test.
[3]in pA/mV, *indicates statistical significance using a one-way analysis of variance and Tukey's post-hoc test, $p < 0.05$.
Domain abbreviations:
EL1, extracellular loop 1;
IL, intracellular loop;
EL2, extracellular loop 2.

In these mutants, Cx47 appears to concentrate in the ER. Unlike electrophysiologic measurements, dye transfer assays are used to assess GJIC of relatively large molecules. We also found significant differences in GJIC in HeLa cells overexpressing Cx47 lymphedema associated mutations by assessing rates of dye transfer in a conventional scrape assay using stably transfected HeLa cells normalized to rates in untransfected HeLa cells (FIG. 7D; Table 3). All four of the mutants tested demonstrate some degree of Calcein AM (−4 charge, m.w. 622) dye transfer, with some mutants showing significantly greater dye transfer than the WT-hCx47 transfected HeLa cells (R257c) and others showing less (G146S). It is not surprising that the mutants show some differences in GJIC between the electrophysiologic and dye transfer assays given that they are designed to measure different kinds of transport and that Cx channel permeability is now believed to be governed by factors including molecular shape, charge and size, in addition to channel conformation and composition.

We also observed two mutations, leading to a truncated Cx47 protein (E44ter and a 22 bp deletion leading to a truncation at residue 30), not present in 500 control alleles. These mutations likely lead to null alleles. They have no discernable phenotype in carriers and do not segregate with lymphedema in affected pedigrees. This is consistent with the Cx47 deficient mouse where the heterozygous or homozygous null animals have no gross phenotype, and no Cx47 specific developmental or functional abnormality.

For the first time, we present strong genetic evidence that mutations in Cx47 cause primary lymphedema, showing both statistical linkage of mutation with disease in two families and significant changes in GJIC when these and other novel Cx47 mis sense mutations are expressed in communication deficient human cells. A summary table of all the functional changes identified in HeLa cells transfected with the four different Cx47 missense mutations is provided (Table 3). We hypothesize that coordinated gap junction function is needed to optimize the conduction of lymph from the periphery to the thoracic duct. In vivo evidence in rat mesenteric lymphatics shows significant impairment of contraction propagation upon treatment with non-specific gap junction inhibitors. The Cx47 mutations are notable because they reflect an abnormality in lymphatic function rather than the previously identified mutations in genes causing abnormal lymphatic development. Such functional abnormalities potentially benefit from the current development of gap junction modifying drugs, offering a medical treatment for lymphedema.

The role of Cx47 in lymphatic function is unexpected since it has a demonstrated primary role in the CNS with expression essentially limited to oligodendrocytes. Homozygous loss-of-function mutations in Cx47 cause Pelizaeus-Merzbacher-like disease (PMLD), characterized by severe CNS dysmyelination. Neither individuals affected with PMLD nor their obligate heterozygous carriers of Cx47 mutations are reported to have a lymphatic phenotype, although the clinical phenotype of lymphedema is often subtle. Likewise, the clinical information available on our lymphedema patients/families would be insensitive to a mild clinical neurological abnormality. We observe no missense mutations in the transmembrane domains where many of the PMLD mutations are found.

The Cx47 lymphedema mutations are distributed throughout the protein, with no geographical clustering. However, those mutations not forming plaques, and without evidence of electrical coupling are both located in the extracellular loop domains of Cx47 where mutations are predicted to interfere with connexon (i.e., hemichannel) assembly into functional channels. Those mutations forming plaques normally, but with abnormal gap junction function, are located in the intracellular domains. As mentioned previously, the linked Arg257Cys mutation is located in a conserved SRPTEK motif important for connexon docking; the importance of this motif is further underscored by a homologous autosomal dominant Cx43 mutation (Arg202His) identified in families with oculodentodigital dysplasia (ODDD), with similar characteristics of poor plaque formation and impaired dye transfer and electrical coupling. Further characterization of the mutations reported here, especially with regard to their suspected dominant negative effect with WT Cx47, or transdominant effect with other endogenous Cxs expressed in LECs, will contribute to our understanding of the role of Cxs on lymphatic function.

Example 3

Connexin Expression and Gap Junction Function in Lymphatic Vessels and Endothelial Cells Lymphatic vasculature is distinct from its blood vascular counterpart and increasingly its unique functions beyond fluid homeostasis are being documented in a variety of physiologic and pathologic processes including immunosurveillance, inflammation, wound healing and cancer metastasis. We sought to determine Cx expression in normal human superficial dermal lymphatic vessels and determine Cx expression and GJIC in primary human dermal lymphatic endothelial cells (LECs). By immunofluorescent microscopy, Cx37 and 43 are expressed in LECs and Cx37, 40 and 43 are expressed in human superficial dermal lymphatic vessels. RT-PCR revealed mRNA transcripts of Cx37, 43 and 47 in LECs; Cx40 was barely detectable. GJIC in LECs are quantitated in real time in LECs using a parachute dye transfer technique and electrical coupling is measured by dual whole cell patch clamp recording; dye transfer was inhibited by conventional gap junction inhibitors. For the first time, this paper documents the expression of specific Cxs in superficial dermal lymphatics in human neonatal foreskin by immunofluorescent microscopy and in primary dermal LECs. Importantly we show that there are endogenous functional gap junctions in LECs. It remains to be determined how Cxs interact and contribute to normal and abnormal lymphatic vascular function.

The expression and distribution of connexins (Cxs) and function of gap junction intercellular communication (GJIC) in lymphatic vasculature may be central to lymphatic physiology. Lymphatic vessels demonstrate gap junctions, first suggested in rat mesenteric lymphatic capillaries and documented in cultured lymphatic endothelial cells (LECs) by electron microscopy. Gap junction communication mediates the propagation of spontaneous contractions in mesenteric lymphatics. Because LECs and lymphatic vessels importantly differ in structure, function and signaling from their better known blood vascular counterparts, we reasoned that their GJIC would also reflect unique vascular and tissue specific features. This hypothesis is supported by recent surveys in gene expression contrasting LEC with blood endothelial cells (BECs) listing a relatively high expression of Cx37 in BECs versus LECs and Cx47 expressed only in LECs.

We report, for the first time, the presence of functional gap junctions in primary adult human dermal microvascular LECs. Two conventional vascular Cx proteins, Cx 37 and 43, are expressed as shown by immunofluorescent confocal microscopy, and further supported by semiquantitative RT-PCR. The significance of these in vitro findings is validated by the concurrent expression of Cxs 37, 40, and 43 in superficial lymphatic vessels in human neonatal foreskin. Functional gap junctions are also seen in cultured LECs using two different approaches: real time fluorescent dye transfer technique on confluent monolayers and electrophysiologic coupling between LEC pairs by dual whole cell patch clamp recordings. These findings support our hypothesis that gap junctions and their associated Cx proteins are important mediators of lymphatic function.

Materials and Methods

Reagents:

Primary antibodies against human antigens including rabbit polyclonal anti-Cx40, goat polyclonal anti-Cx37, were purchased from Santa Cruz (Santa Cruz, Calif.). Rabbit anti-Cx43 was purchased from Sigma Chemical (St. Louis, Mo.). Mouse anti-Cx45 was obtained from Millipore. Rabbit anti-VEGFR-3/Flt-4 and anti-LYVE-1 were purchased from ReliaTech GmbH (Braunschweig, Germany) and AngioBio Co (Del Mar, Calif.), respectively. Mouse monoclonal anti-Prox-1 was obtained from AbCam (Cambridge, Mass.). Synthetic connexin-mimetic peptide Gap-27 (amino acid sequence Ser-Arg-Pro-Thr-Glu-Lys-Thr-Ile-Phe-Ile-Ile) and 18α-glycyrrhetinic acid (GRA) were purchased from Sigma Chemical (St. Louis, Mo.). Human fibronectin, Calcein AM, Alexa Fluor 488 and 609 Phalloidin, and Alexa Fluor 488 donkey anti-goat (DaG) were purchased from Invitrogen (Carlsbad, Calif.). Donkey Anti-Rabbit Cy3 (DaR) and donkey Anti-Goat Cy5 were purchased from Jackson ImmunoResearch Laboratories, Inc. (West Grove, Pa.). DRAQ5 nuclear stain was purchased from Biostatus Ltd. (Leicestershire, UK).

Cell Culture:

Adult human dermal lymphatic microvascular endothelial cells were cultured in EGM™-2 MV—Microvascular Endothelial Cell Medium-2 (both from Lonza Inc.) Coverslip bottom dishes (MatTek, Inc) were coated with fibronectin using a concentration of 6 μg/ml in 1× phosphate buffered saline (PBS) prior to culture and imaging. Human telomerase-transfected human dermal lymphatic endothelial cells (hTERTs; gift of M. Pepper lab), are routinely used in the lab because they grow rapidly and manifest many characteristics of primary LECs (Nisato R E, et al. Generation and characterization of telomerase-transfected human lymphatic endothelial cells with an extended life span. *Am J. Pathol.* 2004; 165:11-24). hTERTs were grown routinely in MCDB-131 (VEC Technologies).

Immunofluorescence Imaging:

Human neonatal foreskin samples were collected immediately after harvest in DMEM, then fixed in 2% paraformaldehyde for 2 hrs, then stored in 30% sucrose in 1×PBS overnight; for cryosectioning they were submerged in cold 2-methylbutane for 20 seconds, liquid nitrogen for 2-5 seconds, and sectioned in 6 μm slices at −30° C. Cells were rinsed with PBS, then fixed with 2% paraformaldehyde. Subsequently cells and tissue were handled similarly. Following permeabilization with 0.1% Triton X, cells were blocked with 2% BSA. The primary antibodies (see above) were diluted in 0.5% BSA usually in a 1:100 ratio, applied to cells and incubated at RT for one hour. The cells were incubated with appropriate secondary antibodies for one hour at RT and washed. Coverslips were mounted on slides with Gelvatol and coverglass bottom dishes were covered in 1×PBS, and both were stored at 4° C. Images were taken of dishes with an inverted Olympus Fluoview 1000 confocal microscope and 63× oil 1.4 N.A. objective, and images of tissues were taken with an Olympus Fluoview 500 confocal microscope using 20×0.8 N.A. objective.

RNA Analysis:

LECs were grown as described in T75 flasks in complete media. Total RNA extraction was performed using TRIzol (Invitrogen). Taqman Gene Expression Assays for mRNA transcripts for Cxs 37, 40, 43, 45 and 47 were run in duplicate on an ABI 7900 using default settings and cycling conditions; amplicons ranged from 57-68 bp. Relative gene expression was calculated according to manufacturer's recommendations using the comparative method; human control RNA (ABI; part of GAPDH standard) was used as the calibrator, and averaged cycle thresholds (Cts) were normalized relative to those of GAPDH (ABI) in the corresponding sample.

Intercellular Communication Assay:

To characterize intercellular gap junction communication over time between seeded donor cells and an acceptor monolayer, LECs were loaded with 2.5 μM Calcein-AM (Invitrogen) in (PBS) for 30 min at 37° C. Excessive dye was removed by rinsing three times in PBS before dislodgment using 500 μl 0.25% Trypsin-EDTA. Detached cells were dispersed with a pipette and 10 μl cell suspensions was added to a confluent LEC monolayer in MCDB-131 supplemented with 25 mM HEPES. To ensure attachment of dye loaded suspended cells, the dish was incubated at 37° C. for 40 min prior to syringe filtration of the medium to remove floating cells that would interfere with subsequent imaging. The dish was thereafter mounted in a temperature controlled open chamber microincubator (Harvard Apparatus) on an inverted Olympus IX81 microscope. Dual images were collected using MetaMorph software 6.3 (MDS Analytical Technologies) every minute for one hour, in 5 positions with a 20×, 0.7 N.A. objective at 50 ms and neutral density filter using differential interference contrast (DIC) and green fluorescent protein (GFP) filter sets. Experiments using inhibitors were done in a batched blinded manner so that cultured cells from the same passage and plating were used for treatments and appropriate inhibitors on the same day. GRA was solubilized in 100% EtOH, diluted in media and used at a concentration of 10 μM, and cultures were treated together with dye loaded cells for 40 min, then washed, and imaged in MCDB-131 supplemented with 25 mM HEPES; EtOH vehicle control experiments were also run. The Gap 27 was solubilized in DMSO (diluted in 10 μl volume to make 50 mM stock) and diluted in media to 500 μM final concentration. The Gap27 was handled similarly to GRA and a DMSO control was measured on the same day. Significance was assigned at p<0.05 and treatments were analyzed as independent samples using a Student's t-test. Analysis was done blindly, using MetaMorph software 6.3, as indicated in the Methods section of the paper.

Whole-Cell Patch Clamp Recordings:

Coupling currents were recorded using simultaneous double whole-cell patch clamp recordings from isolated pairs of LECs that were in contact with one another (determined visually) as previously described (Srinivas M, et al. Voltage dependence of macroscopic and unitary currents of gap junction channels formed by mouse connexin50 expressed in rat neuroblastoma cells. J. Physiol. 1999; 517 (Pt 3):673-89; Srinivas M, et al. Functional properties of channels formed by the neuronal gap junction protein connexin36. J. Neurosci. 1999; 19:9848-55; and del Corsso C, et al. Transfection of mammalian cells with connexins and measurement of voltage sensitivity of their gap junctions. Nat. Protoc. 2006; 1:1799-809). Briefly, the pipette solution consisted of (in mM): 130 CsCl, 10 EGTA, 10 HEPES, 3 Mg-ATP, 2 Na-ATP, 0.5 $CaCl_2$, pH 7.3. The culture was bathed in a solution consisting of (in mM): 140 NaCl, 5 HEPES, 5 glucose, 4 KCl, 2 CsCl, 2 $CaCl_2$, 2 pyruvate, 1 $BaCl_2$, pH 7.3. Patch pipettes were fabricated from borosilicate glass, and coupling currents were amplified by Axopatch 200A amplifiers, filtered at 1 KHz, and digitized at 5 KHz for subsequent analysis using pClamp software (Axon Instruments/Molecular Devices; Sunnyvale, Calif.). Experiments were carried out at room temperature (22° C.), and on two separate days. Coupling current was quantified by measuring the peak current recorded in the pair when the neighboring cell received a 100 mV step membrane potential change (in both positive and negative directions). Step changes in membrane potential were delivered to each cell in the pair in sequence and the average current recorded in the neighboring cell was determined and divided by 100 to generate coupling current expressed in pA/mV.

Results

We show Cx specific immunolocalization in human superficial dermal lymphatic vessels and in primary adult dermal microvascular LECs. Antihuman antibodies for Cx 37, 40, 43, 45 were initially used based on the literature of blood vascular Cx expression; Cx47 was subsequently evaluated by semiquantitative RT-PCR in light of recent microarray data suggesting unique Cx47 expression6.

Figure 8:
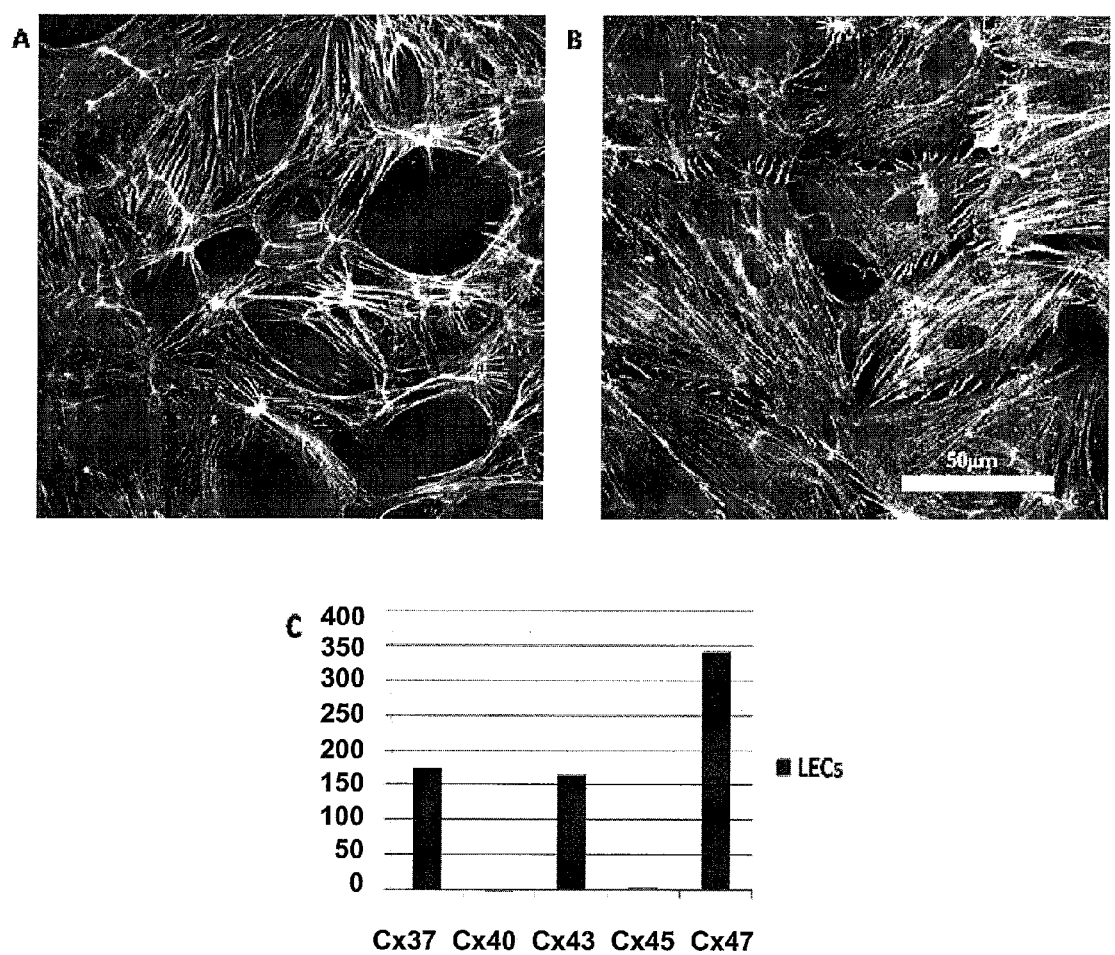
FIG. 8. Cx expression in human dermal LECs. A-B: Immunofluorescent confocal microscopy shows Cx antibodies in red, F-actin in green, and Draq5 nuclear stain in blue: A. Cx37, B. Cx43. 63× oil, 1.4 NA objective; scale bar 50 µm. C. Relative Cx gene expression, duplicate LEC samples normalized to GAPDH.

Connexin Expression in Human Dermal LECs:

Cx 37 and 43 are identified in primary human dermal LECs by immunofluorescent microscopy (FIG. 8 A, B). Cx37 expression is weak but present, although it is primarily cytoplasmic. Cx43 is strongly expressed, especially in junctional areas between cells, as expected for functional gap junctions. Interestingly, Cx40 which is commonly expressed in a variety of blood vessels and cultured BECs, was not detected by immunofluorescence (data not shown). Cx45, which is uncommonly expressed in BECs, was also not observed (data not shown). Semiquantitative RT-PCR was performed on LECs assessing mRNA levels of these same Cxs, and in addition, Cx47. mRNA transcript levels were highest for Cx37 and 43 and 47; those for Cx45 were barely detectable and undetectable for Cx40 (FIG. 8C).

Figure 9:
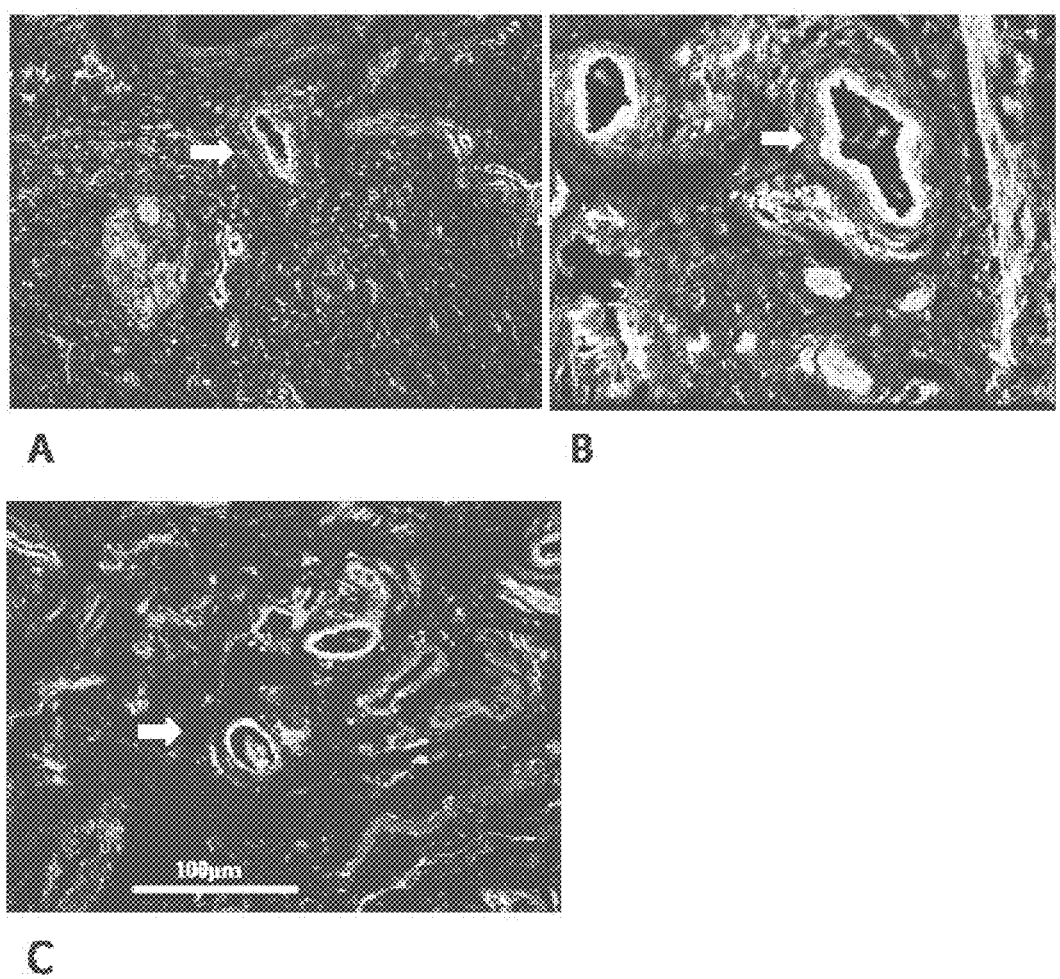
FIG. 9. Cx expression in superficial lymphatics in neonatal foreskin. Lymphatic markers in red, Cxs in green, nuclear marker in blue; colocalization indicated by yellow, marked with arrows. A. Cx43 and VEGFR3; B. Cx40 and Prox-1; C. Cx37 and LYVE-1. 20× oil, 0.85 N.A. objective, scale bar 100 µm.

Connexin Expression in Lymphatics in Human Neonatal Foreskin:

Since Cx was expressed in cultured cells, we evaluated the expression of Cxs in human lymphatic vessels ex vivo. Variation in gene expression has been well documented in cultured LECs, so the confirmation of expression in tissue was important prior to the ongoing use of primary LECs for in vitro studies of GJIC. The same antihuman antibodies used on the LECs were used on the foreskin tissue. Cx 37, 40, and 43 were detected in superficial dermal lymphatic vessels in human neonatal foreskins (FIG. 9). Interestingly, Cx40 was detected in these neonatal superficial dermal lymphatic vessels despite little evidence of its expression in adult LECs. Conventional lymphatic markers, LYVE-1, Prox-1, and VEGFR3 were used to identify lymphatic vessels and colocalization was demonstrated with antibodies against human Cx 37, 40, and 43, as indicated, using confocal microscopy. As with the cultured LECs, no Cx45 was detected (data not shown).

Gap Junctional Intercellular Communication Measured by Dye Transfer:

Since the presence of Cx, even in well localized plaques along the cell membrane, does not necessarily confirm gap junction function, we investigated GJIC in LECs in 2D culture. We optimized a so called "parachute" dye loading technique reflecting normal physiologic function and allowing quantitation of temporal differences in gap junction function more than scrape leading or microinjection.

Figure 10:
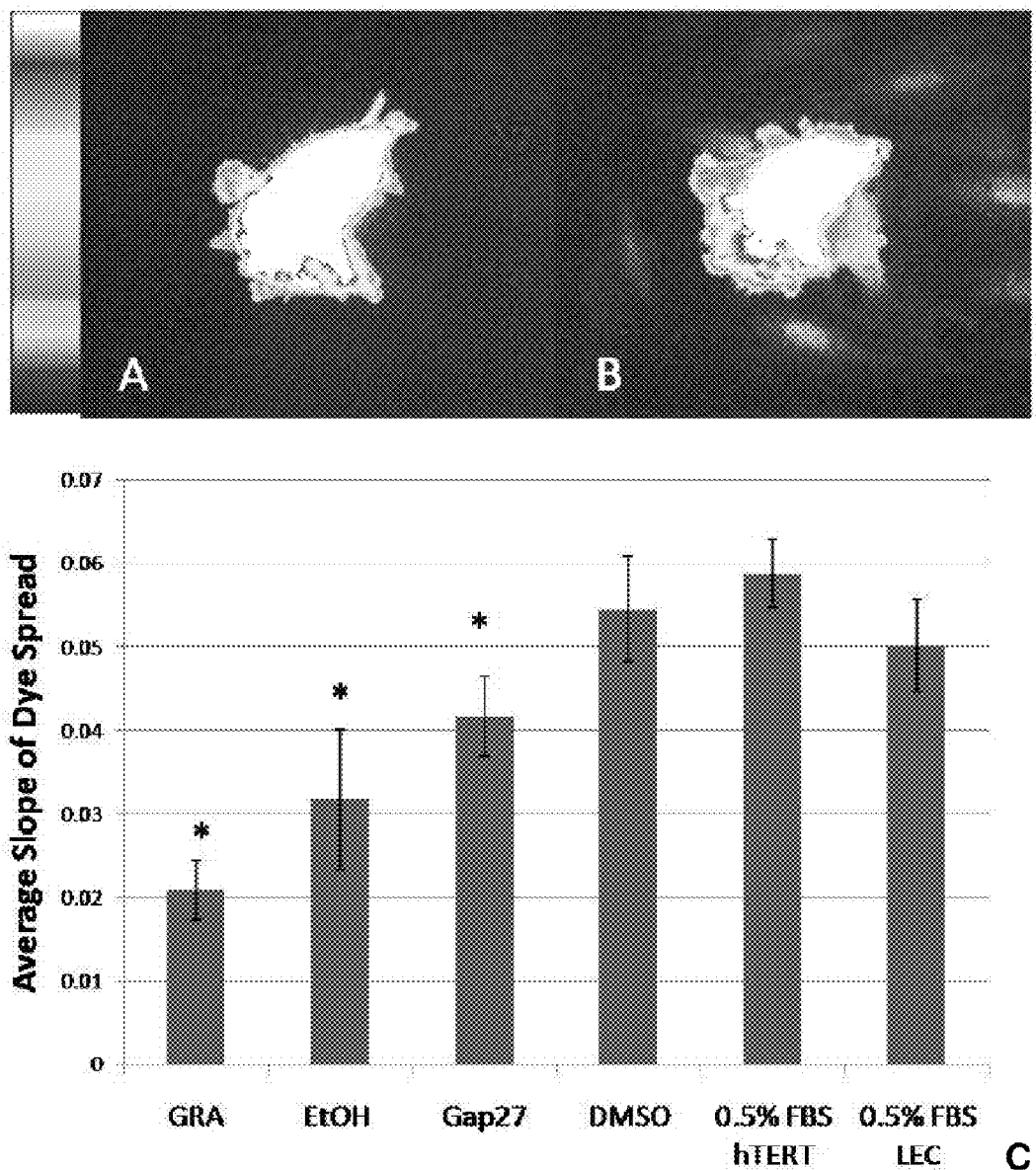
FIG. 10. GJIC by dye transfer assay. A-B. 20× pseudocolored images at time 0 (A), and 1 hr (B), showing dye (blue) spread from donor LEC to underlying monolayer. C. Dye transfer assays in hTERTs and LECs; hTERTs treated with inhibitors and respective vehicle controls (GRA and EtOH; Gap 27 peptide and DMSO). * Significance, p<0.05 compared to hTERT control (0.5% FBS).

FIG. 10A-B shows a sample of the pre and post (1 hr) images obtained from a typical GJIC experiment demonstrating the method of parachuting dye loaded LECs onto a confluent LEC monolayer (no dye). Calcein AM allows cell permeable loading, and with a molecular weight of 662, is frequently used in gap junction communication studies. To ensure cell attachment, the dish was incubated for 40 min prior to imaging, then mounted in a temperature controlled microincubator on an inverted fluorescent microscope. Dual images, differential interference contrast (DIC) and green fluorescent protein (GFP), were collected every minute for one hour using a 20× objective. The pseudocolored bar on the left indicates the range of color corresponding to signal intensity, where white is most intense and black is least. Initially the donor cell shows a high intensity signal on a background of cells with little to no signal, but by 1 hr the intensity of the donor cell signal has decreased and correspondingly cells in the surrounding monolayer have taken up dye from the donor cell and then adjoining cells. Replicate blinded experiments were performed on at least 2 separate days, and quantitation of dye spread was determined in an automated manner using Metamorph and standardized regions of interest with autothresholding. Additional validation of GJIC was afforded in hTERTs with the use of conventional inhibitors of gap junctions; a non-specific inhibitor 18 $\alpha$-glycerrhetinic acid, a non-specific gap junction inhibitor (GRA) and a connexin mimetic peptide, Gap 27, with a sequence targeted to the extracellular loop 2 of Cx4334 (FIG. 10B). In both primary adult human dermal LECs and immortalized hTERTs (neonatal derived) GJIC was demonstrated by dye transfer and significantly reduced in response to conventional gap junction inhibitors. The extent of inhibition of GJIC is greater for the GRA, although some of that is attributable to the effect of EtOH vehicle.

Figure 11:
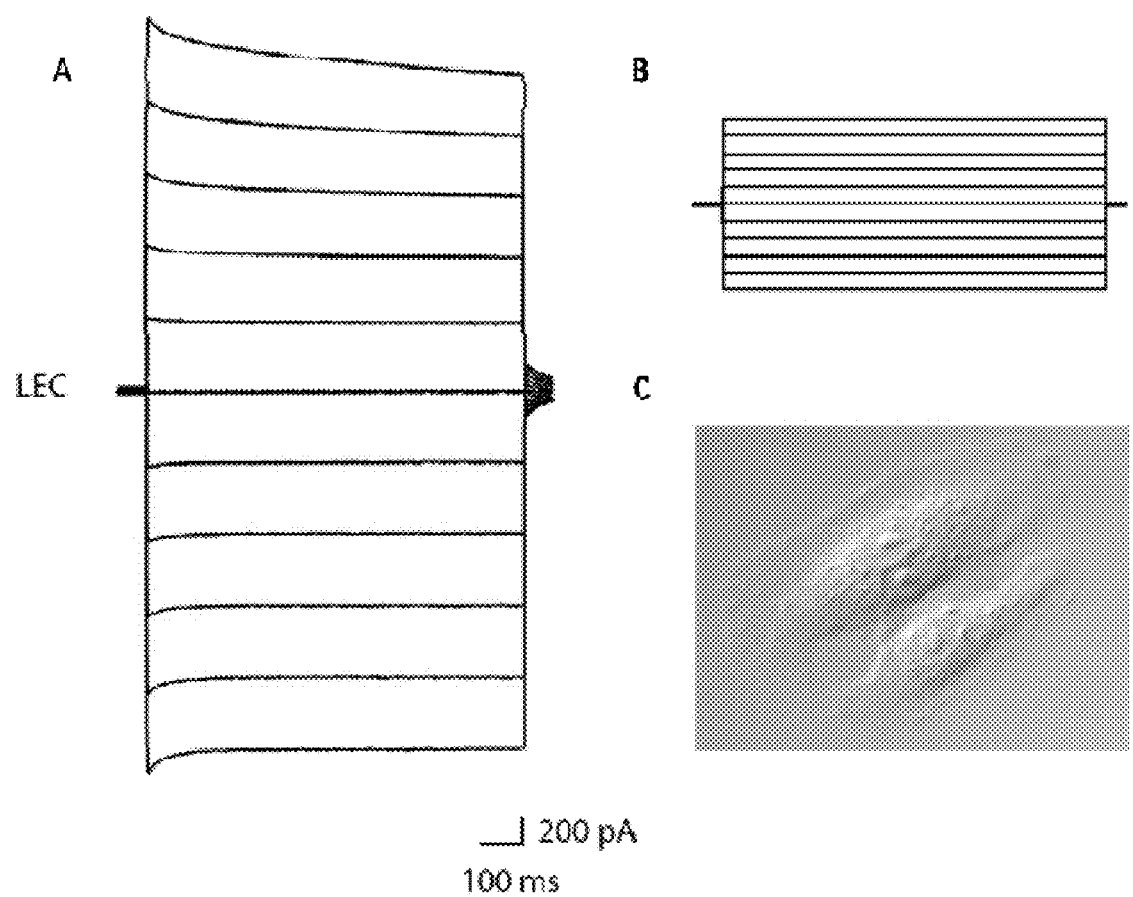
FIG. 11. Electrically coupled LECs. A. Representative junctional currents in LEC pair, showing strong coupling, voltage dependent decline above 40 mV applied voltage. B. voltage stepping protocol (−100 to +100 in 20 mV steps). C. Paired LECs used in dual whole cell patch clamp recordings, DIC 63× oil, 1.4 N.A.

Gap Junctional Intercellular Communication by Dual Whole Cell Patch Clamp Recording:

Dye transfer studies of GJIC provide a quantitative assessment of transport of relatively larger molecules (but less than 1 kDa) and different Cxs show different selectivity based on molecular size, charge, and shape. In contrast, dual whole cell patch clamp recordings afford sensitive measurement of the junctional conductance between cells. We measured electrophysiologic characteristics of GJIC between LEC pairs by dual whole cell patch clamp recording. In LECs (n=6), mean coupling current in LECs is 52.2+/−12.2 pA/mV. Sample coupling currents between LEC pairs demonstrate strong electrical coupling and voltage dependent decline in junctional current at applied voltages (FIG. 11).

Discussion

Others previously reported dye transfer between lymphatic endothelial cells in guinea pig mesenteric lymphatics (von der Weid P Y, et al. Functional electrical properties of the endothelium in lymphatic vessels of the guinea-pig mesentery. *J. Physiol.* 1997; 504 (Pt 2):439-51) or reported data suggesting the presence of functional gap junctions in rat mesenteric lymphatics (Zawieja D C, et al. Distribution, propagation, and coordination of contractile activity in lymphatics. *Am J. Physiol.* 1993; 264:H1283-91); now we present the first evidence of functional gap junctions in cultured human LECs and identification of specific Cx expression in neonatal human dermal lymphatics vessels. We identify the expression of Cx37 and 43 in cultured human microvascular LECs and Cx37, 40, and 43 in superficial lymphatic vessels in human neonatal foreskin by immunofluorescence. Semiquantitative RT-PCR confirmed mRNA transcript levels consistent with the immunofluorescent findings, and identified the expression of Cx47 as well. Using both a dye loading technique and dual whole cell patch clamp recording, functional GJIC is confirmed in cultured LECs.

Connexin Expression in Lymphatics and LECs:

Cxs detected in microvascular LECs and superficial dermal lymphatics are generally consistent with those reported in blood vascular endothelium. Cx37, 40 and 43 are generally expressed in vascular endothelial cells, but there is an acknowledged variation among developmental stage, species (Cruciani V, et al. The detection of hamster connexins: a comparison of expression profiles with wild-type mouse and the cancer-prone Min mouse. *Cell Commun Adhes.* 2004; 11:155-71), tissue, and vessel type. Expression of Cx47 has not been specifically investigated in BECs or blood vessels, especially since its distribution and function has primarily been characterized in the CNS. Cx45 expression is occasionally reported in endothelium in animal models but most of the vascular Cx45 expression appears to be in the vascular smooth muscle. Cx 31.1 is equally expressed in BECs and LECs in a recent cDNA microarray study (Podgrabinska S, et al. Molecular characterization of lymphatic endothelial cells. *Proc Natl Acad Sci USA.* 2002; 99:16069-74), but like Cx47 it was not initially targeted for our evaluation in lymphatics or LECs.

Another BEC/LEC expression survey reported relatively higher expression of Cx37 in BECs (Wick N, et al. Transcriptomal comparison of human dermal lymphatic endothelial cells ex vivo and in vitro. *Physiol Genomics.* 2007; 28:179-92). This difference may reflect other factors besides BEC/LEC identity such as vessel size and tissue specificity. Cx43 is the most ubiquitously expressed Cx in general, and in BECs and blood vessels as well. Similarly Cx43 is well expressed in both human LECs and in the superficial lymphatics in human neonatal foreskin.

Historically, some cross-reactivity is reported between commercially available Cx43 and 45 antibodies but this was not judged a confounding issue since Cx45 was not detected in our immunofluorescent studies. Cross reactivity of Cx40 and Cx43 antibodies has also been reported (Severs N J, et al. Immunocytochemical analysis of connexin expression in the healthy and diseased cardiovascular system. *Microsc Res Tech.* 2001; 52:301-22), but is unlikely based on the difference in presence of expression between these Cxs in LECs and neonatal foreskin. While mRNA levels will not necessarily correspond to protein expression levels, these data support our results independent of antibody specificity (i.e., Western blots).

Gap Junction Function in LECs:

Functional gap junctions were documented in cultured LECs using dye loading techniques and appropriate response to inhibitors. Others previously noted that the currently available inhibitors lack specificity, in the case of GRA, and there is a lack of consensus regarding the mechanism of action as in the case of the Cx peptide mimetics. In published literature, the degree of inhibition afforded by Cx peptide mimetics is variable, but our results are consistent with that reported by others and may reflect the presence of Cx 40 and 47 that are not expected to be responsive to the Gap 27 peptide. Our use of two different approaches to quantitate GJIC in addition to appropriate inhibition by both non-specific and gap peptide mimetics is strong evidence of functional gap junctions in these cells. While we documented conductance between paired LECs with voltage dependent gating consistent with that found in various Cx channels, we are unable to attribute these characteristics to a single Cx since we documented different Cxs in LECs and channels may be comprised of one or more Cxs. Recently the non-junctional connexon functions, so called hemichannels, were associated with at least some Cx proteins, but we made no attempt in this study to address these structures or their function in LECs.

Conclusions

Cxs 37 and 43 are expressed in primary human LECs and superficial dermal lymphatics in human neonatal foreskin and semiquantitative RT-PCR. Cx40 is not expressed in primary adult human LECs but is expressed in neonatal superficial dermal lymphatic vessels. Using a fluorescent dye loading technique, functional gap junctions were identified in cultured LECs and were inhibited by conventional gap junction inhibitors and GJIC was also confirmed by electrical coupling determined through dual whole cell patch clamp recordings. These findings support a unique physiological role for GJIC in lymphatic vascular endothelium, and offer a potential causal role for GJIC in understanding lymphatic disease. Given the concurrent expression of at least two Cx proteins in LECs, future studies will determine the physiologic role of individual Cx proteins and/or evidence of heterotypic or heteromeric gap junctions in normal lymphatic vessels.

Example 4

Connexin 47 Mutations Increase Risk for Secondary Lymphedema Following Breast Cancer Treatment Secondary lymphedema is frequent, and one of the most feared complications of breast cancer treatment associated with removal of lymph nodes or use of radiation on lymph nodes during breast cancer treatment. The staging and treatment of other cancers involving removal and/or radiation of lymph nodes may also precede secondary lymphedema. Secondary lymphedema as a complication of breast cancer therapy occurs in approximately 30% of patients, but estimates range from 2% to 80%, depending on the study population, and on the timing and method of ascertainment of lymphedema. As many as 600,000 women may suffer from secondary lymphedema following breast cancer treatment. Recognized risk factors for secondary lymphedema include treatment related factors: extent of surgery, radiation and chemotherapy; disease related factors: stage at diagnosis, pathological nodal status and number of dissected lymph nodes; and patient related factors: age at diagnosis, body mass index and presence of a sedentary lifestyle. As demonstrated by these risk factors, secondary lymphedema is viewed as the consequence of a traumatic event. This contrasts with familial or primary lymphedema which is considered to have a genetic etiology. Primary lymphedema is viewed as a developmental abnormality which often segregates within families and has multiple causal genes. The contribution of a genetic susceptibility to the subsequent risk of developing secondary lymphedema following surgical trauma, radiation, and other tissue insults has not been evaluated.

Finegold et al. (HGF and MET mutations in primary and secondary lymphedema. Lymphat Res Biol 2008; 6:65-8) reported a shared, rare mutation in the high affinity receptor for hepatocyte growth factor, MET, between a patient with primary lymphedema and an unrelated patient with breast cancer and secondary lymphedema. This observation supported our hypothesis that some cases of secondary lymphedema are conditioned by mutation in genes causing primary lymphedema influencing lymphatic development or function. This hypothesis is further supported by quantitative lymphoscintigraphy in women with secondary lymphedema following breast cancer treatment demonstrating abnormalities in the unaffected contra-lateral normal arm (Stanton A W, et al. Lymphatic drainage in the muscle and subcutis of the arm after breast cancer treatment. Breast Cancer Res Treat 2009; 117:549-57). The pre-symptomatic identification of individuals susceptible to secondary lymphedema following cancer therapy would identify a subset of patients for preventive intervention or early therapy, with the potential of ameliorating the negative effects of secondary lymphedema. We studied a series of women with breast cancer, post treatment, with and without secondary lymphedema to determine whether they carried mutations in known causal genes for primary lymphedema.

Methods

We studied 188 breast cancer patients recruited between 2000 and 2010. Blood specimens were obtained for DNA isolation and analysis. Participants were classified as cases if diagnosed with secondary lymphedema by a physician, physical therapist, or had received therapeutic treatment for lymphedema. Those without lymphedema were treated as controls.

Each participant was sequenced for the candidate lymphedema genes FLT4 (encoding VEGFR3), FOXC2, HGF, MET, GJC2 (Cx47) as previously described (Ferrell R E, et al. Candidate gene analysis in primary lymphedema. Lymphat Res Biol 2008; 6:69-76). We previously reported numbering for amino acid sequence based on the first ATG start site for human GJC2 as originally published by Uhlenberg et al. (Mutations in the gene encoding gap junction protein alpha 12 (connexin 46.6) cause Pelizaeus-Merzbacher-like disease. Am J Hum Genet. 2004; 75:251-60). There is now sufficient evidence supporting the second ATG site for initiation of translation for human GJC2 (Diekmann S, et al. Pelizaeus-Merzbacher-like disease is caused not only by a loss of connexin47 function but also by a hemichannel dysfunction. Eur J Hum Genet. 2010; 18:985-92; Orthmann-Murphy J L, et al. Loss-of-function GJA12/Connexin47 mutations cause Pelizaeus-Merzbacher-like disease. Mol Cell Neurosci 2007; 34:629-41; Ruf N, et al. Analysis of human alternative first exons and copy number variation of the GJA12 gene in patients with Pelizaeus-Merzbacher-like disease. Am J Med Genet B Neuropsychiatr Genet. 2009; 150B:226-32; and Maeda S, et al. Structure of the gap junction channel and its implications for its biological functions. Cell Mol Life Sci 2011; 68:1115-29) and we use this site for initiation of numbering the amino acid sequence. Statistical comparisons of mutation frequencies in case and control groups were performed using Fisher's exact test.

Functional Assays in Transfected HeLa Cells:

The Cx47 mutations were transfected (transient and stable) into communication deficient HeLa cells (Elfgang C, et al. Specific permeability and selective formation of gap junction channels in connexin-transfected HeLa cells. J Cell Biol 1995; 129:805-17) to determine functional changes in gap junction intercellular communication (GJIC) or connexin function. The four mutations were introduced by site directed mutagenesis into a vector containing wild type human Cx47 pIRES2-EGFP (WT-hCx47-EGFP), a gift from Dr. S. Scherer, and the fidelity of the wild type and all mutant constructs confirmed by bidirectional sequence analysis.

Immunofluorescence microscopy determines the presence or absence of Cx47 gap junction plaques when the constructs are transiently expressed in HeLa cells. A human Cx47 antibody was obtained: polyclonal rabbit against amino acids 344-399 in the cytoplasmic C-terminal tail (Orthmann-Murphy J L, et al. Mol Cell Neurosci 2007; 34:629-41); we used human CNS tissue and positive oligodendrocyte staining as a positive control and primary antibody delete as a negative control (data not shown). Cultured HeLa cells were routinely fixed and stained with the primary antibodies against Cx47, along with a nuclear marker, and transfected cells were identified by their EGFP signal. Plaques were imaged using an Olympus Fluoview 1000 confocal microscope, 100× oil objective.

Electrophysiologic characteristics of GJIC were measured between HeLa cell pairs transfected with the mutant constructs (as indicated by EGFP expression) by dual whole cell patch clamp recording. All experiments were carried out in a blinded manner. Coupling current is quantified by measuring the peak current recorded in the pair when the neighboring cell receives a 100 mV step membrane potential change (in both positive and negative directions). Step changes in membrane potential are delivered to each cell in the pair in sequence and the average current recorded in the neighboring cell determined and divided by 100 to generate coupling current expressed in pA/mV. Untransfected HeLa cells and cells transfected with empty vector (i.e., no hCx47) were used as additional controls.

The wound assay, a measure of proliferation/migration, was performed using differential interference contrast time lapse of over 24 hrs using confluent transfected HeLa cells. Analysis was done using TScratch (Geback T, et al. TScratch: a novel and simple software tool for automated analysis of monolayer wound healing assays. Biotechniques 2009; 46:265-74), mean±SEM of at least 10 positions along wound; the scrape width was normalized to the first image for each position. In all cases a two tailed student's T test was applied with $p<0.05$ considered significant.

Functional Assay in Human Lymphatic Endothelial Cells:

Adult human dermal lymphatic microvascular endothelial cells were cultured in EGM™-2 MV (both from Lonza). Cells were electroporated with 2 µg cDNA of the EGFP tagged mutant constructs and then selected with G418 as described above. Cells were microinjected using a combination (1:4 ratio) of 70 kd Texas Red dextran (Invitrogen) to mark injected cell for reference and Lucifer yellow, a known gap junction permeable dye (m.w. 443, −2 charge), to assess change in extent of spread (Abbaci M, et al. Advantages and limitations of commonly used methods to assay the molecular permeability of gap junctional intercellular communication. Biotechniques 2008; 45:33-52, 6-62). All cells were injected using constant conditions and cells were scored for dye spread in tiers from reference cell, using constant exposure time and thresholding, and were imaged using a Nikon TE2000 with temperature controlled motorized stage and QImaging Retiga CCD camera. Images were obtained using differential interference contrast (DIC) and standard filters for EGFP (identify expression of mutation), DAPI (for Lucifer yellow) and dsRed (for dextran) preinjection, immediately post-injection and 2 min after injection. Results were calculated as mean SEM and statistical significance was determined in comparison to WT-hCx47-EGFP expressing cells using a Mann-Whitney Test.

Results

Patient Characteristics and Mutation Analysis:

The characteristics of the study subjects are shown in Table 4. No significant differences were seen in demographic, clinical, or treatment variables between women who developed secondary lymphedema and controls that did not. None of the cases or controls had amino acid substitutions in the lymphedema genes FLT4 (VEGFR3), FOXC2, or HGF. A single case had a mutation in MET previously reported (Finegold D N, et al. Lymphat Res Biol 2008; 6:65-8) and was excluded from this study.

TABLE 4

Characteristics of Secondary Lymphedema Cases and Controls

|  | Cases | Controls | P |
|---|---|---|---|
| N | 80 | 108 |  |
| Age (years) Current | 60 (37-93) | 54 (22-78) | NS* |
| Age at Diagnosis (BC) | 54 (30-77) | 51 (20-74) | NS |
| Age at Diagnosis (LE) | 56 (37-82) | — |  |
| Body Mass Index | 28.6 (19.6-48.4) | 27.5 (19.2-43.9) | NS |
| Mastectomy | 33 (41%) | 51 (47%) | NS |
| Radiation | 68 (85%) | 83 (58%) | NS |
| Risk Factors |  |  |  |
| Blood draw | 7 (9%) | 21 (19%) | NS |
| Blood pressure | 9 (11%) | 18 (17%) | NS |
| Cat scratch | 7 (9%) | 20 (18%) | NS |
| Cut | 24 (30%) | 47 (44%) | NS |
| Insect bite | 22 (28%) | 24 (22%) | NS |
| Manicure | 18 (22%) | 31 (29%) | NS |
| Sun pain | 9 (11%) | 16 (15%) | NS |

*NS, no significant difference; BC, breast cancer; LE, lymphedema.

Among the 80 sequenced breast cancer patients with secondary lymphedema, we observed Cx47 mutations in four patients and observed no mutations among 108 sequenced breast cancer controls that did not develop secondary lymphedema (Table 5; p<0.03). None of the cases with mutations reported a personal or family history of primary lymphedema. Two cases (P381S and H409Y) had sisters with breast cancer and one case (H409Y) reported her sister also having secondary lymphedema following breast cancer treatment. All four women with mutations were receiving therapy for the lymphedema including bandaging, compression garments, and in one case exercise. None of them reported metastatic disease. Of note, all four women had prior surgeries including hysterectomy, cholecystectomy, knee surgery, and other procedures. They did not report lymphedema following any of these surgical procedures.

TABLE 5

Connexin 47 Mutations Seen in Secondary Lymphedema

| cDNA | Δnt | AMINO ACID | PROTEIN LOCATION | COMMENT |
|---|---|---|---|---|
| bp 436 | G→A | G146S | Intracellular loop | identified in primary lymphedema also reported in PMLD |
| bp 547 | G→T | G183C | Intracellular loop |  |
| bp 1141 | C→T | P381S | C terminal |  |
| bp 1225 | C→T | H409Y | C terminal | sister with secondary lymphedema following breast cancer |
| bp 585 | C→T | H195H | Intracellular loop | polymorphism |

Cx47 mutations were not seen among at least 298 population controls (596 alleles) (p=0.002). We identified a synonymous Cx47 polymorphism, H195H, which occurred in secondary lymphedema patients, breast cancer controls, and population controls with essentially equal frequency (5/80 secondary lymphedema patients, 8/108 breast cancer controls, and 27/298 population controls). One secondary lymphedema patient had the same mutation (G146S) seen in a family with primary lymphedema as indicated above. The other three mutations (G183C, P381S and H409Y) are unique.

The Cx47 mutations found in secondary lymphedema patients all met the following criteria for relevance of mutation status (similar to the Cx47 mutations observed in our reported primary lymphedema patients). Each mutation causes a change in the amino acid sequence of Cx47, is not present in at least 298 sequenced, ethnically matched controls (0/596 alleles), and is well conserved in mammalian evolution.

The three mutations found in probands with breast cancer and secondary lymphedema, the shared G146S mutation (by probands with primary and secondary lymphedema), and our previously identified mutations in families with primary lymphedema are distributed throughout the Cx47 monomer, although no mutations have been found in the transmembrane domains. Mutations G146S and G183C are located within the intracellular loop domain while P381S and H409Y are located in the C-terminal domain.

No single functional assay is adequate to assess the complex spectrum of connexin physiology and the effect of connexin (Cx) mutations. We used a combination of frequently used assays in HeLa cells and another assay done in human dermal LECs, the cell type we believe most likely to manifest the dysfunction causing clinical lymphedema. Each of the four mutations found in patients with secondary lymphedema have a phenotype different from that found in cells (HeLas and/or LECs) expressing WT-hCx47-EGFP.

Multiple assays for Cx function are usually performed in HeLa cells because they have little endogenous Cx expression, allowing the role of the specific Cx of interest to be isolated, and because of their ease of manipulation. The most common functional assays used utilize immunofluorescent microscopy to demonstrate the presence or absence of Cx plaques along the cell membrane between adjoining cells, dye transfer studies to document the transport of gap junction permeable dyes between cells, and measurement of electrical coupling between paired cells. Since there is increasing evidence that Cxs function independent of gap junctional communication (Laird D W. Closing the gap on autosomal dominant connexin-26 and connexin-43 mutants linked to human disease. J Biol Chem 2008; 283:2997-3001; Wei C J, et al. Connexins and cell signaling in development and disease. Annu Rev Cell Dev Biol 2004; 20:811-38; and Xu X, et al. Connexin 43-mediated modulation of polarized cell movement and the directional migration of cardiac neural crest cells. Development 2006; 133:3629-39), we also performed a wound healing assay to quantify the mutations' effects on cell migration/proliferation.

Figure 12A:
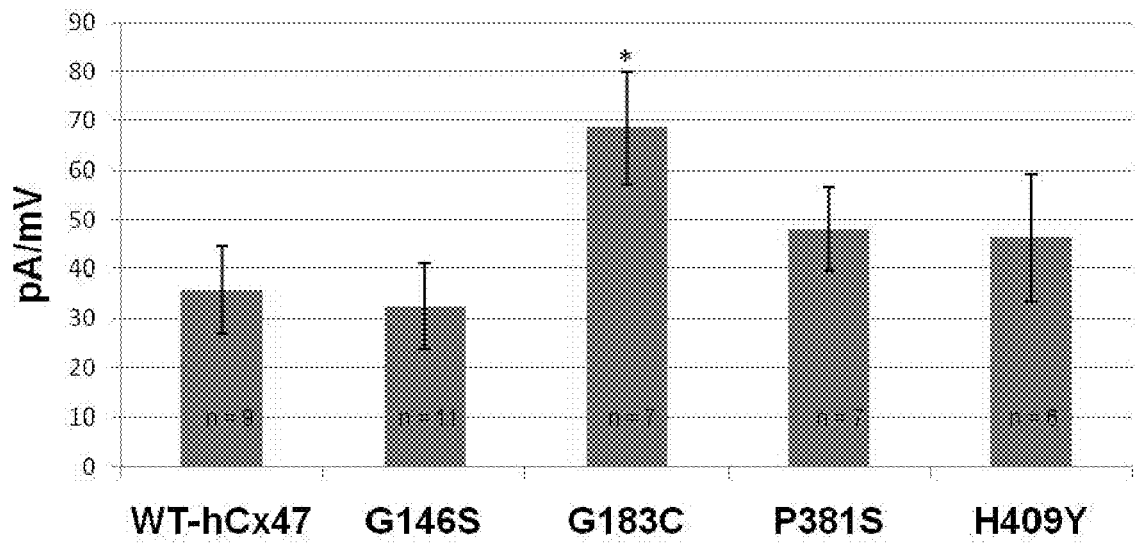
FIGS. 12A and 12C: representative transjunctional currents and average peak coupling current in HeLa cell pairs measured by dual whole cell patch clamping in response to a voltage step protocol, top right (−100 to +100 in 20 mV steps). Untransfected HeLa pairs have very little coupling current, while cell pairs expressing WT-hCX47-EGFP and mutant Cx47 G146S, P381S and H409Y are well coupled. G183C transfected pairs demonstrate increased peak coupling currents significantly different than WT-hCx47 at p<0.05, two tailed Student's t-test, *.
Figure 12B:
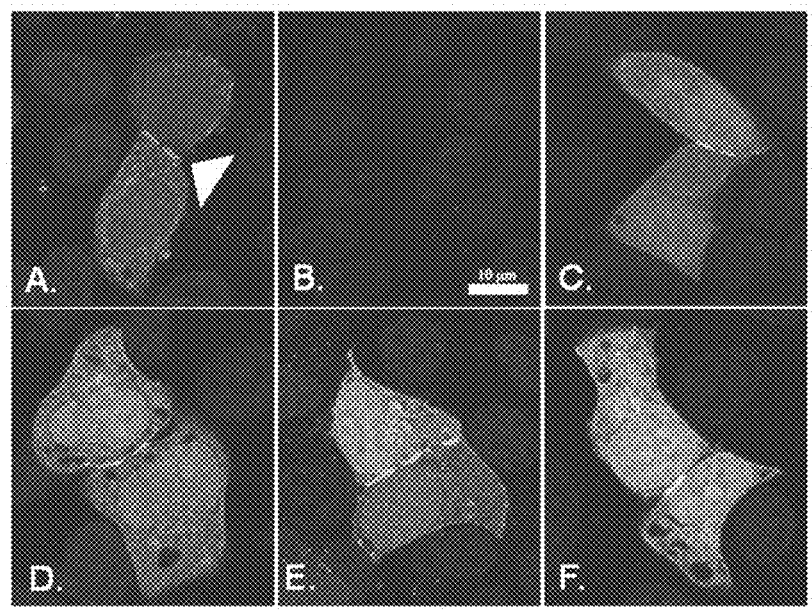
FIG. 12.
Figure 12C:
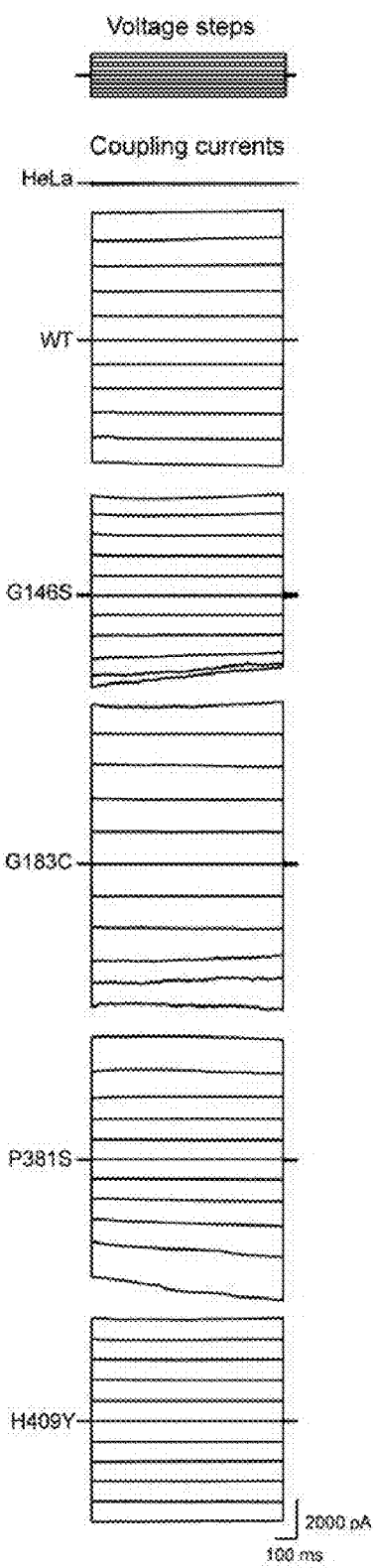

When observed by immunofluoresence confocal microscopy, HeLa cells transfected with Cx47 mutant constructs were indistinguishable from WT-hCx47 transfected cells (no plaques were detected in untransfected control HeLa cells). However, both mutations in the intracellular loop domain showed significant functional differences as compared to WT-hCx47-EGFP transfected cells. G146S transfected cells showed faster wound closure in a conventional cell scratch assay than the WT-hCx47-EGFP transfected cells (Table 6). G183C transfected cells showed increased electrical coupling (FIG. 12; Table 6) as compared to the WT-hCx47 transfected cells (Table 6). Hela cells transfected with the mutations located in the C-terminal domain (P381S and H409Y) were not functionally distinct from WT-hCx47-EGFP transfected cells.

Table 6

Summary of Functional Assessment of Mutations

|  | WT-Cx47 | G146S[1] | G183C | P381S | H409Y |
|---|---|---|---|---|---|
| LEC spread[2,3] | 1.4 ± .14 | 2.0 ± .13 | na | 2.26 ± .17 | 0.07 ± .07* |
| electrical coupling[2,4] | 35.9 ± 8.9 | 32.4 ± 8.6 | 68.6 ± 11.3* | 48.2 ± 8.6 | 46.4 ± 12.9 |
| wound assay[2,5] | 0.72 ± 0.01 | 0.62 ± 0.03* | 0.68 ± 0.16 | 0.70 ± 0.03 | 0.73 ± 0.02 |

[1]G146S mutation also found in patients with primary lymphedema.
[2]mean ± SEM.
[3]Dye spread to tiers of LECs after 2 min; significance by Mann Whitney test.
*indicates significantly different than WT-hCx47 at $p < 0.05$, two tailed Student's t-test.
[4]in pA/mV.
[5]expressed as fraction of original wound in HeLa cell monolayer after 24 hrs.

When the dye spread was evaluated in LECs expressing the human mutations the C-terminal domain mutations were also phenotypically distinguished from WT-hCx47-EGFP expressing LECs (Table 3). The H409Y mutation showed dramatically impaired dye transfer of Lucifer yellow after microinjection. In contrast, the P381S mutation showed significantly enhanced dye transfer.

Discussion

Secondary lymphedema is one of the most feared complications of breast cancer treatment. Detection of increased risk of lymphedema is particularly important given the value of preoperative assessment and early postoperative intervention in reducing the impact of secondary lymphedema. Although studies of secondary lymphedema typically use patient specific information, like age and body mass index, in evaluating the risk of secondary lymphedema, family history of lymphedema and genotype are not typically considered. A decision to intervene with treatment is usually based on the clinical burden of secondary lymphedema in the post-operative period.

Mutations leading to secondary rather than primary lymphedema might be expected to result in fairly subtle dysfunction in vitro since, clinically, no lymphedema is observed until after some significant insult in vivo, in these cases, breast cancer treatment. This is consistent with our observation that all four of the mutations show normal plaque formation when expressed in HeLa cells. The detection of plaques indicates fairly normal trafficking of the Cx proteins to the cell membrane and subsequent organization into clusters of gap junctions, i.e., plaques. Of relevance, one of these four Cx47 mutations associated with secondary lymphedema, G146S, can cause primary lymphedema when inherited as an autosomal dominant mutation with reduced penetrance. As yet unknown environmental or modifying genetic factors must influence the expression of clinically detectably lymphedema. Variation in penetrance and expression has been demonstrated for other lymphedema genes such as FLT4 and FOXC2 (Ferrell R E, et al. Hereditary lymphedema: evidence for linkage and genetic heterogeneity. Hum Mol Genet. 1998; 7:2073-8 and Finegold D N, et al. Truncating mutations in FOXC2 cause multiple lymphedema syndromes. Hum Mol Genet. 2001; 10:1185-9).

In two mutations including G146S, we detected abnormal gap junction or Cx function using in vitro assays in HeLa cells. We have documented autosomal dominant inheritance in two primary lymphedema families with Cx47 mutations and thus might expect a dominant negative effect of Cx47 mutations. However, these in vitro assays in HeLa cells are likely independent of such an effect since they have little Cx expression (Elfgang C, et al. J Cell Biol 1995; 129:805-17) (and data not shown). In the case of the G146S mutation (shared in both primary and secondary lymphedema patients), the more rapid closure in the wound closure assay as compared to WT-hCx47-EGFP transfected cells is not necessarily associated with what has previously been considered as gap junction activity: transfer of ions, small metabolites through gap junctions to adjoining cells (Xu X, et al. Development 2006; 133:3629-39). Increasingly there is evidence of Cxs' role in a large signaling complex of associated proteins which serve to regulate coordination of conventional cell-cell communication in adhesion, motility but also other basic cell processes including proliferation (Wei C J, et al. Annu Rev Cell Dev Biol 2004; 20:811-38 and Laird D W. The gap junction proteome and its relationship to disease. Trends Cell Biol 2010; 20:92-101). As shown above, we identified mutations in connexin 47 (Cx47) encoded by GJC2 as a frequent cause of primary lymphedema. This finding was confirmed by Ostergaard et al (Ostergaard P, et al. Rapid identification of mutations in GJC2 in primary lymphoedema using whole exome sequencing combined with linkage analysis with delineation of the phenotype. J Med Genet. 2011; 48:251-5). Connexins (Cxs) are the major constituents of gap junctions which mediate intercellular communication. Gap junctions form as two apposing hexamers of Cx in adjoining cells. Gap junction communication mediates the propagation of spontaneous contractions in mesenteric lymphatics (McHale N G, et al. Co-ordination of pumping in isolated bovine lymphatic vessels. J Physiol 1992; 450:503-12 and Zawieja D C, et al. Distribution, propagation, and coordination of contractile activity in lymphatics. Am J Physiol 1993; 264:H1283-91).

Functional supports for the significance of these mutations in the development of secondary lymphedema comes from abnormalities demonstrated in human dermal LECs (Table 3). Although, until recently, Cx47 expression was thought to be confined to the CNS and primarily oligodendrocytes, we demonstrated Cx47 expression in LECs along with other Cx species. Little is known about Cx expression and gap junction function in lymphatics, but there is evidence that gap junctions are important to the propagation of spontaneous contractions through mesenteric lymphatics in animal models (McHale N G, et al. J Physiol 1992; 450:503-12 and Zawieja D C, et al. Am J Physiol 1993; 264:H1283-91). We postulate that Cx47 mutations cause or contribute to the development of dermal lymphedema by impaired gap junction function causing impaired conduction of lymph from the periphery to more central lymphatic trunks. This is also supported through the identification of two Cx47 mutations in families with four limb lymphedema, one novel and one previously reported by us, where lymphoscintigraphy showed normal anatomy in distal lymphatics but impaired uptake (Ostergaard P, et al. J Med Genet. 2011; 48:251-5). Our findings of significant changes in gap junction function in LECs expressing the four mutations found in patients with secondary lymphedema: 1) confirms the significance of these mutations in patients with secondary lymphedema and 2) suggests impaired gap junction function as a novel mechanism for the development of lymphedema.

Identification of Cx47 mutations in secondary lymphedema, and previously in primary lymphedema, expands the clinical pathology of Cx47 in human disease. Until recently, Cx47 was only considered important for CNS myelination because Cx47 mutations are causal for Pelizaeus-Merzbacher-like disease (PMLD) and a milder phenotype of spastic paraplegia. These were all reported to be recessive mutations but recently dominant mutations in Cx47 were also identified as causing PMLD, among them a G146S mutation (identified as G146S, Diekmann S, et al. Eur J Hum Genet. 2010; 18:985-92). In contrast to disease caused by recessive mutations, autosomal dominant mutations in Cxs are more likely to cause syndromes in a similar fashion to the Cx43 mutations causing oculodentodigital dysplasia and the Cx26 mutations causing hearing loss and a variety of skin diseases (Laird D W. J Biol Chem 2008; 283:2997-3001). Thus, the recent identification of dominant mutations in Cx47 causing PMLD coupled with our findings of Cx47 mutations causing and/or predisposing to lymphedema suggests some patients may manifest both neurologic and lymphatic deficits.

Our finding of four independent mutations in Cx47, including one shared mutation described above, not only supports these mutations as a genetic risk to the development of secondary lymphedema but raises the likelihood that other genes may contribute to such a genetic risk to secondary lymphedema as well. Gap junctions are a multiprotein complex and our observations implicate any of these proteins as potential candidates for risk mutations and targets for drug therapy. A patient's family history of lymphedema may be useful in identifying women at higher than normal risk of developing secondary lymphedema, and sequencing of GJC2 and other genes known to cause primary lymphedema may prospectively identify a group of women who would benefit from early, aggressive surveillance and therapy prior to the clinical onset of lymphedema. Our findings challenge the commonly held view that secondary lymphedema is solely due to mechanical trauma. Genetic susceptibility is an important risk factor which must be included with mechanical trauma, radiation, and/or chemical insult. A priori recognition of such a genetic susceptibility 1) raises the potential for early detection of a group at high risk, and 2) allows the possibility of altering surgical approach and/or chemotherapy radiation therapy or direct medical treatment of the lymphedema.

The prospect of preventive intervention or pharmacological treatment in secondary lymphedema is especially attractive given the estimated prevalence of up to 600,000 women who suffer from secondary lymphedema following treatment for breast cancer, and the limited treatment options currently available to these patients. With regard to the Cx47 mutations specifically, there is potential for rapid translational progress given the ongoing effort to develop Cx modifying drugs for application to cardiovascular disease. These findings offer the possibility that early detection and intervention may be possible before breast cancer treatment is complete, and also offers the chance to ameliorate the severity of secondary lymphedema in a subset of breast cancer patients.

Whereas particular embodiments of this invention have been described above for purposes of illustration, it will be evident to those skilled in the art that numerous variations of the details of the present invention may be made without departing from the invention as defined in the appended claims.

We claim:

1. A method of detecting a mutation in a GJC2 nucleic acid comprising:
    contacting a nucleic acid sample obtained from a human patient with an oligonucleotide that specifically hybridizes to a mutant GJC2 nucleic acid comprising a T allele at position 953 of SEQ ID NO: 2 but not to a wild type GJC2 nucleic acid; and
    detecting the T allele at position 953 of SEQ ID NO: 2 in the sample when a hybrid is formed between the oligonucleotide and the mutant GJC2 nucleic acid.

2. The method of claim 1 wherein the oligonucleotide is utilized in a detection method selected from the group consisting of microarray methods, sequencing methods, hybridization methods, and amplification methods.

3. A method of identifying a functional mutation in Cx47, comprising:
    isolating a portion of GJC2 encoding a mutation in SEQ ID NO: 1 from a human patient with lymphedema;
    introducing into a cell the portion of GJC2 encoding a mutation in SEQ ID NO: 1;
    performing one or more of a plaque assay, an electric coupling assay, a wound assay and a dye spread assay on the cell; and
    determining that the mutation in GJC2 results in a functional mutation in Cx47 when the mutation alters gap junction function as measured by two or more of the assays compared to a cell comprising a sequence encoding SEQ ID NO: 1.

* * * * *

UNITED STATES PATENT AND TRADEMARK OFFICE
CERTIFICATE OF CORRECTION

| | | |
|---|---|---|
| PATENT NO. | : 9,260,754 B2 | Page 1 of 1 |
| APPLICATION NO. | : 13/106424 | |
| DATED | : February 16, 2016 | |
| INVENTOR(S) | : Catherine Baty et al. | |

It is certified that error appears in the above-identified patent and that said Letters Patent is hereby corrected as shown below:

On the title page

Column 2, Item (57) ABSTRACT, Line 6, delete "connixin" and insert -- connexin --

Signed and Sealed this
Fifth Day of July, 2016

Michelle K. Lee
*Director of the United States Patent and Trademark Office*

SEQUENCE LISTING

```
<160> NUMBER OF SEQ ID NOS: 25

<210> SEQ ID NO 1
<211> LENGTH: 436
<212> TYPE: PRT
<213> ORGANISM: Homo sapiens

<400> SEQUENCE: 1

Met Ser Trp Ser Phe Leu Thr Arg Leu Leu Glu Glu Ile His Asn His
1               5                   10                  15

Ser Thr Phe Val Gly Lys Val Trp Leu Thr Val Leu Val Val Phe Arg
            20                  25                  30

Ile Val Leu Thr Ala Val Gly Gly Glu Ala Ile Tyr Ser Asp Glu Gln
        35                  40                  45

Ala Lys Phe Thr Cys Asn Thr Arg Gln Pro Gly Cys Asp Asn Val Cys
    50                  55                  60

Tyr Asp Ala Phe Ala Pro Leu Ser His Val Arg Phe Trp Val Phe Gln
65                  70                  75                  80

Ile Val Val Ile Ser Thr Pro Ser Val Met Tyr Leu Gly Tyr Ala Val
                85                  90                  95

His Arg Leu Ala Arg Ala Ser Glu Gln Glu Arg Arg Arg Ala Leu Arg
            100                 105                 110

Arg Arg Pro Gly Pro Arg Arg Ala Pro Arg Ala His Leu Pro Pro Pro
        115                 120                 125
```

| | | | | | | | | | | | |
|---|---|---|---|---|---|---|---|---|---|---|---|
| His | Ala | Gly | Trp | Pro | Glu | Pro | Ala | Asp | Leu | Gly | Glu Glu Pro Met |
| | 130 | | | | 135 | | | | 140 | | |
| Leu | Gly | Leu | Gly | Glu | Glu | Glu | Glu | Glu | Thr | Gly | Ala Ala Glu |
| 145 | | | | | 150 | | | | | 155 | 160 |
| Gly | Ala | Gly | Glu | Glu | Ala | Glu | Glu | Ala | Gly | Ala | Glu Glu Ala Cys Thr |
| | | | 165 | | | | | 170 | | | 175 |
| Lys | Ala | Val | Gly | Ala | Asp | Gly | Lys | Ala | Ala | Gly | Thr Pro Gly Pro Thr |
| | | | 180 | | | | | 185 | | | 190 |
| Gly | Gln | His | Asp | Gly | Arg | Arg | Arg | Ile | Gln | Arg | Glu Gly Leu Met Arg |
| | | | 195 | | | | | 200 | | | 205 |
| Val | Tyr | Val | Ala | Gln | Leu | Val | Ala | Arg | Ala | Ala | Phe Glu Val Ala Phe |
| | 210 | | | | 215 | | | | | | 220 |
| Leu | Val | Gly | Gln | Tyr | Leu | Leu | Tyr | Gly | Phe | Glu | Val Arg Pro Phe Phe |
| 225 | | | | | 230 | | | | | 235 | 240 |
| Pro | Cys | Ser | Arg | Gln | Pro | Cys | Pro | His | Val | Val | Asp Cys Phe Val Ser |
| | | | | 245 | | | | | 250 | | 255 |
| Arg | Pro | Thr | Glu | Lys | Thr | Val | Phe | Leu | Leu | Val | Met Tyr Val Val Ser |
| | | | 260 | | | | | 265 | | | 270 |
| Cys | Leu | Cys | Leu | Leu | Leu | Asn | Leu | Cys | Glu | Met | Ala His Leu Gly Leu |
| | 275 | | | | | 280 | | | | 285 | |
| Gly | Ser | Ala | Gln | Asp | Ala | Val | Arg | Gly | Arg | Arg | Gly Pro Pro Ala Ser |
| | 290 | | | | 295 | | | | | 300 | |
| Ala | Pro | Ala | Pro | Ala | Pro | Arg | Pro | Pro | Cys | Ala | Phe Pro Ala Ala |
| 305 | | | | | 310 | | | | | 315 | 320 |
| Ala | Ala | Gly | Leu | Ala | Cys | Pro | Pro | Asp | Tyr | Ser | Leu Val Val Arg Ala |
| | | | | 325 | | | | | 330 | | 335 |
| Ala | Glu | Arg | Ala | Arg | Ala | His | Asp | Gln | Asn | Leu | Ala Asn Leu Ala Leu |
| | | | 340 | | | | | 345 | | | 350 |
| Gln | Ala | Leu | Arg | Asp | Gly | Ala | Ala | Gly | Asp | Arg | Asp Arg Asp Ser |
| | | 355 | | | | | 360 | | | | 365 |
| Ser | Pro | Cys | Val | Gly | Leu | Pro | Ala | Ala | Ser | Arg | Gly Pro Pro Arg Ala |
| | 370 | | | | | 375 | | | | 380 | |
| Gly | Ala | Pro | Ala | Ser | Arg | Thr | Gly | Ser | Ala | Thr | Ser Ala Gly Thr Val |
| 385 | | | | | 390 | | | | | 395 | 400 |
| Gly | Glu | Gln | Gly | Arg | Pro | Gly | Thr | His | Glu | Arg | Pro Gly Ala Lys Pro |
| | | | | 405 | | | | | 410 | | 415 |
| Arg | Ala | Gly | Ser | Glu | Lys | Gly | Ser | Ala | Ser | Ser | Arg Asp Gly Lys Thr |
| | | | 420 | | | | | 425 | | | 430 |
| Thr | Val | Trp | Ile | | | | | | | | |
| | | | 435 | | | | | | | | |

<210> SEQ ID NO 2
<211> LENGTH: 2259
<212> TYPE: DNA
<213> ORGANISM: Homo sapiens

<400> SEQUENCE: 2

```
ggggaacaat ggggcccttg agggcccctc ctccagcccc cattgtgctt ggtggtgaga       60
ggtggccctg gctcggccac acaccctcgg ggaggaccag catccaagca ggtggaaggg      120
ctctgaggga gactggaatt ttctggcctg gagaaggacc cgcccgcccg cccctatgac      180
caacatgagc tggagcttcc tgacgcggct gctggaggag atccacaacc actccacctt      240
cgtgggcaag gtgtggctca ggtgctggt ggtcttccgc atcgtgctga cggctgtggg      300
cggcgaggcc atctactcgg acgagcaggc caagttcact tgcaacacgc ggcagccagg      360
```

```
ctgcgacaac gtctgctatg acgccttcgc gccctgtcg cacgtgcgct tctgggtctt    420
ccagattgtg gtcatctcca cgccctcggt catgtacctg ggctacgccg tgcaccgcct    480
ggcccgtgcg tctgagcagg agcggcgccg cgccctccgc cgccgcccgg ggccacgccg    540
cgcgccccga gcgcacctgc cgccccgca cgccggctgg cctgagcccg ccgacctggg    600
cgaggaggag cccatgctgg gcctgggcga ggaggaggag gaggaggaga cggggcagc    660
cgagggcgcc ggcgaggaag cggaggaggc aggcgcggag gaggcgtgca ctaaggcggt    720
cggcgctgac ggcaaggcgg cagggacccc gggcccgacc gggcaacacg atgggcggag    780
gcgcatccag cgggagggcc tgatgcgcgt gtacgtggcc cagctggtgg ccagggcagc    840
tttcgaggtg gccttcctgg tgggccagta cctgctgtac ggcttcgagg tgcgaccgtt    900
cttccctgc agccgccagc cctgcccgca cgtggtggac tgcttcgtgt cgcgccctac    960
tgaaaagacg gtcttcctgc tggttatgta cgtggtcagc tgcctgtgcc tgctgctcaa   1020
cctctgtgag atggcccacc tgggcttggg cagcgcgcag gacgcggtgc gcggccgccg   1080
cggcccccg gcctccgccc ccgccccgc gccgcggccc ccgccctgcg ccttccctgc    1140
ggcggccgct ggcttggcct gcccgccgga ctacagcctg gtggtgcggg cggccgagcg   1200
cgctcgggcg catgaccaga acctggcaaa cctggccctg caggcgctgc gcgacggggc   1260
agcggctggg gaccgcgacc gggacagttc gccgtgcgtc ggcctccctg cggcctcccg   1320
ggggccccc agagcaggcg ccccgcgtc ccggacgggc agtgctacct ctgcgggcac    1380
tgtcggggag cagggccggc ccggcaccca cgagcggcca ggagccaagc ccagggctgg   1440
ctccgagaag ggcagtgcca gcagcaggga cgggaagacc accgtgtgga tctgagggcg   1500
ctggcttgcg agctgggcca gggaggagga gggttggggg gctccggtgg aaacctgcga   1560
ccccttctcc tcagccttct ccttagccgg tggcctcagg cagactctgc ccagaggggc   1620
agccaggctg ctcagggaag gggctgaaag cggcagagga gtgccctggc ttggtcacca   1680
ctggggccaa ggtgggtgg agagaggcct aggagccaga aagggccctc tgctgtggtc   1740
tgaaccccag gggagtgggg gcattgactc caccctgtc ctgagctgga ataggtcctc   1800
tgggatgcca gctctcccct ttgtgcttcc ctgcagcaac ccatggaggg cccagggtgc   1860
ctggtatggg catcagttgg tggggtgcg ggggtgcgtg tccccattcc ctgcaacagc   1920
aaatggggct ccttcttcag ccctcccctt cccagcccca aactgagaca gactgggagc   1980
tgggagcctg gggtggacag gaccataccc tctttgagct tctgcgatgc cggccttccg   2040
ttcctctggg aggcttgaag ttctgcaaag atgttgatat gccttgcagc ttggacccaa   2100
tgggtggtgg tcagggcctg ggggcttggc catgctgggg gaatgggct ctgggttcct    2160
gcctgtggcc tgtctgtcct cctccctaat tcagacccag cctcaagagg aaagggagta   2220
aaataaaact aacttgttta taaaaaaaaa aaaaaaaa                            2259
```

<210> SEQ ID NO 3
<211> LENGTH: 333
<212> TYPE: PRT
<213> ORGANISM: Homo sapiens

<400> SEQUENCE: 3

Met Gly Asp Trp Gly Phe Leu Glu Lys Leu Leu Asp Gln Val Gln Glu
1               5                   10                  15

His Ser Thr Val Val Gly Lys Ile Trp Leu Thr Val Leu Phe Ile Phe
            20                  25                  30

```
Arg Ile Leu Ile Leu Gly Leu Ala Gly Glu Ser Val Trp Gly Asp Glu
             35                  40                  45
Gln Ser Asp Phe Glu Cys Asn Thr Ala Gln Pro Gly Cys Thr Asn Val
 50                  55                  60
Cys Tyr Asp Gln Ala Phe Pro Ile Ser His Ile Arg Tyr Trp Val Leu
 65                  70                  75                  80
Gln Phe Leu Phe Val Ser Thr Pro Thr Leu Val Tyr Leu Gly His Val
                 85                  90                  95
Ile Tyr Leu Ser Arg Arg Glu Glu Arg Leu Arg Gln Lys Glu Gly Glu
            100                 105                 110
Leu Arg Ala Leu Pro Ala Lys Asp Pro Gln Val Glu Arg Ala Leu Ala
            115                 120                 125
Ala Val Glu Arg Gln Met Ala Lys Ile Ser Val Ala Glu Asp Gly Arg
130                 135                 140
Leu Arg Ile Arg Gly Ala Leu Met Gly Thr Tyr Val Ala Ser Val Leu
145                 150                 155                 160
Cys Lys Ser Val Leu Glu Ala Gly Phe Leu Tyr Gly Gln Trp Arg Leu
                165                 170                 175
Tyr Gly Trp Thr Met Glu Pro Val Phe Val Cys Gln Arg Ala Pro Cys
            180                 185                 190
Pro Tyr Leu Val Asp Cys Phe Val Ser Arg Pro Thr Glu Lys Thr Ile
            195                 200                 205
Phe Ile Ile Phe Met Leu Val Val Gly Leu Ile Ser Leu Val Leu Asn
210                 215                 220
Leu Leu Glu Leu Val His Leu Leu Cys Arg Cys Leu Ser Arg Gly Met
225                 230                 235                 240
Arg Ala Arg Gln Gly Gln Asp Ala Pro Pro Thr Gln Gly Thr Ser Ser
                245                 250                 255
Asp Pro Tyr Thr Asp Gln Val Phe Phe Tyr Leu Pro Val Gly Gln Gly
            260                 265                 270
Pro Ser Ser Pro Pro Cys Pro Thr Tyr Asn Gly Leu Ser Ser Ser Glu
            275                 280                 285
Gln Asn Trp Ala Asn Leu Thr Thr Glu Glu Arg Leu Ala Ser Ser Arg
290                 295                 300
Pro Pro Leu Phe Leu Asp Pro Pro Gln Asn Gly Gln Lys Pro Pro
305                 310                 315                 320
Ser Arg Pro Ser Ser Ser Ala Ser Lys Lys Gln Tyr Val
                325                 330

<210> SEQ ID NO 4
<211> LENGTH: 1710
<212> TYPE: DNA
<213> ORGANISM: Homo sapiens

<400> SEQUENCE: 4
cagcagggct cccgcgggcg tcactccggc catcgtcccc acctccacct gggccgcccg      60
gcaggcaggc gacggaggcc cgggagccat gggtgactgg ggcttcctgg agaagttgct     120
ggaccaggtc caggagcact cgaccgtggt gggtaagatc tggctgacgg tgctcttcat     180
cttccgcatc ctcatcctgg gcctggccgg cgagtcagtg tggggtgacg agcaatcaga     240
tttcgagtgt aacacggccc agccaggctg caccaacgtc tgctatgacc aggccttccc     300
catctcccac atccgctact gggtgctgca gttcctcttc gtcagcacac ccaccctggt     360
ctacctgggc catgtcattt acctgtctcg gcgagaagag cggctgcggc agaaggaggg     420
```

-continued

```
ggagctgcgg gcactgccgg ccaaggaccc acaggtggag cgggcgctgg cggccgtaga      480
gcgtcagatg gccaagatct cggtggcaga agatggtcgc ctgcgcatcc gcggagcact      540
gatgggcacc tatgtcgcca gtgtgctctg caagagtgtg ctagaggcag cttcctcta      600 tggccagtgg cgcctgtacg gctggaccat ggagcccgtg tttgtgtgcc agcgagcacc      660
ctgcccctac ctcgtggact gctttgtctc tcgcccacg gagaagacca tcttcatcat       720
cttcatgttg gtggttggac tcatctccct ggtgcttaac ctgctggagt tggtgcacct      780
gctgtgtcgc tgcctcagcc gggggatgag ggcacggcaa ggccaagacg cacccccgac      840
ccagggcacc tcctcagacc cttacacgga ccaggtcttc ttctacctcc ccgtgggcca      900
ggggccctca tccccaccat gccccaccta caatgggctc tcatccagtg agcagaactg      960
ggccaacctg accacagagg agaggctggc gtcttccagg ccccctctct tcctggaccc     1020
accccctcag aatggccaaa aaccccaag tcgtcccagc agctctgctt ctaagaagca      1080
gtatgtatag aggcctgtgg cttatgtcac ccaacagagg ggtcctgaga agtctggctg     1140
cctgggatgc cccctgcccc ctcctggaag gctctgcaga gatgactggg ctggggaagc     1200
aggtgcttgc tggccatgga gcctcattgc aagttgttct tgaacacctg aggccttcct     1260
ggtgcccacc aggcactacg gcttcctctc cagaatgtgg ctttgcctga gcacagacag     1320
agtcagcatg gaatgctctt ggccaagggt actggggcc ctctggcctt ttgcagctga      1380
tccagaggaa cccagagcca acttacccca acctcaccct atggaacagt cacctgtgcg     1440
caggttgtcc tcaaaccctc tcctcacagg aaaaggcgga ttgaggctgc tgggtcagcc     1500
ttgatcgcac agacagagct tgtgccggat ttggccctgt caaggggact ggtgccttgt     1560
tttcatcact ccttcctagt tctactgttc aagcttctga aataaacagg acttgatcac     1620
aaaaaaaaaa aaaaaaaaaa aaaaaaaaaa aaaaaaaaaa aaaaaaaaaa aaaaaaaaaa     1680
aaaaaaaaaa aaaaaaaaaa aaaaaaaaaa                                       1710
```

<210> SEQ ID NO 5
<211> LENGTH: 382
<212> TYPE: PRT
<213> ORGANISM: Homo sapiens

<400> SEQUENCE: 5

```
Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140
```

| Val | Lys | Met | Arg | Gly | Gly | Leu | Leu | Arg | Thr | Tyr | Ile | Ile | Ser | Ile | Leu |
| 145 | | | | | 150 | | | | | 155 | | | | | 160 |

Phe Lys Ser Ile Phe Glu Val Ala Phe Leu Leu Ile Gln Trp Tyr Ile
                    165                          170                        175

Tyr Gly Phe Ser Leu Ser Ala Val Tyr Thr Cys Lys Arg Asp Pro Cys
                    180                          185                        190

Pro His Gln Val Asp Cys Phe Leu Ser Arg Pro Thr Glu Lys Thr Ile
        195                          200                        205

Phe Ile Ile Phe Met Leu Val Val Ser Leu Val Ser Leu Ala Leu Asn
210                              215                        220

Ile Ile Glu Leu Phe Tyr Val Phe Phe Lys Gly Val Lys Asp Arg Val
225                    230                        235                        240

Lys Gly Lys Ser Asp Pro Tyr His Ala Thr Ser Gly Ala Leu Ser Pro
                    245                          250                        255

Ala Lys Asp Cys Gly Ser Gln Lys Tyr Ala Tyr Phe Asn Gly Cys Ser
                    260                          265                        270

Ser Pro Thr Ala Pro Leu Ser Pro Met Ser Pro Gly Tyr Lys Leu
        275                          280                        285

Val Thr Gly Asp Arg Asn Asn Ser Ser Cys Arg Asn Tyr Asn Lys Gln
290                              295                        300

Ala Ser Glu Gln Asn Trp Ala Asn Tyr Ser Ala Glu Gln Asn Arg Met
305                    310                        315                        320

Gly Gln Ala Gly Ser Thr Ile Ser Asn Ser His Ala Gln Pro Phe Asp
                    325                          330                        335

Phe Pro Asp Asp Asn Gln Asn Ser Lys Lys Leu Ala Ala Gly His Glu
                    340                          345                        350

Leu Gln Pro Leu Ala Ile Val Asp Gln Arg Pro Ser Ser Arg Ala Ser
        355                          360                        365

Ser Arg Ala Ser Ser Arg Pro Arg Pro Asp Asp Leu Glu Ile
370                              375                        380

<210> SEQ ID NO 6
<211> LENGTH: 3130
<212> TYPE: DNA
<213> ORGANISM: Homo sapiens

<400> SEQUENCE: 6

```
gagtcagtgg cttgaaactt ttaaaagctc tgtgctccaa gttacaaaaa gcttttacg     60 aggtatcagc acttttcttt cattaggggg aaggcgtgag gaaagtacca acagcagcg    120 gagttttaaa cttaaatag acaggtctga gtgcctgaac ttgccttttc attttacttc    180
atcctccaag gagttcaatc acttggcgtg acttcactac ttttaagcaa agagtggtg    240 cccaggcaac atgggtgact ggagcgcctt aggcaaactc cttgacaagg ttcaagccta    300
ctcaactgct ggagggaagg tgtggctgtc agtactttc attttccgaa tcctgctgct    360
ggggacagcg gttgagtcag cctggggaga tgagcagtct gcctttcgtt gtaacactca    420
gcaacctggt tgtgaaaatg tctgctatga caagtctttc ccaatctctc atgtgcgctt    480
ctgggtcctg cagatcatat ttgtgtctgt acccacactc ttgtacctgg ctcatgtgtt    540
ctatgtgatg cgaaaggaag agaaactgaa caagaaagag gaagaactca aggttgccca    600
aactgatggt gtcaatgtgg acatgcactt gaagcagatt gagataaaga gttcaagta    660 cggtattgaa gagcatggta aggtgaaaat gcgagggggg ttgctgcgaa cctacatcat    720
cagtatcctc ttcaagtcta tctttgaggt ggccttcttg ctgatccagt ggtacatcta    780
```

```
tggattcagc ttgagtgctg tttacacttg caaaagagat ccctgcccac atcaggtgga        840 ctgttttcctc tctcgcccca cggagaaaac catcttcatc atcttcatgc tggtggtgtc        900
cttggtgtcc ctggccttga atatcattga actcttctat gttttcttca agggcgttaa        960
ggatcgggtt aagggaaaga gcgacccttta ccatgcgacc agtggtgcgc tgagccctgc       1020
caaagactgt gggtctcaaa atatgctta tttcaatggc tgctcctcac caaccgctcc        1080
cctctcgcct atgtctcctc ctgggtacaa gctggttact ggcgacagaa acaattcttc       1140
ttgccgcaat tacaacaagc aagcaagtga gcaaaactgg gctaattaca gtgcagaaca       1200
aaatcgaatg gggcaggcgg gaagcaccat ctctaactcc catgcacagc cttttgattt       1260
ccccgatgat aaccagaatt ctaaaaaact agctgctgga catgaattac agccactagc       1320
cattgtggac cagcgacctt caagcagagc cagcagtcgt gccagcagca gacctcggcc       1380
tgatgacctg gagatctaga tacaggcttg aaagcatcaa gattccactc aattgtggag       1440
aagaaaaaag gtgctgtaga aagtgcacca ggtgttaatt ttgatccggt ggaggtggta       1500
ctcaacagcc ttattcatga ggcttagaaa acacaaagac attagaatac ctaggttcac       1560
tgggggtgta tggggtagat gggtggagag ggaggggata agagaggtgc atgttggtat       1620
ttaaagtagt ggattcaaag aacttagatt ataaataaga gttccattag gtgatacata       1680
gataagggct ttttctcccc gcaaacaccc ctaagaatgg ttctgtgtat gtgaatgagc       1740
gggtggtaat tgtggctaaa tatttttgtt ttaccaagaa actgaaataa ttctggccag       1800
gaataaatac ttcctgaaca tcttaggtct tttcaacaag aaaaagacag aggattgtcc       1860
ttaagtccct gctaaaacat tccattgtta aaatttgcac tttgaaggta agctttctag       1920
gcctgaccct ccaggtgtca atggacttgt gctactatat ttttttattc ttggtatcag       1980
tttaaaattc agacaaggcc cacagaataa gattttccat gcatttgcaa atacgtatat       2040 tcttttttcca tccacttgca caatatcatt accatcactt tttcatcatt cctcagctac       2100
tactcacatt catttaatgg tttctgtaaa cattttaag acagttggga tgtcacttaa       2160 cattttttttt ttgagctaaa gtcagggaat caagccatgc ttaatattta acaatcactt       2220
atatgtgtgt cgaagagttt gttttgtttg tcatgtattg gtacaagcag atacagtata       2280
aactcacaaa cacagatttg aaaataatgc acatatggtg ttcaaatttg aacctttctc       2340
atggattttt gtggtgtggg ccaatatggt gtttacatta taattcct gctgtggcaa       2400 gtaaagcaca cttttttttt ctcctaaaat gttttttccct gtgtatccta ttatggatac       2460
tggttttgtt aattatgatt ctttatttttc tctccttttt ttaggatata gcagtaatgc       2520
tattactgaa atgaatttcc tttttctgaa atgtaatcat tgatgcttga atgatagaat       2580
tttagtactg taaacaggct ttagtcatta atgtgagaga cttagaaaaa atgcttagag       2640
tggactatta aatgtgccta aatgaatttt gcagtaactg gtattcttgg gttttcctac       2700
ttaatacaca gtaattcaga acttgtattc tattatgagt ttagcagtct tttggagtga       2760
ccagcaactt tgatgtttgc actaagattt tatttggaat gcaagagagg ttgaaagagg       2820
attcagtagt acacatacaa ctaatttatt tgaactatat gttgaagaca tctaccagtt       2880
tctccaaatg cctttttttaa aactcatcac agaagattgg tgaaaatgct gagtatgaca       2940
cttttcttct tgcatgcatg tcagctacat aaacagtttt gtacaatgaa aattactaat       3000
ttgtttgaca ttccatgtta aactacggtc atgttcagct tcattgcatg taatgtagac       3060
ctagtccatc agatcatgtg ttctggagag tgttctttat tcaataaagt tttaatttag       3120
tataaacata                                                              3130
```

<210> SEQ ID NO 7
<211> LENGTH: 358
<212> TYPE: PRT
<213> ORGANISM: Homo sapiens

<400> SEQUENCE: 7

```
Met Gly Asp Trp Ser Phe Leu Gly Asn Phe Leu Glu Val His Lys
1               5                   10                  15

His Ser Thr Val Val Gly Lys Val Trp Leu Thr Val Leu Phe Ile Phe
                20                  25                  30

Arg Met Leu Val Leu Gly Thr Ala Ala Glu Ser Ser Trp Gly Asp Glu
            35                  40                  45

Gln Ala Asp Phe Arg Cys Asp Thr Ile Gln Pro Gly Cys Gln Asn Val
        50                  55                  60

Cys Tyr Asp Gln Ala Phe Pro Ile Ser His Ile Arg Tyr Trp Val Leu
65                  70                  75                  80

Gln Ile Ile Phe Val Ser Thr Pro Ser Leu Val Tyr Met Gly His Ala
                85                  90                  95

Met His Thr Val Arg Met Gln Glu Lys Arg Lys Leu Arg Glu Ala Glu
            100                 105                 110

Arg Ala Lys Glu Val Arg Gly Ser Gly Ser Tyr Glu Tyr Pro Val Ala
        115                 120                 125

Glu Lys Ala Glu Leu Ser Cys Trp Glu Glu Gly Asn Gly Arg Ile Ala
130                 135                 140

Leu Gln Gly Thr Leu Leu Asn Thr Tyr Val Cys Ser Ile Leu Ile Arg
145                 150                 155                 160

Thr Thr Met Glu Val Gly Phe Ile Val Gly Gln Tyr Phe Ile Tyr Gly
                165                 170                 175

Ile Phe Leu Thr Thr Leu His Val Cys Arg Arg Ser Pro Cys Pro His
            180                 185                 190

Pro Val Asn Cys Tyr Val Ser Arg Pro Thr Glu Lys Asn Val Phe Ile
        195                 200                 205

Val Phe Met Leu Ala Val Ala Ala Leu Ser Leu Leu Leu Ser Leu Ala
210                 215                 220

Glu Leu Tyr His Leu Gly Trp Lys Lys Ile Arg Gln Arg Phe Val Lys
225                 230                 235                 240

Pro Arg Gln His Met Ala Lys Cys Gln Leu Ser Gly Pro Ser Val Gly
                245                 250                 255

Ile Val Gln Ser Cys Thr Pro Pro Asp Phe Asn Gln Cys Leu Glu
            260                 265                 270

Asn Gly Pro Gly Gly Lys Phe Phe Asn Pro Phe Ser Asn Asn Met Ala
        275                 280                 285

Ser Gln Gln Asn Thr Asp Asn Leu Val Thr Glu Gln Val Arg Gly Gln
290                 295                 300

Glu Gln Thr Pro Gly Glu Gly Phe Ile Gln Val Arg Tyr Gly Gln Lys
305                 310                 315                 320

Pro Glu Val Pro Asn Gly Val Ser Pro Gly His Arg Leu Pro His Gly
                325                 330                 335

Tyr His Ser Asp Lys Arg Leu Ser Lys Ala Ser Lys Ala Arg
            340                 345                 350

Ser Asp Asp Leu Ser Val
        355
```

```
<210> SEQ ID NO 8
<211> LENGTH: 3177
<212> TYPE: DNA
<213> ORGANISM: Homo sapiens

<400> SEQUENCE: 8 attaaaaga cggtggaaga ggaacaactg acaggctcaa gagcaaaaag cgtgggcagt      60
tggagaagaa gcagccagag tgtgaagaag cccacggaag gaaagtccag ggaggaggaa     120
aagaagcaga agttttggca tctgttccct ggctgtgcca agatgggcga ttggagcttc     180
ctgggaaatt tcctggagga agtacacaag cactcgaccg tggtaggcaa ggtctggctc     240
actgtcctct tcatattccg tatgctcgtg ctgggcacag ctgctgagtc ttcctggggg     300
gatgagcagg ctgatttccg gtgtgatacg attcagcctg gctgccagaa tgtctgctac     360
gaccaggctt cccccatctc ccacattcgc tactgggtgc tgcagatcat cttcgtctcc     420
acgccctctc tggtgtacat gggccacgcc atgcacactg tgcgcatgca ggagaagcgc     480
aagctacggg aggccgagag gccaaagagg tccggggct ctggctctta cgagtacccg     540
gtggcagaga aggcagaact gtcctgctgg gaggaaggga tggaaggat tgccctccag     600 ggcactctgc tcaacaccta tgtgtgcagc atcctgatcc gcaccaccat ggaggtgggc     660
ttcattgtgg gccagtactt catctacgga atcttcctga ccaccctgca tgtctgccgc     720
aggagtccct gtccccaccc ggtcaactgt tacgtatccc ggcccacaga gaagaatgtc     780
ttcattgtct ttatgctggc tgtggctgca ctgtccctcc tccttagcct ggctgaactc     840
taccacctgg gctggaagaa gatcagacag cgatttgtca aaccgcggca gcacatggct     900
aagtgccagc tttctggccc ctctgtgggc atagtccaga gctgcacacc cccccccgac     960
tttaatcagt gcctggagaa tggccctggg ggaaaattct tcaatccctt cagcaataat    1020
atggcctccc aacaaaacac agacaacctg gtcaccgagc aagtacgagg tcaggagcag    1080
actcctgggg aaggtttcat ccaggttcgt tatggccaga agcctgaggt gcccaatgga    1140
gtctcaccag gtcaccgcct tcccccatggc tatcatagtg acaagcgacg tcttagtaag    1200
gccagcagca aggcaaggtc agatgaccta tcagtgtgac cctcctttat gggaggatca    1260
ggaccaggtg ggaacaaagg aggctcagag aagaaagacg tgtcccttct gaactgatgc    1320
tttctcactg tcatcactgc ttggctcctt tgagccccgg gtctcaatga cgttgctcat    1380
taattctaga aactataacc agggctctgg gatagtaaga gaggtgacaa cccacccaga    1440
ctgcagttcc ctccccaccc tctacccagt atacgaagcc tttcagatta ctcatgaaac    1500
agggtagagg gaaagaaggg aagcatggca aaagctggcc tggaagggat agccagaggg    1560
atagaatgac tctctctcta cataccagca gcataccaaa tgcgttctct aagttcctac    1620
ctccttgacc tgatcaccct ccctcctcca aggaagagct caaagttccc agccaataga    1680
cagcatgaat caaggaactt gcattatatg tgctcttgaa tctgttgtct ccatggacca    1740
ttcctcggag tagtggtgag atggccttgg gttgccttg gcttctcctc cctctactca    1800 gcccttaaaaa gggcttcttg gaactttacc agcagcctca gctttacaaa tgccttggta    1860
tgtacctctg gcaaatgccc caccttggtg atgttgcaac cttccttct gctagggtgt    1920 acacctagcc tgtgcaggtg tcagccctgc tagggagtca ctgtacacac aaactctact    1980
ggaattcctg ccaacatctg tcaccctgca gctccttac agttcaatcc aatgatagaa    2040
accatccctt cccttctcc cttggctgtt cacccagcca ttccctgaag gcttaccaa     2100 caggaatatc caagaagctg ttgtcccctc tcgaaccctg accagatcat cagccactga    2160
```

-continued

```
ggccagtgga atttccccag gccttgttaa acaaagaaa gcattgtacc tctcagattc   2220
cccttgtgga aaaaaaaatt ctgctgtgaa gatgaaaata aaaatggaga gaaacactg    2280
gaaaactatt ttcccctcct atttacttcc tttgctgact gccaacttag tgccaagagg   2340
aggtgtgatg acagctatgg aggccccag atctctctct cctggaggct ttagcagggg    2400
caaggaaata gtagggaat ctccagctct cttggcaggg cctttattta aagagcgcag    2460
agattcctat gtctccctag tgccctaat gagactgcca agtgggggct gtagaaaagc    2520
cttgccttcc ccagggattg gcctggtctc tgtattcact ggatccataa tgggttgctg    2580
ttgtttgga tgaaggtaaa cgatgcttgg aattggaaac tgagacttat agagggatta    2640
ttacattatt aaaatgcacg tgtgtgtgtg tgtgggtgct gatgggatgg gtaaaggctt    2700
ggggagtcct gaataagga aaggaaacca cagagaaact tgtgtcttcc tgctctcctc     2760
tccggctgcc tggcagttat taacctaaac agatagccac aagaggttgg gacagaggag    2820
ggtaaaggct cagaaggagg ttcaacctct gactcacctg cccatctctg ggccctctgc    2880
tgacacttgg atgctattgt tgggtggaaa gataaatgag agtggagagg tggaggaaag    2940
tgactaggat gccatttagg aaggaatgtc tgatcatccc gggtccctgg aggggacacc    3000
ttttaatcta ttgcctagca ttaatatttt ctctccttct atctctgaaa tgttttatga    3060
aatgagtgtt cttgaattag aaattctgtg ggatcaatct ttgatggtga gggttttaga    3120
aaggaaaaat atagtaaaat gtgtaatttg tcttaataaa atctatctct acatcta       3177
```

<210> SEQ ID NO 9
<211> LENGTH: 439
<212> TYPE: PRT
<213> ORGANISM: Homo sapiens

<400> SEQUENCE: 9

```
Met Thr Asn Met Ser Trp Ser Phe Leu Thr Arg Leu Leu Glu Glu Ile
1               5                   10                  15

His Asn His Ser Thr Phe Val Gly Lys Val Trp Leu Thr Val Leu Val
            20                  25                  30

Val Phe Arg Ile Val Leu Thr Ala Val Gly Gly Glu Ala Ile Tyr Ser
        35                  40                  45

Asp Glu Gln Ala Lys Phe Thr Cys Asn Thr Arg Gln Pro Gly Cys Asp
    50                  55                  60

Asn Val Cys Tyr Asp Ala Phe Ala Pro Leu Ser His Val Arg Phe Trp
65                  70                  75                  80

Val Phe Gln Ile Val Ile Ser Thr Pro Ser Val Met Tyr Leu Gly
            85                  90                  95

Tyr Ala Val His Arg Leu Ala Arg Ala Ser Glu Gln Glu Arg Arg Arg
            100                 105                 110

Ala Leu Arg Arg Arg Pro Gly Pro Arg Arg Ala Pro Arg Ala His Leu
        115                 120                 125

Pro Pro His Ala Gly Trp Pro Glu Pro Ala Asp Leu Gly Glu Glu
    130                 135                 140

Glu Pro Met Leu Gly Leu Gly Glu Glu Glu Glu Glu Thr Gly
145                 150                 155                 160

Ala Ala Glu Gly Ala Gly Glu Glu Ala Glu Ala Gly Ala Glu Glu
            165                 170                 175

Ala Cys Thr Lys Ala Val Gly Ala Asp Gly Lys Ala Ala Gly Thr Pro
        180                 185                 190

Gly Pro Thr Gly Gln His Asp Gly Arg Arg Arg Ile Gln Arg Glu Gly
```

```
                195                 200                 205
Leu Met Arg Val Tyr Val Ala Gln Leu Val Ala Arg Ala Ala Phe Glu
    210                 215                 220

Val Ala Phe Leu Val Gly Gln Tyr Leu Leu Tyr Gly Phe Glu Val Arg
225                 230                 235                 240

Pro Phe Phe Pro Cys Ser Arg Gln Pro Cys Pro His Val Val Asp Cys
                245                 250                 255

Phe Val Ser Arg Pro Thr Glu Lys Thr Val Phe Leu Leu Val Met Tyr
            260                 265                 270

Val Val Ser Cys Leu Cys Leu Leu Asn Leu Cys Glu Met Ala His
        275                 280                 285

Leu Gly Leu Gly Ser Ala Gln Asp Ala Val Arg Gly Arg Gly Pro
    290                 295                 300

Pro Ala Ser Ala Pro Ala Pro Arg Pro Pro Cys Ala Phe
305                 310                 315                 320

Pro Ala Ala Ala Gly Leu Ala Cys Pro Pro Asp Tyr Ser Leu Val
                325                 330                 335

Val Arg Ala Ala Glu Arg Ala Arg Ala His Asp Gln Asn Leu Ala Asn
            340                 345                 350

Leu Ala Leu Gln Ala Leu Arg Asp Gly Ala Ala Gly Asp Arg Asp
        355                 360                 365

Arg Asp Ser Ser Pro Cys Val Gly Leu Pro Ala Ala Ser Arg Gly Pro
370                 375                 380

Pro Arg Ala Gly Ala Pro Ala Ser Arg Thr Gly Ser Ala Thr Ser Ala
385                 390                 395                 400

Gly Thr Val Gly Glu Gln Gly Arg Pro Gly Thr His Glu Arg Pro Gly
                405                 410                 415

Ala Lys Pro Arg Ala Gly Ser Glu Lys Gly Ser Ala Ser Ser Arg Asp
            420                 425                 430

Gly Lys Thr Thr Val Trp Ile
        435

<210> SEQ ID NO 10
<211> LENGTH: 439
<212> TYPE: PRT
<213> ORGANISM: Pan troglodytes

<400> SEQUENCE: 10

Met Thr Asn Met Ser Trp Ser Phe Leu Thr Arg Leu Leu Glu Glu Ile
1               5                   10                  15

His Asn His Ser Thr Phe Val Gly Lys Val Trp Leu Thr Val Leu Val
                20                  25                  30

Val Phe Arg Ile Val Leu Thr Ala Val Gly Gly Glu Ala Ile Tyr Ser
            35                  40                  45

Asp Glu Gln Ala Lys Phe Thr Cys Asn Thr Arg Gln Pro Gly Cys Asp
    50                  55                  60

Asn Val Cys Tyr Asp Ala Phe Ala Pro Leu Ser His Val Arg Phe Trp
65                  70                  75                  80

Val Phe Gln Ile Val Val Ile Ser Thr Pro Ser Val Met Tyr Leu Gly
                85                  90                  95

Tyr Ala Val His Arg Leu Ala Arg Ala Ser Glu Gln Glu Arg Arg Arg
                100                 105                 110

Ala Leu Arg Arg Arg Pro Gly Pro Arg Arg Ala Pro Arg Ala His Leu
            115                 120                 125
```

```
Pro Pro Pro His Ala Gly Trp Pro Glu Pro Ala Asp Leu Gly Glu Glu
        130                 135                 140

Glu Pro Met Leu Gly Leu Gly Glu Glu Glu Glu Glu Glu Thr Gly
145                 150                 155                 160

Ala Ala Glu Gly Ala Gly Glu Glu Ala Glu Ala Gly Ala Glu Glu
                165                 170                 175

Ala Cys Thr Lys Gly Val Gly Ala Asp Gly Lys Ala Ala Gly Thr Pro
                180                 185                 190

Gly Pro Thr Gly Gln His Asp Gly Arg Arg Ile Gln Arg Glu Gly
            195                 200                 205

Leu Met Arg Val Tyr Val Ala Gln Leu Val Ala Arg Ala Ala Phe Glu
        210                 215                 220

Val Ala Phe Leu Val Gly Gln Tyr Leu Leu Tyr Gly Phe Glu Val Arg
225                 230                 235                 240

Pro Phe Phe Pro Cys Ser Arg Gln Pro Cys Pro His Val Val Asp Cys
                245                 250                 255

Phe Val Ser Arg Pro Thr Glu Lys Thr Val Phe Leu Leu Val Met Tyr
                260                 265                 270

Val Val Ser Cys Leu Cys Leu Leu Asn Leu Cys Glu Met Ala His
            275                 280                 285

Leu Gly Leu Gly Ser Ala Gln Asp Ala Val Arg Gly Arg Arg Gly Pro
        290                 295                 300

Pro Ala Ser Ala Pro Ala Pro Pro Arg Pro Pro Cys Ala Phe
305                 310                 315                 320

Pro Ala Ala Ala Ala Gly Leu Ala Cys Pro Pro Asp Tyr Ser Leu Val
                325                 330                 335

Val Arg Ala Ala Glu Arg Ala Arg Ala His Asp Gln Asn Leu Ala Asn
                340                 345                 350

Leu Ala Leu Gln Ala Leu Arg Asp Gly Ala Ala Gly Asp Arg Asp
        355                 360                 365

Arg Asp Ser Ser Pro Cys Val Gly Leu Pro Ala Ala Ser Arg Gly Pro
    370                 375                 380

Pro Arg Ala Gly Ala Pro Ala Ser Arg Thr Gly Ser Ala Thr Ser Ala
385                 390                 395                 400

Gly Thr Val Gly Glu Gln Gly Arg Pro Gly Thr His Glu Arg Pro Gly
                405                 410                 415

Ala Lys Pro Arg Ala Gly Ser Glu Lys Gly Ser Ala Ser Arg Asp
        420                 425                 430

Gly Lys Thr Thr Val Trp Ile
            435

<210> SEQ ID NO 11
<211> LENGTH: 429
<212> TYPE: PRT
<213> ORGANISM: Bos primigenius

<400> SEQUENCE: 11

Met Thr Asn Met Ser Trp Ser Phe Leu Thr Arg Leu Leu Glu Glu Ile
1               5                   10                  15

His Asn His Ser Thr Phe Val Gly Lys Val Trp Leu Thr Val Leu Val
                20                  25                  30

Val Phe Arg Ile Val Leu Thr Ala Val Gly Gly Glu Ser Ile Tyr Ser
            35                  40                  45

Asp Glu Gln Thr Lys Phe Thr Cys Asn Thr Arg Gln Pro Gly Cys Asp
        50                  55                  60
```

Asn Val Cys Tyr Asp Ala Phe Ala Pro Leu Ser His Val Arg Phe Trp
 65                  70                  75                  80

Val Phe Gln Ile Val Ile Ser Thr Pro Ser Val Met Tyr Leu Gly
                 85                  90                  95

Tyr Ala Val His Arg Leu Ala Arg Ala Ser Gln Asp Glu Arg Arg
                100                 105                 110

Ala Ser Arg Arg Pro Ser Arg Arg Ala Pro Arg Pro Pro Leu Pro
            115                 120                 125

Leu Pro Pro Pro Pro His Pro Gly Trp Pro Glu Pro Ala Asp Leu Gly
130                 135                 140

Glu Glu Glu Pro Met Leu Gly Leu Gly Glu Glu Asp Glu Asp Pro Gly
145                 150                 155                 160

Val Ala Glu Gly Leu Gly Glu Asp Glu Glu Ala Glu Asp Thr Gly Ala
                165                 170                 175

Ala Lys Gly Ala Gly Gly Asp Thr Lys Val Ala Gly Val Pro Gly Pro
            180                 185                 190

Ala Gly Gln His Asp Gly Arg Arg Ile Gln Arg Glu Gly Leu Met
            195                 200                 205

Arg Val Tyr Val Ala Gln Leu Val Ala Arg Ala Phe Glu Val Ala
210                 215                 220

Phe Leu Val Gly Gln Tyr Leu Leu Tyr Gly Phe Glu Val Arg Pro Phe
225                 230                 235                 240

Phe Ala Cys Ser Arg Gln Pro Cys Pro His Val Val Asp Cys Phe Val
                245                 250                 255

Ser Arg Pro Thr Glu Lys Thr Val Phe Leu Leu Val Met Tyr Val Val
            260                 265                 270

Ser Cys Leu Cys Leu Leu Leu Asn Leu Cys Glu Met Ala His Leu Gly
            275                 280                 285

Leu Gly Asn Ala Gln Asp Ala Val Arg Gly Arg Arg Pro Leu Pro Ala
290                 295                 300

Ser Pro Gly Pro Met Pro Arg Pro Pro Cys Ala Leu Pro Ala Ala
305                 310                 315                 320

Pro Ser Gly Leu Ala Cys Pro Pro Asp Tyr Ser Leu Val Val Arg Thr
                325                 330                 335

Ala Glu His Ala Arg Ala Gln Asp Gln Glu Leu Ala Ser Leu Ala Leu
            340                 345                 350

Gln Ala Leu Gln Asp Arg Arg Ala Leu Gly Asp Leu Asp Ser Pro Pro
            355                 360                 365

Gly Pro Gly Leu Pro Ala Asn Ala Arg Gly Pro Pro Lys Pro Gly Ala
    370                 375                 380

Pro Ala Ser Gly Ser Gly Ser Ala Thr Ser Gly Gly Thr Val Gly Gly
385                 390                 395                 400

Gln Gly Arg Gln Gly Ile Lys Pro Arg Met Gly Ser Glu Lys Gly Ser
                405                 410                 415

Gly Ser Ser Ser Arg Glu Gly Lys Thr Thr Val Trp Ile
            420                 425

<210> SEQ ID NO 12
<211> LENGTH: 440
<212> TYPE: PRT
<213> ORGANISM: Mus musculus

<400> SEQUENCE: 12

Met Thr Asn Met Ser Trp Ser Phe Leu Thr Arg Leu Leu Glu Glu Ile

-continued

```
1               5                   10                  15
His Asn His Ser Thr Phe Val Gly Lys Val Trp Leu Thr Val Leu Val
                20                  25                  30

Val Phe Arg Ile Val Leu Thr Ala Val Gly Gly Glu Ser Ile Tyr Ser
                35                  40                  45

Asp Glu Gln Ser Lys Phe Thr Cys Asn Thr Arg Gln Pro Gly Cys Asp
            50                  55                  60

Asn Val Cys Tyr Asp Ala Phe Ala Pro Leu Ser His Val Arg Phe Trp
65                  70                  75                  80

Val Phe Gln Ile Val Ile Ser Thr Pro Ser Val Met Tyr Leu Gly
                    85                  90                  95

Tyr Ala Val His Arg Leu Ala Arg Ala Ser Glu Gln Glu Arg Arg Arg
                100                 105                 110

Ala Leu Arg Arg Arg Pro Gly Thr Arg Arg Leu Pro Arg Ala Gln Leu
                115                 120                 125

Pro Pro Pro Pro Pro Gly Trp Pro Asp Thr Thr Asp Leu Gly Glu Ala
                130                 135                 140

Glu Pro Ile Leu Ala Leu Glu Glu Asp Glu Asp Glu Glu Pro Gly Ala
145                 150                 155                 160

Pro Glu Gly Pro Gly Glu Asp Thr Glu Glu Arg Ala Glu Asp Val
                    165                 170                 175

Ala Ala Lys Gly Gly Gly Gly Asp Gly Lys Thr Val Val Thr Pro Gly
                180                 185                 190

Pro Ala Gly Gln His Asp Gly Arg Arg Ile Gln Arg Glu Gly Leu
                    195                 200                 205

Met Arg Val Tyr Val Ala Gln Val Val Arg Ala Ala Phe Glu Val
        210                 215                 220

Ala Phe Leu Val Gly Gln Tyr Leu Leu Tyr Gly Phe Glu Val Pro Pro
225                 230                 235                 240

Phe Phe Ala Cys Ser Arg Gln Pro Cys Pro His Val Val Asp Cys Phe
                245                 250                 255

Val Ser Arg Pro Thr Glu Lys Thr Val Phe Leu Leu Val Met Tyr Val
                260                 265                 270

Val Ser Cys Leu Cys Leu Leu Leu Asn Leu Cys Glu Met Ala His Leu
            275                 280                 285

Gly Leu Gly Ser Ala Gln Asp Ala Val Arg Gly Arg Arg Gly Ala Ser
                290                 295                 300

Ala Ala Gly Pro Gly Pro Thr Pro Arg Pro Pro Cys Ala Phe Pro
305                 310                 315                 320

Ala Ala Ala Ala Gly Leu Ala Cys Pro Pro Asp Tyr Ser Leu Val Val
                325                 330                 335

Arg Ala Ala Glu Arg Ala Arg Ala His Asp Gln Asn Leu Ala Asn Leu
                340                 345                 350

Ala Leu Gln Ala Leu Arg Asp Gly Ala Ala Val Ala Ala Val Ser Ala
                355                 360                 365

Asp Arg Asp Ser Pro Pro Cys Ala Gly Leu Asn Ala Thr Ser Arg Gly
                370                 375                 380

Ala Pro Arg Val Gly Gly Leu Ala Ser Gly Thr Gly Ser Ala Thr Ser
385                 390                 395                 400

Gly Gly Thr Val Gly Glu Gln Ser Arg Pro Gly Ala Gln Glu Gln Leu
                    405                 410                 415

Ala Thr Lys Pro Arg Ala Gly Ser Glu Lys Gly Ser Thr Gly Ser Arg
                420                 425                 430
```

```
Asp Gly Lys Ala Thr Val Trp Ile
        435                 440

<210> SEQ ID NO 13
<211> LENGTH: 440
<212> TYPE: PRT
<213> ORGANISM: Rattus rattus

<400> SEQUENCE: 13

Met Thr Asn Met Ser Trp Ser Phe Leu Thr Arg Leu Leu Glu Glu Ile
1               5                   10                  15

His Asn His Ser Thr Phe Val Gly Lys Val Trp Leu Thr Val Leu Val
            20                  25                  30

Val Phe Arg Ile Val Leu Thr Ala Val Gly Gly Glu Ser Ile Tyr Ser
        35                  40                  45

Asp Glu Gln Ser Lys Phe Thr Cys Asn Thr Arg Gln Pro Gly Cys Asp
    50                  55                  60

Asn Val Cys Tyr Asp Ala Phe Ala Pro Leu Ser His Val Arg Phe Trp
65                  70                  75                  80

Val Phe Gln Ile Val Val Ile Ser Thr Pro Ser Val Met Tyr Leu Gly
                85                  90                  95

Tyr Ala Val His Arg Leu Ala Arg Ala Ser Glu Gln Glu Arg Arg Arg
            100                 105                 110

Ala Leu Arg Arg Arg Pro Gly Pro Arg Arg Leu Pro Arg Ala Gln Leu
        115                 120                 125

Pro Pro Pro Pro Pro Gly Trp Pro Asp Thr Thr Asp Leu Gly Glu Ala
    130                 135                 140

Glu Pro Ile Leu Ala Leu Glu Glu Asp Glu Asp Glu Glu Pro Gly Ala
145                 150                 155                 160

Pro Glu Gly Pro Gly Glu Asp Thr Glu Glu Arg Thr Glu Asp Val
                165                 170                 175

Ala Ala Lys Gly Gly Gly Gly Asp Gly Lys Thr Val Val Thr Pro Gly
            180                 185                 190

Pro Ala Gly Gln His Asp Gly Arg Arg Arg Ile Gln Arg Glu Gly Leu
        195                 200                 205

Met Arg Val Tyr Val Ala Gln Leu Val Val Arg Ala Ala Phe Glu Val
    210                 215                 220

Ala Phe Leu Val Gly Gln Tyr Leu Leu Tyr Gly Phe Glu Val Pro Pro
225                 230                 235                 240

Phe Phe Ala Cys Ser Arg Gln Pro Cys Pro His Val Val Asp Cys Phe
                245                 250                 255

Val Ser Arg Pro Thr Glu Lys Thr Val Phe Leu Leu Val Met Tyr Val
            260                 265                 270

Val Ser Cys Leu Cys Leu Leu Leu Asn Leu Cys Glu Met Ala His Leu
        275                 280                 285

Gly Leu Gly Ser Ala Gln Asp Ala Val Arg Gly Arg Gly Ala Ser
    290                 295                 300

Ala Ala Gly Pro Gly Pro Ala Pro Arg Pro Pro Cys Ala Phe Pro
305                 310                 315                 320

Ala Ala Ala Ala Gly Leu Ala Cys Pro Pro Asp Tyr Ser Leu Val Val
                325                 330                 335

Arg Ala Ala Glu Arg Ala Arg Ala His Asp Gln Asn Leu Ala Asn Leu
            340                 345                 350

Ala Leu Gln Ala Leu Arg Asp Gly Ala Ala Val Ala Ala Val Ser Ala
```

```
                355                 360                 365
Asp Arg Asp Ser Pro Pro Cys Ser Gly Leu Asn Ala Thr Ser Arg Gly
        370                 375                 380

Pro Pro Arg Ala Gly Gly Pro Ala Ser Gly Thr Gly Ser Ala Thr Ser
385                 390                 395                 400

Gly Gly Thr Val Gly Glu Gln Gly Arg Ser Gly Ala Gln Glu Gln Leu
                405                 410                 415

Ala Thr Lys Pro Arg Val Gly Ser Glu Lys Gly Ser Thr Gly Ser Arg
        420                 425                 430

Asp Gly Lys Ala Thr Val Trp Ile
        435                 440
```

<210> SEQ ID NO 14
<211> LENGTH: 34
<212> TYPE: DNA
<213> ORGANISM: Homo sapiens
<220> FEATURE:
<221> NAME/KEY: misc_feature
<222> LOCATION: (18)..(18)
<223> OTHER INFORMATION: n = single nucleotide polymorphism (guanine or adenine)

<400> SEQUENCE: 14
ggcatctgct gcctgccngc tcgtggctgc tgcc                                    34

<210> SEQ ID NO 15
<211> LENGTH: 32
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n = single nucleotide polymorphism (cytosine or guanine)

<400> SEQUENCE: 15
ggctgcatgg ggcagnctga ggctgcaggg gt                                      32

<210> SEQ ID NO 16
<211> LENGTH: 32
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n = single nucleotide polymorphism (guanine or adenine)

<400> SEQUENCE: 16
tgcctcttgg tgcccnaccc tgtgggtctg gc                                      32

<210> SEQ ID NO 17
<211> LENGTH: 32
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n = single nucleotide polymorphism (guanine or adenine)

<400> SEQUENCE: 17
ggaggttcta gatctcnagg tctaaggggt tc                                      32

<210> SEQ ID NO 18

```
<211> LENGTH: 32
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n = single nucleotide polymorphism (guanine or
      adenine)

<400> SEQUENCE: 18
gcctctgggg tggggtntag acagatgggt gg                                 32

<210> SEQ ID NO 19
<211> LENGTH: 31
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n = single nucleotide polymorphism (guanine or
      cytosine)

<400> SEQUENCE: 19
tctggggtgg ggtgtanaca gatgggtggg a                                  31

<210> SEQ ID NO 20
<211> LENGTH: 31
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n = guanine or nothing

<400> SEQUENCE: 20
ggtggggtgt agacanatgg gtgggagaga a                                  31

<210> SEQ ID NO 21
<211> LENGTH: 31
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n = single nucleotide polymorphism (cytosine or
      thymine)

<400> SEQUENCE: 21
cagagcccag actgcnggag gatacaggcc a                                  31

<210> SEQ ID NO 22
<211> LENGTH: 30
<212> TYPE: DNA
<213> ORGANISM: Homo sapiens
<220> FEATURE:
<221> NAME/KEY: misc_feature
<222> LOCATION: (15)..(15)
<223> OTHER INFORMATION: n = single nucleotide polymorphism (guanine or
      adenine)

<400> SEQUENCE: 22
cgcctggact gggcngctgg gcagggagg                                     30

<210> SEQ ID NO 23
<211> LENGTH: 30
<212> TYPE: DNA
<213> ORGANISM: Homo sapiens
<220> FEATURE:
<221> NAME/KEY: misc_feature
```

```
<222> LOCATION: (15)..(15)
<223> OTHER INFORMATION: n = cytosine or nothing

<400> SEQUENCE: 23
gagggcccag gcagnccccg gtcgcttgct                                    30

<210> SEQ ID NO 24
<211> LENGTH: 29
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n = single nucleotide polymorphism (guanine or
      thymine)

<400> SEQUENCE: 24
ccacacaccc tcgggnagga ccagcatcc                                     29

<210> SEQ ID NO 25
<211> LENGTH: 31
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n = single nucleotide polymorphism (cytosine or
      thymine)

<400> SEQUENCE: 25
caggagacag cctcangctg tgcccttgg c                                   31
```